(12) United States Patent
Kaplan et al.

(10) Patent No.: US 7,718,783 B2
(45) Date of Patent: May 18, 2010

(54) ELF3 GENE COMPOSITIONS AND METHODS

(76) Inventors: Mark H. Kaplan, 1835 Prairie Dunes Ct. South, Ann Arbor, MI (US) 48108; Michael H. Dosik, 22 Conscience Ct., East Setauket, NY (US) 11733; Xue-Ping Wang, 18 Pequot Ave., Port Washington, NY (US) 11050

(*) Notice: Subject to any disclaimer, the term of this patent is extended or adjusted under 35 U.S.C. 154(b) by 0 days.

(21) Appl. No.: 10/535,378

(22) PCT Filed: Nov. 21, 2003

(86) PCT No.: PCT/US03/37200

§ 371 (c)(1),
(2), (4) Date: Jun. 29, 2006

(87) PCT Pub. No.: WO2004/048516

PCT Pub. Date: Jun. 10, 2004

(65) Prior Publication Data

US 2006/0263775 A1 Nov. 23, 2006

Related U.S. Application Data

(60) Provisional application No. 60/428,335, filed on Nov. 22, 2002.

(51) Int. Cl.
*C07H 21/02* (2006.01)
*C12Q 1/68* (2006.01)
(52) U.S. Cl. .................................. 536/23.1; 435/6
(58) Field of Classification Search .................. 435/6, 435/91.2; 536/24.31, 24.32, 24.33, 23.1
See application file for complete search history.

(56) References Cited

U.S. PATENT DOCUMENTS 5,789,200 A 8/1998 Kola et al.

OTHER PUBLICATIONS

ChangCH et al. ESX: a structurally unique Ets overexpressed early during human breast tumerigenesis. Oncogene, vol. 14, pp. 1617-1622, 1997.*
Lowe T et al. A computer program for selection of oligonucleotide primers for polymerase chain reactions. Nucleic Acids Res., vol. 18, No. 7, pp. 1757-1761, 1990.*
Andreoli J.M. et al. "The expression of a novel, epithelium-specific ets transcription factor is restricted to the most differentiated layers in the epidermis"; Nucleic Acids Research, 1997, vol. 25, No. 21, pp. 4287-4295.
Barnes D.M. et al. "Overexpression of the c-erbB-2 oncoprotein: Why does this occur more frequently in ductal carcinoma in situ tahn in invasive mammary carcinoma and is this of prognostic significance?" European Journal of Cancer, 1992, vol. 28, No. 2/3, pp. 644-648.

Chang C-H. et al. "ESX: A structurally unique Ets overexpressed early during human breast tumorigenesis"; Oncogene, 1997, vol. 14, pp. 1617-1622.
Chang C-H. et al. "Exon 4-encoded acidic domain in the epithelium restricted Ets factor, ESX, confers potent transactivating capacity and binds to TATA-binding protein (TBP)"; Oncogene, 1999, vol. 18, pp. 3682-3695.
Chang J. et al. "Over-expression of ERT (ESX/ESE/ELF3), an ets-related transcription factor, induces endogenous TGF-beta type II receptor expression and retores the TGF-beta signaling pathway in Hs578t human breast cancer cells"; Oncogene, 2000, vol. 19, pp. 151-154.
Kim J-H. et al. "Activation of the Murine Type II Transforming Growth Factor-Beta Receptor Gene" Journal of Biological Chemistry, 2002, vol. 277, No. 20, pp. 17520-17530.
Ma Y. et al. "Microarray analysis uncovers retinoid targets in human bronchial epithelial cells"; Oncogene, 2003, vol. 22, pp. 4924-4932.
Oettgen P. et al. "The Novel Epithelial-Specific Ets Transcription Factor Gene ESX Maps to Human Chromosome 1q32.1"; Genomics, 1997, vol. 45, pp. 456-457.
Oettgen P. et al. "Isolation and Characterization of a Novel Epithelium-Specific Transcription Factor, ESE-1, a Member of the ets Family"; Molecular and Cellular Biology, 1997, vol. 17, No. 8, pp. 4419-4433.
Oettgen P. et al. "Genomic Organization of the Human ELF3 (ESE-1/ESX) Gene, A Member of the Ets Transcription Factor Family, and Identification of a Functional Promoter"; Genomics, 1999, vol. 55, No. 3, pp. 358-362.
Raynor M. et al. "Optimisation of the RT-PCR detection of immunomagnetically enriched carcinoma cells"; BMC Cancer, 2002, vol. 2, p. 14 et seq.
Roy-Engel A.M. et al. "Alu Insertion Polymorphisms for the Study of Human Genomic Diversity"; Genetics, 2001, vol. 159, pp. 279-290.
Tang Y. et al. "ELF a Beta-spectrin is a neuronal precursor cell marker in developing mammalian brain; structure and organization of the elf/beta-G spectrin gene"; Oncogene, 2002, vol. 21, pp. 5255-5267.
Tymms M.J. et al. "A novel epithelial-expressed ETS gene, ELF3: human and murine cDNA sequences, murine genomic organization, human mapping to 1q32.2 and expression in tissues and cancer"; Oncogene, 1997, vol. 15, pp. 2449-2462.

* cited by examiner

*Primary Examiner*—Suryaprabha Chunduru
(74) *Attorney, Agent, or Firm*—Amster, Rothstein, Ebenstein LLP

(57) ABSTRACT

ELF3 gene compositions associated with cancer are provided, including ELF3 mRNA intron retention, a novel ELF3 5' untranslated region, and a novel Alu, $Alu_{fwd}$. Methods and kits using primers or probes to detect the presence of these ELF3 gene compositions are also provided. Methods for determining whether a cell comprises a virus are also provided.

4 Claims, 21 Drawing Sheets

FIG. 1
A
B

FIG. 5
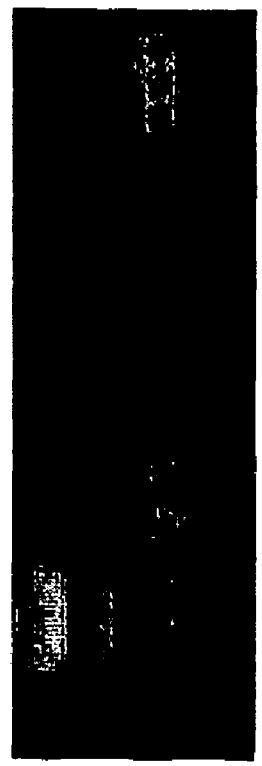
M D R N P

FIG. 9
a. Schematic diagram of human ELF3 gene
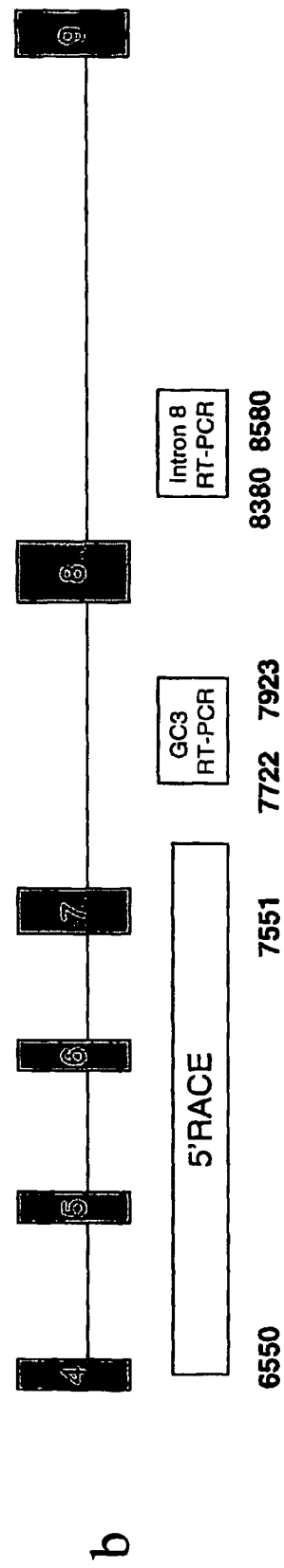
b. Unspliced mRNA of human ELF3 in human breast cancer cells
c. Fully spliced ELF3 mRNA FIG. 20
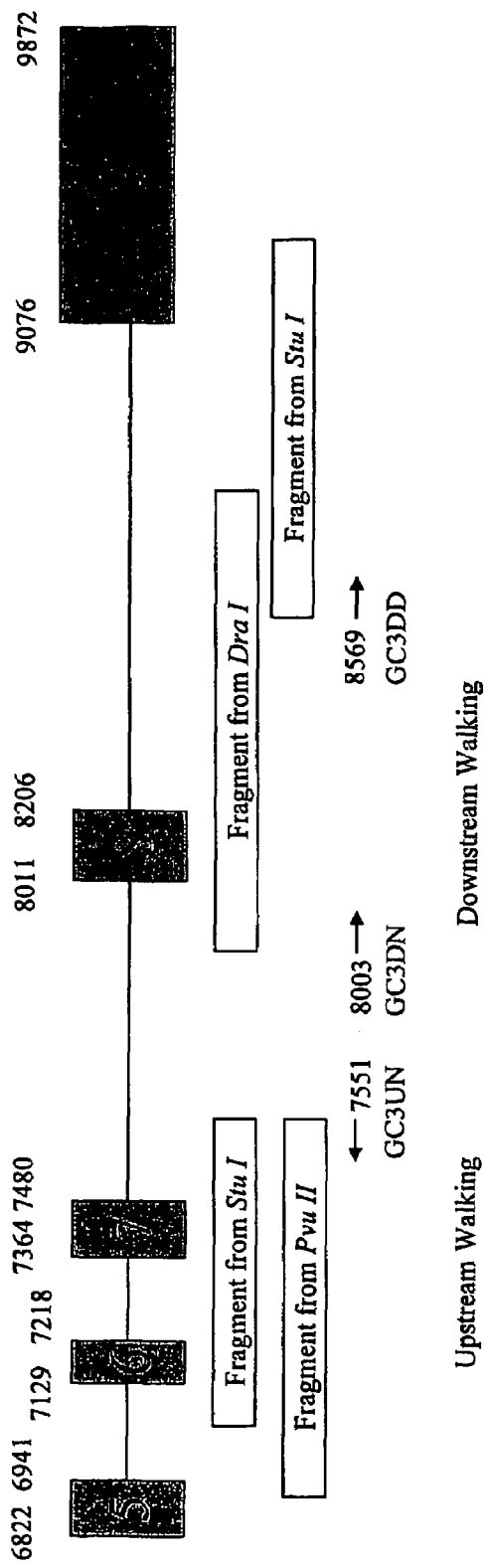
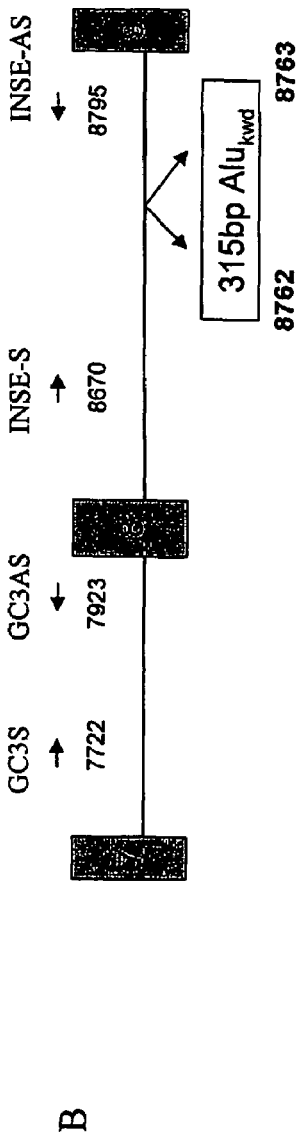

SEQUENCE LISTING

<160> NUMBER OF SEQ ID NOS: 34

<210> SEQ ID NO 1
<211> LENGTH: 10772
<212> TYPE: DNA
<213> ORGANISM: Homo sapiens

<400> SEQUENCE: 1

-continued

```
aagcttctta ggcatgtgta tgtgtgtttc ttgcagggga agcagaagta tacacttccg      60
ctgtaccacg caatgatggg tggcagtgag gtggcccaga ccctcgccaa ggagactttt     120
gcatccaccg cctcccagct ccacagcaat gttgtcaact atgtccagca gatcgtggca     180
cccaagggca gttagaggct cgtgtgcatg gcccctgcct cttcaggctc tccaggcttt     240
cagaataatt gtttgttccc aaattcctgt tccctgatca acttcctgga gtttatatcc     300
cctcaggata atctattctc tagcttaggt atctgtgact cttgggcctc tgctctggtg     360
ggaacttact tctctatagc ccactgagcc ccgagacaga gaacctgccc acagctctcc     420
ccgctacagg ctgcaggcac tgcagggcag cgggtattct cctccccacc taagtctctg     480
ggaagaagtg gagaggactg atgctcttct tttttctctt tctgtccttt ttcttgctga     540
ttttatgcaa agggctggca ttctgattgt tcttttttca ggtttaatcc ttattttaat     600
aaagttttca agcaaaaatt aagttacgga ttgagtgact attaaatttc ttccaccaga     660
ggtcctcact gtgtttgttc aggaaaggtc actgggggag gcccagagaa tgacagtatt     720
ttcctgtcct cagggaacag ccagggtgaa ggaggtgggt gtcctacaca tgcatatgaa     780
aaaaaatatg gcaaaatggc acagctggtg caggaaaatg aaaaaggaat agcattccag     840
ttctccgtga agcagctgaa ttctctatct gcagcagcat tcccattatc ttttccatca     900
ctaagaaaaa aaaatgggct gggcacggtg gctcatgcct gtaatcccag cactttggga     960
ggctgaggcg agaggatcgc ttgagcccag gagtttgaga ccaccctggc caacatagca    1020
ggacttcatc tctaccaaaa aaaaaaaaaa aaaaaaaaaa aagccaggcg tggtggctca    1080
cgcctgtaat ctcaacactt tgggaggctg aggcaggcaa atcacttgag gtcagaagtt    1140
tgagaccagc atggccaaca tggtgaaacc ccatctctac tgaaaaaaaa gatagatgca    1200
aaaattagcc aggcatggtg gctcacacct gtagttccag ttacttggga ggctgaagca    1260
ggagaaacac ttgaacctgg gaggtggagg ttgcagtaaa ctgagatcat gccactgcac    1320
tccagcctgg gtgacagagt aagacttctc aaaaaaaaaa aaaaaaagct gggcgtggtg    1380
gtgcattcct gtggtttcag ctactcagga ggctgaggca ggaggatcac ttgagcccaa    1440
gaggtcaagg ccacagtgag tcttgattgt gccactgaac tccagcctga gtgacagagt    1500
gagaccctgt ctcaaaaata aaaataaagt gtcttatgac tttttatcta cccttctgcc    1560
catgcccaag gcttcactgg gcctcacctg tctttgatcc tagataacta tttgaatggt    1620
aatcaagtaa agtctttaga acttagcact aaattctgat ttcctggcct caacatgggg    1680
acctaaacag ttagcaatct gggtttggga gtgggatgag gggagggttg aagaaatat    1740
ttagtgtgtt tcatttgcct ttcttaaata cagggcaccc ctgaaacagg ctttgttcgc    1800
agctctgctc tgtcctcgga tttaggttat cgaacaggct tcctccctcc cctgcacaag    1860
ggttgggaat gagtcgattt gctttcactc agcaagagca agggactagt ggtgaccaag    1920
tggtagactg gagaggcctc tgccccgtgg cacacagctc caccatcaga gagggtgatg    1980
tgggtcatag gtgagggatc tggaggcccg gtatcggaag agcttctcca ggcactggca    2040
ttttgacagc aaactgcttc cgtggctctt tcaggactgt tcctgggcaa tatgttattg    2100
gcaaggacta ttttagggct atccagttgt ctccccctct ccccaacctt ttatctagct    2160
tatcagtagc tatctttcct tgctctgtac aaaaacctat agcaccaata ggcccagtaa    2220
tcatgaaggg tcagtgcaag gaaaggctgg aagcccttcc tctaacagcc gtgctgtgac    2280
tccactaact ttgtggggtc tcccattaca tagcgtgggt atcctgagct gtgcagcctg    2340
```

-continued

```
cctcactcac caccttggta cctgacagga ctactggatg tgcctgtcct tttgtaggac    2400
attctcccat cccaaagatg aggctgtgct gccgtgtggg caagctctgt ggggagaggg    2460
gaggccagtg ggttgttttt gccatcacag aatactggga agcccctggc atcctgctcc    2520
atagctctct tcaccactat cctggaacct tctccccacc cccatcccca tgcctccaag    2580
gcactgacct caaatccaag tctttctcac ttatctcaag ctgccagcct gtagggattc    2640
cttatctcag ctccatgtca gcggtgagga agccccaaga aggcaaggga gctgacagcc    2700
ttctcatttt tctcgtacat cctcctgttc accccgccat cccgggagcc ccagccagat    2760
gctcttcagg gcagggagca cgtgagcagc cctggggcta aagccggtt ctcccacatt     2820 cctgggtgag ggactgggtg gagggtgtgc ctgcctcagg ctccttgggg gaggcccct     2880 gaagggctgg ggaaaatcct actgagcccc aggctctcct gcctgcactg gcccagtgcg    2940
ggggcggggg ggcggggggga tcctacattt caaatgcata aaaatctaga tatgggctgg    3000
gcgcagtagc tcatgcctgt aatcccagca ctttgggagg ctgaggcagg cagatcatga    3060
ggtcaggaga tcgagtccat cctggctaac atggtgaaac cccgtctcta ctaaaaatac    3120
agaaagccgg gcatggcagc gggcgcctgt aatcccagct actcggaaag ctgaggcagg    3180
agaatcgctt gaacccacga gtcagaggtt gcagtgagca gatatcacgc cactgcactc    3240
caacctgggc gacagagcga gactccacct caaaacaaaa taaccaaat actagatctg     3300 gaagagatct tagggattat taaattcaga caacctcatt ttttatagat ggggaaacaa    3360
gcacagactc caagggtctc atccaagatc acacagttgc agatgctggc tacaagtctc    3420
ctgcctcaac cacctgtatt accccattca gggtctcaag aagggtctat aagacactat    3480
ccattgtgtt tcgggctgag tccatagaga caaccacaga catgggggac tctgcccaca    3540
gggaaggcaa gggctctggc catggagctg gatgggaaga ctctgaagcc cgaagacatt    3600
gaatcctgtg cagggaaaga gcgagggttt tgtgtacaac acacctgcat acctggatgt    3660
gaatctcagc tccacccctt caccaactct gtgtggcctg ggcaagccat tctaagggaa    3720
ccctccacac tgcaacttc atgtctataa aatgggaata accatgcatt ccttacagga    3780
cttttttggt gtgaggatta aatgagagaa tatgttgaaa agtgcttggt aaatatatta    3840
atactatgca ttccctcttc tttgaatgac gtgacccagg tagtcaggct tctgaccact    3900
agagggcagc agaaggtact ggaaaactgg gccgagtgaa ccagagatta gatggggtcc    3960
agagagcagg gatgaactta cccgtgtgga ttctggcaac tccggcaggg agggctccag    4020
caggcgctga gggaagaact ttcaagcaga gccgggtctc ttcaggagcg actgcagcaa    4080
ccctgatgct tggatggagt ccaggcaggt gatggtagtg aagaccttgc caacagagtg    4140
ggcgctggag aaggagccct ttagtgggga ccctggggcc acgactaggc tggcaggccc    4200
agccagcacc aattaatcca tgagtattgc ccagcattga gcctggagca ccttccagcc    4260
cctggccaga gtcctgggtg ttctgggaaa accctaaaa cctagtaact cctctcccta    4320
ctaggcctct tgttgctga atctctggaa tttaggggcc agcagctttc tgactcaggt    4380
cagccagggg ttcatgttcc ctcacttgcc ctcccctgc ctggcccatc tctgcctgg    4440 cccctgggag gaatttcctg ggccagaggg cagccgaaag cacagatgcc cacccagca    4500 acgttcccgc cacctgccca ggccagtgcc ccgtgcccaa cccagaggg tgcgggatga    4560 cagactctga caatcattaa accagccggg cctgatttcc cagcactgcc tgctaagatc    4620
cgggccaagt ggcactgaat atgcaaatca cctggggcca ggagcccagt ctaaaggcca    4680
ggaaatcccc tccatccaat gagacaccag ctcaggttac tgcagggac acactataaa    4740
```

```
gccctgagct cagggaggag ctccctccag gctctattta gagccgggta ggggagcgca    4800
gcggccagat acctcagcgc tacctggcgg aactggattt ctctcccgcc tgccggcctg    4860
cctgccacag ccggactccg ccactccggt aggattcccc gcctgtcatt ccctagccca    4920
gctcttggga aactgcagag gggtccagag gatttgcagt tctgaacctg cacactccag    4980
tctaggatct ccgagcaaga gcgtaggtgt cctgagggtc aaagaacaga gagagattgt    5040
ctctgggaag gcagaatggc catgacgccg ctagtctggc tccagggccc cagagatctg    5100
aggagggaag cccagctgga ggctcctgtg gtcctgccct ggtctgagat cttggagccc    5160
ttcttgaaga gacggtgtcc gcagagttgc tgatcttcct gccccctgggg gctactcttg    5220
cccagggttg ggcaaagcag agtagctggg agtgtaagga gaggaccctc gtcccctcac    5280
caacctcatc ctctctcccc ctacccacag gtagcctcat ggctgcaacc tgtgagatta    5340
gcaacatttt tagcaactac ttcagtgcga tgtacagctc ggaggactcc accctggcct    5400
ctgttccccc tgctgccacc tttggggccg atgacttggt actgaccctg agcaaccccc    5460
agatgtcatt ggagggtaca ggtgggtctc agcggggtgg gatggggcac ggagtgggag    5520
acagatccat ctaagggcct gttagacaaa tgggggaata ggcagggagg agggtctcta    5580
ggcaaattcc agggctagag gctgagactt agtgactgag gtgctggggg ttgtggggct    5640
gtgacaggca gagggaggtg tcagatacca ggacaagggt gttgtgaatg ctacctcctg    5700
cccctactct tgggatggct ccaagggctg aggtgtgaat ccccagtgtg ctccaggaat    5760
ggggctgtgt gggctgggag tggtggctca cgcctgtaat cccagcactt tgggaggctg    5820
agctgagcgg atcacctgag gtcaagagtt cgagaccagc ctagccaaca tggtgaaacc    5880
ccgtctctac taaaaataca aaaaaaaatt tatcccagcg tggtggtggg cacctataat    5940
cccagctact ggggaggctg acgcaggagt atcgcttgaa cctgggaggt ggaggttgct    6000
gtgagccgag attgtgccat tgcaccccag cctaggtgac aggagtgaga ctccatctca    6060
aaaaaaaaaa aaaaaatggg gctgtaaggt ctgctgggtg gcctgagctg agcctgtttc    6120
cctgcctggc ccttgcagag aaggccagct ggttggggga acagccccag ttctggtcga    6180
agacgcaggt tctggactgg atcagctacc aagtggagaa gaacaagtac gacgcaagcg    6240
ccattgactt ctcacgatgt gacatggatg gcgccaccct ctgcaattgt gcccttgagg    6300
agctgcgtct ggtctttggg cctctggggg accaactcca tgcccagctg cgagacctca    6360
gtgagtccag gccccctggag gctggggagc agctccacat gttgagctga gtcgagttca    6420
gtgtggccgt aggcaggccc tggagctctg ggccagctgc acagccagag agagcccttg    6480
agggagggat taggggagtg tgaccccttcc ttccttcctt gtcagcttcc agctcttctg    6540
atgagctcag ttggatcatt gagctgctgg agaaggatgg catggccttc caggaggccc    6600
tagacccagg gcccttttggt gagaacccgt tttctccttc cttccccagc ctgtcttgtc    6660
ccatccctgc ccctccacag agtgctagag atgaccccct cccagactt cttcctccct    6720
caattagaaa aattgcagca ggtcatcaga cccatgggca gcatcacctg tcctggtctg    6780
gtcccctgag ccctctctga gttctcacct cctcttccca gaccagggca gcccctttgc    6840
ccaggagctg ctggacgacg gtcagcaagc cagcccctac caccccggca gctgtggcgc    6900
aggagccccc tccctggca gctctgacgt ctccaccgca ggtgagagct ctctctgggc    6960
cacaacctcc cttccccgaa gtgtcccttg ttccctctgg ctcccagcac cataactcag    7020
gccttctggc aggaacagga acaggctggg aagtgtgtcc tgagagccag cagcgtggtt    7080
```

```
gaacagaagg tgggccggca ggggacttac tctgacccc  gccccaggg  actggtgctt   7140
ctcggagctc ccactcctca gactccggtg aagtgacgt  ggacctggat  cccactgatg   7200
gcaagctctt ccccagcggt gagtcgaggg aggtcccca  gagggcgtcc  catttagcaa   7260
tgcacagggg gcccggctct tcctgcagcc ttttcctgta gagggctac   tctccctaac   7320
tcccctcttg cccctccttg accttccacc accgtccca  cagatggttt  tcgtgactgc   7380
aagaaggggg atcccaagca cgggaagcgg aaacgaggcc ggccccgaaa  gctgagcaaa   7440
gagtactggg actgtctcga gggcaagaag agcaagcacg gtgagctccg  ggggcacgtg   7500
ggtcctccct gcgccgggct gagcggcttc ctggggcact gcgggttgtt  gcaggtatcc   7560
cttctcccgt tttctctggc ctccgcatgg cctttggtaa ggctgtgcac  aagctggggg   7620
ctctatggta tcggtcacca cctaattgca gagcctggct tggtggtcct  ggagaggagg   7680
aggaaataag gctcccagtg ggaggctcat ggtaccagag tcctgtccac  tgactccagt   7740
gtcctgtcca ctgactccag ttctctctgc acttggccac tgtcctgccc  tctgggacac   7800
cctcaatgtg aggaggcagc tggtgggtct taggtgggct gaggagaaaa  gcagtcactg   7860
cagtacccgc acagagggca ctgcggggtc tctggagagg cttgctgcat  gctgtggcca   7920
agtcagcagt gcactggggc gggcagggct ggctggcctt gggtgagagg  ggacacctgg   7980
atggcaaact gatggaggct ggccttgcag cgcccagagg cacccacctg  tgggagttca   8040
tccgggacat cctcatccac ccggagctca acgagggcct catgaagtgg  gagaatcggc   8100
atgaaggcgt cttcaagttc ctgcgctccg aggctgtggc ccaactatgg  ggccaaaaga   8160
aaaagaacag caacatgacc tacgagaagc tgagccgggc catgaggtga  gctggcggcc   8220
aggaccctca cgatacagcc ggacatgggg acaggcgctc acactcccac  cgccctcttt   8280
ctggctgcca cttggtttct tgcaacaggg ctgagtcctt agagtgagga  caacatctgg   8340
gttggtctac ttcatggatt aaatgacaac atggagaaag tattagcctg  gcagacagca   8400
gacacagtgc acttgagcta gcagcaacat ttcttgtatc gcctgtgagg  cttgtcctca   8460
ggaaggcacc tggagagtgg gaaaggggggc aggagccgtg cccacccagg  gcctggcttt   8520
ctcctcgttg aagcacttag gttgtttttc tctgggcctc agtttcctcc  tgtgtccagg   8580
agtacactag atcatcttaa gatcccgtcc agccctaaaa tcatgtactt  acttttttt    8640
tcttttttctt ttttaaatag aggcaagggt ctctacgttg gccaggccgg  tctcaaactc   8700
ctggcctcaa atgactctcc tgcctcggcc tctcaaagtg ctgggattac  aggtgtgagc   8760
caccgtgccc agctccctgg ccttaaaagt catgtaattt aatgatcaga  ccccagtcac   8820
agccatagga tacaaagaag caaaggcaaa gagccctgtg tcctgggcac  ggttacaggc   8880
cagtgtaggg aaagagcttc tgcttgccag tgtgaagaac agaggagttt  aggaagtgtg   8940
agtcaggctc agcttagtca ggcagagacc agtgggcatg ggttacctgg  gggtaacgcg   9000
ggccaggtgg gcgggctggc agcctggggc ccatttcctg ccaaagcacc  tctgaccatc   9060
cttctcttca cccaggtact actacaaacg ggagatcctg gaacgggtgg  atggccggcg   9120
actcgtctac aagtttggca aaaactcaag cggctggaag gaggaagagg  ttctccagag   9180
tcggaactga gggttggaac tatacccggg accaaactca cggaccactc  gaggcctgca   9240
aaccttcctg ggaggacagg caggccagat ggccctcca  ctgggaatg   ctcccagctg   9300
tgctgtggag agaagctgat gttttggtgt attgtcagcc atcgtcctgg  gactcggaga   9360
ctatggcctc gcctccccac cctcctcttg gaattacaag ccctgggggtt  tgaagctgac   9420
tttatagctg caagtgtatc tcctttttatc tggtgcctcc tcaaacccag  tctcagacac   9480
```

```
taaatgcaga caacaccttc ctcctgcaga cacctggact gagccaagga ggcctgggga    9540
ggccctaggg gagcaccgtg atggagagga cagagcaggg gctccagcac cttctttctg    9600
gactggcgtt cacctccctg ctcagtgctt gggctccacg ggcagggtc agagcactcc     9660 ctaatttatg tgctatataa atatgtcaga tgtacataga gatctatttt ttctaaaaca    9720
ttcccctccc cactcctctc ccacagagtg ctggactgtt ccaggccctc cagtgggctg    9780
atgctgggac ccttaggatg gggctcccag ctcctttctc ctgtgaatgg aggcagagac    9840
ctccaataaa gtgccttctg ggcttttttct aacctttgtc ttagctacct gtgtactgaa   9900
atttgggcct ttggatcgaa tatggtcaag aggttggagg ggaggaaaat gaaggtctac    9960
caggctgagg gtgagggcaa aggctgacga agagggagt tacagatttc ctgtagcagg     10020
tgtgggctta cagacacatg gactgggctg ggaggcgagc aaaggaagca gctgagactg    10080
ttggagaacg cttacaagac ttcatgcaag caaggacatg aactcagaac actgaggtca    10140
gaagcatcct gctgtcatga caccgctcga gtgaccttga ccttgaccaa gtctgtcctg    10200
tttaggactg atttttccta ttaggctagg gtttggacct gatgttctca agatgtctag    10260
aattgcatgg ctggccttgt ggaatagatg gttttgcatt ccagccaagt gtgctgtaaa    10320
ctgtatatct gtaatatgaa tcccagcttt tgagtctgac aaaatcagag ttaggatctt    10380
gtaaaggaaa aaaaaaaaaa caaacaaaa tggagatgag tacttgctga gaaagaatga     10440
gggaaggagt tggcatttgt tgaaagtata gtcttttttct cttttttttt taattgcaac   10500
ttttacttta gatttaggag gtcgtgcgca ggtttgttac atgggtatat tgtgtgatgc    10560
tgagcttggg atgcgaatga tcctgtcacc caggtagtga gtatagcacc cagtgaaact    10620
gtagtctcat gccaggcact gtgctagccc actctggctc atttaatcct ctcctaagaa    10680
gagaggagac acagcgtccc catttgacag atgcagaaag aggttccaca ggtgtgcctt    10740
gattctgtcc taaaaccgtt tcccggaagc tt                                  10772

<210> SEQ ID NO 2
<211> LENGTH: 1959
<212> TYPE: DNA
<213> ORGANISM: Homo sapiens

<400> SEQUENCE: 2
ctccgccact ccggtaggat tccccgcctg tcattcccta gcccagctct tgggaaactg      60
cagaggggtc cagaggattt gcagttctga acctgcacac tccagtctag gatctccgag    120
caagagcgta gcctcatggc tacaacctgt gagattagca acatttttag caactacttc    180
agtgcgatgt acagctcgga ggactccacc ctggcctctg ttcccctgc tgccaccttt     240 ggggccgatg acttggtact gaccctgagc aacccccaga tgtcattgga gggtacagag    300
aaggccagct ggttggggga acagccccag ttctggttga agacgcaggt tctggactgg    360
atcagctacc aagtggagaa gaacaagtac gacgcaagcg ccattgactt ctcacgatgt    420
gacatggatg gcgccaccct ctgcaattgt gcccttgagg agctgcgtct ggtctttggg    480
cctctggggg accaactcca tgcccagttg cgagacctca cttccagctc ttcttatgag    540
ctcagttgga tcattgagct gctggagaag gatggcatgg ccttcaggga ggccctagac    600
ccagggccct ttgaccaggg cagccccttt gcccaggagc tgctggacga cggtcagcaa    660
gccagcccct accaccccgg cagttgtggc gcaggagccc cctcccccgg cagctctgac    720
gtctccaccg cagggactgg tgcttctcgg agctcccact cctcagactc cggtggaagt    780
```

```
gacgtggacc tggatcccac tgatggcaag ctcttcccca gcgatggttt tcgtgactgc    840 aagaagggggg atcccaagca cgggaagcgg aaacgaggcc ggccccgaaa gctgagcaaa    900
gagtgctggg actgtctcga gggcaagaag agcaagcacg cgcccagagg cacccacctg    960
tgggagttca tccgggacat cctcatccac ccggagctca acgagggcct catgaagtgg   1020
gagaatcgac atgaaggcgt cttcaagttc ctgcgctccg aggctgtggc ccaactatgg   1080
ggccaaaaga aaaagaacag caacatgacc tacgagaagc tgagccgggc catgaggtac   1140
tactacaaac gggagatcct ggaacgggtg gatggccggc gactcgtcta caagtttggc   1200
aaaaactcaa gcgctggaa ggaggaagag gttctccaga gtcggaactg agggttggaa   1260
ctatacccgg gaccaaactc acggaccact cgaggcctgc aaaccttcct gggaggacag   1320
gcaggccaga tggcccctcc actggggaat gctcccagct gtgctgtgga gaaagctga   1380 tgttttggtg tattgtcagc catcgtcctg ggactcggag actatggcct cgccttccca   1440
cccttctctt ggaattacaa agccctgggg tttgaactga cttttatagct tgcaagtgta   1500 tctccttta tctggtgcct cctcaaaccc agtcttcaaa cactaaatgc agacaacacc   1560
ttcttctgca acaccctgg acttgaccca aggaggcct ggggaggccc tagggggagca   1620 ccgtgatgag aggacagagc aggggctcca gcaccttctt tctggactgg cgttcacctc   1680
cctgctcagt gcttgggctc cacgggcagg ggtcagagca ctccctaatt tatgtgctat   1740
ataaatatgt cagatgtaca tagagatcta ttttttctaa acattccccc tccccactcc   1800
tctcccacag agtgctggac tgttccaggc cctccagtgg gctgatgctg ggacccttag   1860 gatgggctc ccagctcctt tctcctgtga atggaggcag agacctccaa taaagtgcct   1920 tctgggctt ttccaaaaaa aaaaaaaaaa aaaaaaaaa                         1959
```

<210> SEQ ID NO 3
<211> LENGTH: 371
<212> TYPE: PRT
<213> ORGANISM: Homo sapiens

<400> SEQUENCE: 3

```
Met Ala Ala Thr Cys Glu Ile Ser Asn Ile Phe Ser Asn Tyr Phe Ser
1               5                  10                  15

Ala Met Tyr Ser Ser Glu Asp Ser Thr Leu Ala Ser Val Pro Pro Ala
            20                  25                  30

Ala Thr Phe Gly Ala Asp Asp Leu Val Leu Thr Leu Ser Asn Pro Gln
        35                  40                  45

Met Ser Leu Glu Gly Thr Glu Lys Ala Ser Trp Leu Gly Glu Gln Pro
    50                  55                  60

Gln Phe Trp Ser Lys Thr Gln Val Leu Asp Trp Ile Ser Tyr Gln Val
65                  70                  75                  80

Glu Lys Asn Lys Tyr Asp Ala Ser Ala Ile Asp Phe Ser Arg Cys Asp
                85                  90                  95

Met Asp Gly Ala Thr Leu Cys Asn Cys Ala Leu Glu Glu Leu Arg Leu
            100                 105                 110

Val Phe Gly Pro Leu Gly Asp Gln Leu His Ala Gln Leu Arg Asp Leu
        115                 120                 125

Thr Ser Ser Ser Asp Glu Leu Ser Trp Ile Ile Glu Leu Leu Glu
    130                 135                 140

Lys Asp Gly Met Ala Phe Gln Glu Ala Leu Asp Pro Gly Pro Phe Asp
145                 150                 155                 160

Gln Gly Ser Pro Phe Ala Gln Glu Leu Leu Asp Asp Gly Gln Gln Ala
```

```
                165                 170                 175
Ser Pro Tyr His Pro Gly Ser Cys Gly Ala Gly Ala Pro Ser Pro Gly
            180                 185                 190

Ser Ser Asp Val Ser Thr Ala Gly Thr Gly Ala Ser Arg Ser Ser His
            195                 200                 205

Ser Ser Asp Ser Gly Gly Ser Asp Val Asp Leu Asp Pro Thr Asp Gly
            210                 215                 220

Lys Leu Phe Pro Ser Asp Gly Phe Arg Asp Cys Lys Lys Gly Asp Pro
225                 230                 235                 240

Lys His Gly Lys Arg Lys Arg Gly Arg Pro Arg Lys Leu Ser Lys Glu
            245                 250                 255

Tyr Trp Asp Cys Leu Glu Gly Lys Lys Ser Lys His Ala Pro Arg Gly
            260                 265                 270

Thr His Leu Trp Glu Phe Ile Arg Asp Ile Leu Ile His Pro Glu Leu
            275                 280                 285

Asn Glu Gly Leu Met Lys Trp Glu Asn Arg His Glu Gly Val Phe Lys
            290                 295                 300

Phe Leu Arg Ser Glu Ala Val Ala Gln Leu Trp Gly Gln Lys Lys Lys
305                 310                 315                 320

Asn Ser Asn Met Thr Tyr Glu Lys Leu Ser Arg Ala Met Arg Tyr Tyr
            325                 330                 335

Tyr Lys Arg Glu Ile Leu Glu Arg Val Asp Gly Arg Arg Leu Val Tyr
            340                 345                 350

Lys Phe Gly Lys Asn Ser Ser Gly Trp Lys Glu Glu Val Leu Gln
            355                 360                 365

Ser Arg Asn
    370

<210> SEQ ID NO 4
<211> LENGTH: 371
<212> TYPE: PRT
<213> ORGANISM: Homo sapiens

<400> SEQUENCE: 4

Met Ala Thr Thr Cys Glu Ile Ser Asn Ile Phe Ser Asn Tyr Phe Ser
1               5                   10                  15

Ala Met Tyr Ser Ser Glu Asp Ser Thr Leu Ala Ser Val Pro Pro Ala
            20                  25                  30

Ala Thr Phe Gly Ala Asp Asp Leu Val Leu Thr Leu Ser Asn Pro Gln
        35                  40                  45

Met Ser Leu Glu Gly Thr Glu Lys Ala Ser Trp Leu Gly Glu Gln Pro
50                  55                  60

Gln Phe Trp Leu Lys Thr Gln Val Leu Asp Trp Ile Ser Tyr Gln Val
65                  70                  75                  80

Glu Lys Asn Lys Tyr Asp Ala Ser Ala Ile Asp Phe Ser Arg Cys Asp
                85                  90                  95

Met Asp Gly Ala Thr Leu Cys Asn Cys Ala Leu Glu Glu Leu Arg Leu
            100                 105                 110

Val Phe Gly Pro Leu Gly Asp Gln Leu His Ala Gln Leu Arg Asp Leu
        115                 120                 125

Thr Ser Ser Ser Ser Tyr Glu Leu Ser Trp Ile Ile Glu Leu Leu Glu
        130                 135                 140

Lys Asp Gly Met Ala Phe Gln Glu Ala Leu Asp Pro Gly Pro Phe Asp
145                 150                 155                 160
```

```
Gln Gly Ser Pro Phe Ala Gln Glu Leu Leu Asp Asp Gly Gln Gln Ala
                165                 170                 175

Ser Pro Tyr His Pro Gly Ser Cys Gly Ala Gly Ala Pro Ser Pro Gly
            180                 185                 190

Ser Ser Asp Val Ser Thr Ala Gly Thr Gly Ala Ser Arg Ser Ser His
        195                 200                 205

Ser Ser Asp Ser Gly Ser Asp Val Asp Leu Asp Pro Thr Asp Gly
    210                 215                 220

Lys Leu Phe Pro Ser Asp Gly Phe Arg Asp Cys Lys Lys Gly Asp Pro
225                 230                 235                 240

Lys His Gly Lys Arg Lys Arg Gly Arg Pro Arg Lys Leu Ser Lys Glu
                245                 250                 255

Cys Trp Asp Cys Leu Glu Gly Lys Lys Ser Lys His Ala Pro Arg Gly
            260                 265                 270

Thr His Leu Trp Glu Phe Ile Arg Asp Ile Leu Ile His Pro Glu Leu
        275                 280                 285

Asn Glu Gly Leu Met Lys Trp Glu Asn Arg His Glu Gly Val Phe Lys
    290                 295                 300

Phe Leu Arg Ser Glu Ala Val Ala Gln Leu Trp Gly Gln Lys Lys Lys
305                 310                 315                 320

Asn Ser Asn Met Thr Tyr Glu Lys Leu Ser Arg Ala Met Arg Tyr Tyr
                325                 330                 335

Tyr Lys Arg Glu Ile Leu Glu Arg Val Asp Gly Arg Arg Leu Val Tyr
            340                 345                 350

Lys Phe Gly Lys Asn Ser Ser Gly Trp Lys Glu Glu Val Leu Gln
        355                 360                 365

Ser Arg Asn
    370

<210> SEQ ID NO 5
<211> LENGTH: 203
<212> TYPE: DNA
<213> ORGANISM: Homo sapiens

<400> SEQUENCE: 5
gtgagaaccc gttttctcct tccttcccca gcctgtcttg tcccatccct gcccctccac      60
agagtgctag agatgacccc ctccccagac ttcttcctcc ctcaattaga aaaattgcag     120
caggtcatca gacccatggg cagcatcacc tgtcctggtc tggtccctg agccctctct      180 gagttctcac ctcctcttcc cag                                             203

<210> SEQ ID NO 6
<211> LENGTH: 187
<212> TYPE: DNA
<213> ORGANISM: Homo sapiens

<400> SEQUENCE: 6
gtgagagctc tctctgggcc acaacctccc ttccccgaag tgtcccttgt tccctctggc      60
tcccagcacc ataactcagg ccttctggca ggaacaggaa caggctggga agtgtgtcct     120
gagagccagc agcgtggttg aacagaaggt gggccggcag gggacttact ctgaccccgc     180
cccccag                                                              187

<210> SEQ ID NO 7
<211> LENGTH: 145
<212> TYPE: DNA
<213> ORGANISM: Homo sapiens
```

<400> SEQUENCE: 7

```
gtgagtcgag ggaggtcccc aagagggcgt cccatttagc aatgcacagg gggcccggct        60
cttcctgcag ccttttcctg tagaggggct actctcccta actcccctct tgcccctcct       120
tgaccttcca ccaccgtccc cacag                                             145
```

<210> SEQ ID NO 8
<211> LENGTH: 530
<212> TYPE: DNA
<213> ORGANISM: Homo sapiens

<400> SEQUENCE: 8

```
gtgagctccg ggggcacgtg ggtcctccct gcgccgggct gagcggcttc ctggggcact        60
gcgggttgtt gcaggtatcc cttctcccgt tttctctggc ctccgcatgg cctttggtaa       120
ggctgtgcac aagctggggg ctctatggta tcggtcacca cctaattgca gagcctggct       180
tggtggtcct ggagaggagg aggaaataag gctcccagtg ggaggctcat ggtaccagag       240
tcctgtccac tgactccagt gtcctgtcca ctgactccag ttctctctgc acttggccac       300
tgtcctgccc tctgggacac cctcaatgtg aggaggcagc tggtgggtct taggtgggct       360
gaggagaaaa gcagtcactg cagtacccgc acagagggca ctgcggggtc tctggagagg       420
cttgctgcat gctgtggcca agtcagcagt gcactggggg gggcagggct ggctggcctt       480
gggtgagagg ggacacctgg atggcaaact gatggaggct ggccttgcag                  530
```

<210> SEQ ID NO 9
<211> LENGTH: 869
<212> TYPE: DNA
<213> ORGANISM: Homo sapiens

<400> SEQUENCE: 9

```
gtgagctggc ggccaggacc ctcacgatac agccggacat ggggacaggc gctcacactc        60
ccaccgccct ctttctggct gccacttggt ttcttgcaac agggctgagt ccttagagtg       120
aggacaacat ctgggttggt ctacttcatg gattaaatga caacatggag aaagtattag       180
cctggcagac agcagacaca gtgcacttga gctagcagca acatttcttg tatcgcctgt       240
gaggcttgtc ctcaggaagg cacctggaga gtggaaagg gggcaggagc cgtgcccacc        300
cagggcctgg ctttctcctc gttgaagcac ttaggttgtt tttctctggg cctcagtttc       360
ctcctgtgtc caggagtaca ctagatcatc ttaagatccc gtccagccct aaaatcatgt       420
acttactttt tttttctttt tcttttttaa atagaggcaa gggtctctac gttggccagg       480
ccggtctcaa actcctggcc tcaaatgact ctcctgcctc ggcctctcaa agtgctggga       540
ttacaggtgt gagccaccgt gcccagctcc ctggccttaa aagtcatgta atttaatgat       600
cagaccccag tcagccat aggatacaaa gaagcaaagg caaagagccc tgtgtcctgg         660
gcacggttac aggccagtgt agggaaagag cttctgcttg ccagtgtgaa gaacagagga       720
gtttaggaag tgtgagtcag gctcagctta gtcaggcaga gaccagtggg catgggttac       780
ctgggggtaa cgcggggccag gtgggcgggc tggcagcctg gggcccattt cctgccaaag     840
cacctctgac catccttctc ttcacccag                                         869
```

<210> SEQ ID NO 10
<211> LENGTH: 5095
<212> TYPE: DNA
<213> ORGANISM: Homo sapiens

```
<400> SEQUENCE: 10
tttagagccg ggtaggggag cgcagcggcc agatacctca gcgctacctg gcggaactgg      60
atttctctcc cgcctgccgg cctgcctgcc acagccggac tccgccactc cggtaggatt     120
ccccgcctgt cattccctag cccagctctt gggaaactgc agaggggtcc agaggatttg     180
cagttctgaa cctgcacact ccagtctagg atctccgagc aagagcgtag gtgtcctgag     240
ggtcaaagaa cagagagaga ttgtctctgg aaggcagaa tggccatgac gccgctagtc     300
tggctccagg gccccagaga tctgaggagg aagcccagc tggaggctcc tgtggtcctg      360
ccctggtctg agatcttgga gcccttcttg aagagacggt gtccgcagag ttgctgatct     420
tcctgcccct gggggctact cttgcccagg gttgggcaaa gcagagtagc tgggagtgta     480
aggagaggac cctcgtcccc tcaccaacct catcctctct cccctaccc acaggtagcc      540
tcatggctgc aacctgtgag attagcaaca ttttagcaa ctacttcagt gcgatgtaca      600
gctcggagga ctccaccctg gcctctgttc ccctgctgc cacctttggg gccgatgact      660
tggtactgac cctgagcaac ccccagatgt cattggaggg tacaggtggg tctcagcggg     720
gtgggatggg gcacggagtg ggagacagat ccatctaagg gcctgttaga caaatggggg     780
aataggcagg gaggagggtc tctaggcaaa ttccagggct agaggctgag acttagtgac     840
tgaggtgctg ggggttgtgg ggctgtgaca ggcagaggga ggtgtcagat accaggacaa     900
gggtgttgtg aatgctacct cctgccccta ctcttgggat ggctccaagg gctgaggtgt     960
gaatccccag tgtgctccag gaatgggct gtgtgggctg ggagtggtgg ctcacgcctg     1020
taatcccagc actttgggag gctgagctga gcggatcacc tgaggtcaag agttcgagac    1080
cagcctagcc aacatggtga aacccgtct ctactaaaaa tacaaaaaaa aatttatccc     1140
agcgtggtgg tgggcaccta taatcccagc tactggggag gctgacgcag gagtatcgct    1200
tgaacctggg aggtggaggt tgctgtgagc cgagattgtg ccattgcacc ccagcctagg    1260
tgacaggagt gagactccat ctcaaaaaaa aaaaaaaaa tggggctgta aggtctgctg     1320
ggtggcctga gctgagcctg tttccctgcc tggcccttgc agagaaggcc agctggttgg    1380
gggaacagcc ccagttctgg tcgaagacgc aggttctgga ctggatcagc taccaagtgg    1440
agaagaacaa gtacgacgca agcgccattg acttctcacg atgtgacatg gatgcgcca     1500
ccctctgcaa ttgtgccctt gaggagctgc gtctggtctt tgggcctctg ggggaccaac    1560
tccatgccca gctgcgagac ctcagtgagt ccaggcccct ggaggctggg gagcagctcc    1620
acatgttgag ctgagtcgag ttcagtgtgg ccgtaggcag gccctggagc tctgggccag    1680
ctgcacagcc agagagagcc cttgagggag ggattagggg agtgtgaccc ttccttcctt    1740
ccttgtcagc ttccagctct tctgatgagc tcagttggat cattgagctg ctggagaagg    1800
atggcatggc cttccaggag gccctagacc cagggccctt tggtgagaac ccgtttttctc   1860
cttccttccc cagcctgtct tgtcccatcc ctgcccctcc acagagtgct agagatgacc    1920
ccctccccag acttcttcct ccctcaatta gaaaaattgc agcaggtcat cagacccatg    1980
ggcagcatca cctgtcctgg tctggtcccc tgagccctct ctgagttctc acctcctctt    2040
cccagaccag ggcagcccct ttgcccagga gctgctggac gacggtcagc aagccagccc    2100
ctaccacccc ggcagctgtg gcgcaggagc cccctcccct ggcagctctg acgtctccac    2160
cgcaggtgag agctctctct gggccacaac ctcccttccc cgaagtgtcc cttgttccct    2220
ctggctccca gcaccataac tcaggccttc tggcaggaac aggaacaggc tgggaagtgt    2280
gtcctgagag ccagcagcgt ggttgaacag aaggtgggcc ggcaggggac ttactctgac    2340
```

```
cccgccccc    agggactggt   gcttctcgga   gctcccactc   ctcagactcc   ggtggaagtg   2400
acgtggacct   ggatcccact   gatggcaagc   tcttcccag    cggtgagtcg   agggaggtcc   2460
ccaagagggc   gtcccattta   gcaatgcaca   ggggcccgg    ctcttcctgc   agccttttcc   2520
tgtagagggg   ctactctccc   taactcccct   cttgcccctc   cttgaccttc   caccaccgtc   2580
cccacagatg   gttttcgtga   ctgcaagaag   ggggatccca   agcacgggaa   gcggaaacga   2640
ggccggcccc   gaaagctgag   caaagagtac   tgggactgtc   tcgagggcaa   gaagagcaag   2700
cacggtgagc   tccgggggca   cgtgggtcct   ccctgcgccg   ggctgagcgg   cttcctgggg   2760
cactgcgggt   tgttgcaggt   atcccttctc   ccgttttctc   tggcctccgc   atggcctttg   2820
gtaaggctgt   gcacaagctg   ggggctctat   ggtatcggtc   accacctaat   tgcagagcct   2880
ggcttggtgg   tcctggagag   gaggaggaaa   taaggctccc   agtgggaggc   tcatggtacc   2940
agagtcctgt   ccactgactc   cagtgtcctg   tccactgact   ccagttctct   ctgcacttgg   3000
ccactgtcct   gccctctggg   acaccctcaa   tgtgaggagg   cagctggtgg   gtcttaggtg   3060
ggctgaggag   aaaagcagtc   actgcagtac   ccgcacagag   ggcactgcgg   ggtctctgga   3120
gaggcttgct   gcatgctgtg   gccaagtcag   cagtgcactg   gggcgggcag   ggctggctgg   3180
ccttgggtga   gaggggacac   ctggatggca   aactgatgga   ggctggcctt   gcagcgccca   3240
gaggcaccca   cctgtgggag   ttcatccggg   acatcctcat   ccacccggag   ctcaacgagg   3300
gcctcatgaa   gtgggagaat   cggcatgaag   gcgtcttcaa   gttcctgcgc   tccgaggctg   3360
tggcccaact   atggggccaa   agaaaaaga   acagcaacat   gacctacgag   aagctgagcc   3420
gggccatgag   gtgagctggc   ggccaggacc   ctcacgatac   agccggacat   ggggacaggc   3480
gctcacactc   ccaccgccct   ctttctggct   gccacttggt   tcttgcaac   agggctgagt   3540 ccttagagtg   aggacaacat   ctgggttggt   ctacttcatg   gattaaatga   caacatggag   3600
aaagtattag   cctggcagac   agcagacaca   gtgcacttga   gctagcagca   acatttcttg   3660
tatcgcctgt   gaggcttgtc   ctcaggaagg   cacctggaga   gtgggaaagg   gggcaggagc   3720
cgtgcccacc   cagggcctgg   ctttctcctc   gttgaagcac   ttaggttgtt   tttctctggg   3780
cctcagtttc   ctcctgtgtc   caggagtaca   ctagatcatc   ttaagatccc   gtccagccct   3840
aaaatcatgt   acttactttt   tttttctttt   tcttttttaa   atagaggcaa   gggtctctac   3900
gttggccagg   ccggtctcaa   actcctggcc   tcaaatgact   ctcctgcctc   ggcctctcaa   3960
agtgctggga   ttacaggtgt   gagccaccgt   gcccagctcc   ctggccttaa   aagtcatgta   4020
atttaatgat   cagaccccag   tcacagccat   aggatacaaa   gaagcaaagg   caaagagccc   4080
tgtgtcctgg   gcacggttac   aggccagtgt   agggaaagag   cttctgcttg   ccagtgtgaa   4140
gaacagagga   gtttaggaag   tgtgagtcag   gctcagctta   gtcaggcaga   gaccagtggg   4200
catgggttac   ctgggggtaa   cgcgggccag   gtgggcgggc   tggcagcctg   ggcccatt   4260 cctgccaaag   cacctctgac   catccttctc   ttcacccagg   tactactaca   aacgggagat   4320 cctgaacgg    gtggatggcc   ggcgactcgt   ctacaagttt   ggcaaaaact   caagcggctg   4380
gaaggaggaa   gaggttctcc   agagtcggaa   ctgagggttg   gaactatacc   cgggaccaaa   4440
ctcacggacc   actcgaggcc   tgcaaaccct   tcctgggagga   caggcaggcc   agatggcccc   4500
tccactgggg   aatgctccca   gctgtgctgt   ggagagaagc   tgatgttttg   gtgtattgtc   4560
agccatcgtc   ctgggactcg   gagactatgg   cctcgcctcc   ccaccctcct   cttggaatta   4620
caagccctgg   ggtttgaagc   tgactttata   gctgcaagtg   tatctccttt   tatctggtgc   4680
```

| | | | |
|---|---|---|---|
| ctcctcaaac | ccagtctcag | acactaaatg cagacaacac | cttcctcctg cagacacctg | 4740 |
| gactgagcca | aggaggcctg | gggaggccct | aggggagcac cgtgatggag aggacagagc | 4800 |
| aggggctcca | gcaccttctt | tctggactgg | cgttcacctc cctgctcagt gcttgggctc | 4860 |
| cacgggcagg | ggtcagagca | ctccctaatt | tatgtgctat ataaatatgt cagatgtaca | 4920 |
| tagagatcta | tttttttctaa | aacattcccc | tccccactcc tctcccacag agtgctggac | 4980 |
| tgttccaggc | cctccagtgg | gctgatgctg | ggacccttag gatggggctc ccagctcctt | 5040 |
| tctcctgtga | atggaggcag | agacctccaa | taaagtgcct tctgggcttt ttcta | 5095 |

<210> SEQ ID NO 11
<211> LENGTH: 531
<212> TYPE: DNA
<213> ORGANISM: Homo sapiens

<400> SEQUENCE: 11

| | | | |
|---|---|---|---|
| ccgggctgag | cggcttcctg | gggcactgcg | ggttgttgca ggtatcccct ctcccgtttc | 60 |
| ctctggcctc | cgcatggcct | ttggtaaggc | tgtgcacaag ctgggggctc tatggtatcg | 120 |
| gtcaccacct | aattgcagag | ccaggcttgg | tggtcctgga gaggaggagg aaataaggct | 180 |
| cccagtggga | ggctcatggt | accagagtcc | tgtccactga ctccagtgtc ctgtccactg | 240 |
| actccagttc | tctctgcact | tggccactgt | cctgccctct gggtcaccct caatgtgagg | 300 |
| aggcggctgg | tgggtcttag | gtgggctgag | gagaaaagca gtcactgcag tacccgcaca | 360 |
| gagggcactg | cggggtctct | ggagaggctt | gctgcatgct gtggccaagt caagcagtgc | 420 |
| actgggcgg | cagggctggc | tggccttggg | tgagagggg cacctggatg gcaaacggat | 480 |
| ggaggctggc | ttgcagcgcc | cagaggcacc | cacctgtggg agttcatccg g | 531 |

<210> SEQ ID NO 12
<211> LENGTH: 1002
<212> TYPE: DNA
<213> ORGANISM: Homo sapiens

<400> SEQUENCE: 12

| | | | |
|---|---|---|---|
| gttggatcat | tgagctgctg | gagaaggatg | gcatggcctt ccaggaggcc ctagacccag | 60 |
| ggcccttggg | tgagaacccg | ttttctcctt | ccttccccag cctgtcttgt cccatccctg | 120 |
| cccctccaca | gagtgctaga | gatgaccccc | tccccagact tcttcctccc tcaattagaa | 180 |
| aaattgcagc | aggtcatcag | acccatgggc | agcatcacct gtcctggtct ggtcccctga | 240 |
| gccctctctg | agttctcacc | tcctcttccc | agaccagggc agcccctttg cccaggagct | 300 |
| gctggacgac | ggtcagcaag | ccagccccta | ccaccccggc agctgtggcg caggagcccc | 360 |
| ctcccctggc | agctctgacg | tctccaccgc | aggtgagagc tctctctggg ccacaacctc | 420 |
| ccttccccga | agtgtccctt | gttccctctg | gctcccagca ccataactca ggccttctgg | 480 |
| caggaacagg | aacaggctgg | gaagtgtgtc | ctgagagcca gcagcgtggt tgaacagaag | 540 |
| gtgggccggc | aggggactta | ctctgacccc | gcccccagg actggtgct tctcggagct | 600 |
| cccactcctc | agactccggt | ggaagtgacg | tggacctgga tcccactgat ggcaagctct | 660 |
| tccccagcgg | tgagtcgagg | gaggtcccca | agagggcgtc ccatttagca atgcacaggg | 720 |
| ggcccggctc | ttcctgcagc | cttttcctgt | agaggggcta ctctcccta actcccctctt | 780 |
| gcccctcctt | gaccttccac | caccgtcccc | acagatggtt ttcgtgactg caagaagggg | 840 |
| gatcccaagc | acgggaagcg | gaaacgaggc | cggcccgaa agctgagcaa agagtactgg | 900 |
| gactgtctcg | agggcaagaa | gagcaagcac | ggtgagctcc gggggcacgt gggtcctccc | 960 | tgcgccgggc tgagcggctt cctggggcac tgcgggttgt tg        1002

<210> SEQ ID NO 13
<211> LENGTH: 315
<212> TYPE: DNA
<213> ORGANISM: Homo sapiens

<400> SEQUENCE: 13
gtatgcttgg ccttttcttt ttcttcttc ttcttttat ttttcgagac agggtctcgc        60
tctgtcaccc aggttagagt gcagtggcac aatcttggct cgctacaacc tctgcctgcc       120
gggttcaagt gattcttgtg cctcagcctc caagtagctg ggattacagg cacctgccac       180
catgcccagc taatttttgt attttagta gagacggggg tttcaccatg ttggctaggc       240
tggtctcgaa ctcctgacct caagtgatcc gcccgcctca gcctcccaaa gtgctggaat       300
tacaggtgtg agcca                                                       315

<210> SEQ ID NO 14
<211> LENGTH: 738
<212> TYPE: DNA
<213> ORGANISM: Homo sapiens

<400> SEQUENCE: 14
ggccggtctc aaactcctgg cctcaaatga ctctcctgcc tcggcctctc aaagtgctgg        60
gattacaggt gtgagccagt atgcttggcc ttttcttttt tcttcttctt ctttttattt       120
ttcgagacag ggtctcgctc tgtcacccag gttagagtgc agtggcacaa tcttggctcg       180
ctacaacctc tgcctgccgg gttcaagtga ttcttgtgcc tcagcctcca agtagctggg       240
attacaggca cctgccacca tgcccagcta attttgtat ttttagtaga cggggtt         300 tcaccatgtt ggctaggctg gtctcgaact cctgacctca agtgatccgc ccgcctcagc       360
ctcccaaagt gctggaatta caggtgtgag ccaccgtgcc cagctccctg gccttaaaag       420
tcatgtaatt taatgatcag accccagtca cagccatagg atacaaagaa gcaaaggcaa       480
agagccctgt gtcctgggca cggttacagg ccagtgtagg gaaagagctt ctgcttgcca       540
gtgtgaagaa cagaggagtt taggaagtgt gagtcaggct cagcttagtc aggcagagac       600
cagtgggcat gggttacctg ggggtaacgc gggccaggtg ggcgggctgg cagcctgggg       660
cccatttcct gccaaagcac ctctgaccat ccttctcttc acccaggtac tactacaaac       720
gggagatcct ggaacggg                                                    738

<210> SEQ ID NO 15
<211> LENGTH: 135
<212> TYPE: DNA
<213> ORGANISM: Homo sapiens

<400> SEQUENCE: 15
ctccgccact ccggtaggat tccccgcctg tcattcccta gcccagctct tgggaaactg        60
cagaggggtc cagaggattt gcagttctga acctgcacac tccagtctag gatctccgag       120
caagagcgta gcctc                                                       135

<210> SEQ ID NO 16
<211> LENGTH: 20
<212> TYPE: DNA
<213> ORGANISM: Artificial
<220> FEATURE:
<223> OTHER INFORMATION: primer -continued

```
<400> SEQUENCE: 16
cctgtccact gactccagtg                                              20

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17
acttggccac agcatgcag                                               19

<210> SEQ ID NO 18
<211> LENGTH: 27
<212> TYPE: DNA
<213> ORGANISM: Artificial
<220> FEATURE:
<223> OTHER INFORMATION: primer

<400> SEQUENCE: 18
accaaaggcc atgcggaggc cagagaa                                      27

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
caacaacccg cagtgcccca ggaagccc                                     28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
gcagggctgg ctggccttgg gtgagagg                                     28

<210> SEQ ID NO 21
<211> LENGTH: 27
<212> TYPE: DNA
<213> ORGANISM: Artificial
<220> FEATURE:
<223> OTHER INFORMATION: primer

<400> SEQUENCE: 21
cttgcagcgc ccagaggcac ccacctg                                      27

<210> SEQ ID NO 22
<211> LENGTH: 25
<212> TYPE: DNA
<213> ORGANISM: Artificial
<220> FEATURE:
<223> OTHER INFORMATION: primer

<400> SEQUENCE: 22
gctacctggc ggaactggat ttctc                                        25

<210> SEQ ID NO 23
<211> LENGTH: 25
```

<212> TYPE: DNA
<213> ORGANISM: Artificial
<220> FEATURE:
<223> OTHER INFORMATION: primer

<400> SEQUENCE: 23
cgcttgcgtc gtacttgttc ttctc                                               25

<210> SEQ ID NO 24
<211> LENGTH: 26
<212> TYPE: DNA
<213> ORGANISM: Artificial
<220> FEATURE:
<223> OTHER INFORMATION: primer

<400> SEQUENCE: 24
aagacgcagg ttctggactg gatcag                                              26

<210> SEQ ID NO 25
<211> LENGTH: 24
<212> TYPE: DNA
<213> ORGANISM: Artificial
<220> FEATURE:
<223> OTHER INFORMATION: primer

<400> SEQUENCE: 25
tgggatccag gtccacgtca cttc                                                24

<210> SEQ ID NO 26
<211> LENGTH: 25
<212> TYPE: DNA
<213> ORGANISM: Artificial
<220> FEATURE:
<223> OTHER INFORMATION: primer

<400> SEQUENCE: 26
tcctcagact ccggtggaag tgacg                                               25

<210> SEQ ID NO 27
<211> LENGTH: 25
<212> TYPE: DNA
<213> ORGANISM: Artificial
<220> FEATURE:
<223> OTHER INFORMATION: primer

<400> SEQUENCE: 27
ccggctcagc ttctcgtagg tcatg                                               25

<210> SEQ ID NO 28
<211> LENGTH: 25
<212> TYPE: DNA
<213> ORGANISM: Artificial
<220> FEATURE:
<223> OTHER INFORMATION: primer

<400> SEQUENCE: 28
agctcaacga gggcctcatg aagtg                                               25

<210> SEQ ID NO 29
<211> LENGTH: 26
<212> TYPE: DNA
<213> ORGANISM: Artificial
<220> FEATURE:
<223> OTHER INFORMATION: primer

<400> SEQUENCE: 29

-continued

```
tcccaggacg atggctgaca atacac                                       26

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30
ccccagccat gtacgttgct atcc                                         24

<210> SEQ ID NO 31
<211> LENGTH: 24
<212> TYPE: DNA
<213> ORGANISM: Artificial
<220> FEATURE:
<223> OTHER INFORMATION: primer

<400> SEQUENCE: 31
gcctcagggc agcggaaccg ctca                                         24

<210> SEQ ID NO 32
<211> LENGTH: 28
<212> TYPE: DNA
<213> ORGANISM: Artificial
<220> FEATURE:
<223> OTHER INFORMATION: primer

<400> SEQUENCE: 32
cctgtgtcca ggagtacact agatcatc                                     28

<210> SEQ ID NO 33
<211> LENGTH: 22
<212> TYPE: DNA
<213> ORGANISM: Artificial
<220> FEATURE:
<223> OTHER INFORMATION: primer

<400> SEQUENCE: 33
agaggcaagg gtctctacgt tg                                           22

<210> SEQ ID NO 34
<211> LENGTH: 22
<212> TYPE: DNA
<213> ORGANISM: Artificial
<220> FEATURE:
<223> OTHER INFORMATION: primer

<400> SEQUENCE: 34
tccctggcct taaaagtcat gt                                           22
```

ELF3 GENE COMPOSITIONS AND METHODS

CROSS-REFERENCE TO RELATED APPLICATION

This is a U.S. National Phase of PCT Application No. PCT/US2003/037200, Nov. 21, 2003, which claims the benefit of U.S. Provisional Application No. 60/428,335, filed Nov. 22, 2002.

BACKGROUND (1) Field of the Invention

The present invention generally relates to methods and compositions useful for determining whether a patient has cancer or is at risk for cancer. More specifically, the invention relates to ELF3 gene compositions that are associated with cancer, particularly breast cancer, and methods using those compositions in cancer diagnosis.

(2) Description of the Related Art

References Cited

Al-sumidaie A. M., Leinster S. J., Hart C. A., Green C. D., and McCarthy K. Particles with properties of retroviruses in monocytes from patients with breast cancer. Lancet 1:5-9, 1988.

Altschul, S. F., Gish, W., Miller, W., Myers, E. W. and Lipman, D. J. Basic local alignment search tool. J. Mol. Biol. 215:403-410, 1990.

Altschul, S. F., Madden, T. L., Schäffer, A. A., Zhang, J., Zhang, Z., Miller, W. and Lipman, D. J. Gapped BLAST and PSI-BLAST: a new generation of protein database search programs. Nucleic Acids Res. 25:3389-3402, 1997.

Andersson I. Breast cancer screening in Malmo. Recent Results Cancer Res. 90:114-6, 1984

Andreoli, J. M., Jang, S. I., Chung, E., Coticchia, C. M., Steinert, P. M., and Markova, N. G. The expression of a novel, epithelial-specific Ets transcription factor is restricted to the most differentiated layers in the epidermis. Nucleic Acids Res. 25: 4287-4295, 1997.

Ausubel M. F., Brent R., Kingston E. R., Moore D. D., Seidman J. G., Smith A. J., Struhl K. Current Protocols in Molecular Biology pp. Unit 4.1 Preparation of Cytoplasmic RNA from Tissue Culture Cells, John Wiley & Son Inc., 1995.

Barnes D. M., Bartkova J., Camplejohn R. S., Gullick W. J., Smith P. J., and Millis R. R. Overexpression of the c-erbB-2 oncoprotein: Why does this occur more frequently in ductal carcinoma in situ than in invasive mammary carcinoma and is this of prognostic significance? Eur J Cancer 28:644-648, 1992.

Beghini, A., Ripamonti, C. B., Peterlongo, P., Roversi, G., Cairoli, R., Morra, E. and Larizza, L. RNA hyperediting and alternative splicing of hematopoietic cell phosphatase (PTPN6) gene in acute myeloid leukemia. Hum. Mol. Genet. 22:2297-2304, 2000.

Bonnet M., Guinebretiere J.-M., Kremmer E., Grunewald V., Benhamou E., Contesso G. and Joab I. Detection of Epstein-Barr Virus in invasive breast cancers. J Natl Cancer Inst 91:1376-1381, 1999.

Bittner J. J. The milk influence of breast cancer in mice Science 95: 462-463, 1942 Brembeck F. H., Opitz O. G., Libermann T. A., and Rustgi A. K. Dual function of the epithelial specific Ets transcription factor, ELF3, in modulating differentiation. Oncogene 19: 1941-1949, 2000

Chang, C—H., Scott, G. K., Kuo, W-L., Xiong, X., Suzdaltseva, Y., Park, J. W., Sayre, P., Erny, K., Collins, C., Gray, J. W., and Benz, C. C. ESX: A Structurally unique Ets overexpressed early during human breast tumorigenesis. Oncogene, 14: 1617-1622, 1997.

Chang, C-H., Scott, G. K., Baldwin, M. A. and Benz, C. C. Exon 4-encoded acidic domain in the epithelium-restricted Ets factor, ESX, confers potent transactivating capacity and binds to TATA-binding protein (TBP). Oncogene, 18: 3682-3695, 1999.

Chang J., Lee C., Hahm K.-B., Youngsuk Y., Choi S.-G., and Kim S.-J. Over-expression of ERT (ESX/ESE/ELF3), an Ets-related transcription factor, induces endogenous TGF-b signaling pathway in Hs578t human breast cancer cells. Oncogene 19:151-154, 2000.

Chang, Y., Cesarman, E., Pessin, M. S., Lee, F., Culpepper, J., Knowles, M. D. and Moore, P. S. Identification of herpesvirus-like DNA sequences in AIDS-associated Kaposi's sarcoma. Science 266: 1865-1869, 1994.

Cheung P., Ellison K. S., Verity R., and Smiley J. R. Herpes Simplex virus ICP27 induces cytoplasmic accumulation of unspliced polyadenylated a-Globin pre-mRNA in infected He La cells. J. Virology 74:2913-2919, 2000

Choi, S. G., Yi, Y., Kim, Y. S., Kato, M., Chang, J., Chung, H-W., Hahm, K-B., Yang, H-K., Rhee, H. H., Bang, Y-J. and Kim, S-J. A novel Ets-related transcription factor, ERT/ESX/ESE-1, regulates expression of the transforming growth factor-beta type II receptor. J. Biol. Chem. 273: 110-117, 1998.

Cooper, D. L. Retention of CD44 introns in bladder cancer: understanding the alternative splicing of Pre-mRNA opens new insights into the pathogenesis of human cancers. J. Path. 177:1-3, 1995

Cramer, P., Srebrow, A., Kadener, S., Werbajh, S., De La Mata, M., Melen, G., Nogues, G. and Kornblihtt, A. R. Coordination between transcription and pre-mRNA processing. FESE Let. 498:179-182, 2001.

Cullen B. R. Retroviruses as Model Systems for the Study of Nuclear RNA Export Pathways. Virology 249:203-210, 1998

Darnell, J., Lodish, H. and Baltimore, D. RNA synthesis and processing in eukaryotes. Chapter 8, pp. 261-313 in Molecular Cell Biology $2^{nd}$ ed. Scientific American Books Inc. 1997.

Don, R. H., Cox, P. T., Wainwright, B. J., Baker, K. and Mattick, J. S. 'Touchdown' PCR to circumvent spurious priming during gene amplification. Nucleic Acids Res. 19: 4008, 1995.

Ellison K. S., Rice S. A., Verity R., and Smiley J. R. Processing of a-Globin and ICP0 mRNA in cells infected with Herpes Simplex virus type 1 ICP27 Mutants. J. Virology 74:7307-7319, 2000.

Fan H. Retroviruses and Their role in Cancer. Ch. 7, Vol. 3 The Retroviridae. Plenum Press, New York and London pg. 344-7, 1994.

Favaro J P, and Arrigo S. J. Characterization of Rev Function Using Subgenomic and Genomic constructs in T and COS Cells. Virology 228:29-38, 1997.

Flint S. J., Enquist L. W., Krug R. M, Racaniello V. R, and Skalka A. M. Processing of viral pre-mRNA. Chapter 10, pp. 353-358 in Principles of Virology: Molecular Biology, Pathogenesis and Control. ASM Press, Washington D.C., 2000.

Fluck M. M., Haslam S. Z. Mammary tumors induced by polyomavirus. Breast Cancer Res. 39:45-56, 1996.

Fonseca R, Hartmann L C, Petersen I A, Donohue J H, Crotty T B, Gisvold J J. Ductal Carcinoma In Situ of the Breast. Ann Intern Med 127:1013-1022, 1997.

Gallo R. C., Salahuddin S. Z., Popovic M., Shearer G. M., Kaplan M., Haynes B. F., Palker T. J., Redfield R., Oleske J., Safai B, White G., Foster P., and Markham P. D. Frequent detection and isolation of cytopathic retroviruses (HTLV-III) from patients with AIDS and at risk for AIDS. Science 224: 500-503, 1984.

Gazdar A. F., Kurvari V., Virmani A., Gollahon L., Sakaguchi M., Westerfield M., Kodagoda D., Stasny V., Cunningham H. T., Wistuba I. I., Tomlinson G., Tonk V., Ashfaq R., Leitch A. M., Minna J. D., and Shay J. W. Characterization of paired tumor and non-tumor cell lines established from patients with breast cancer. Int. J. Cancer 78: 766-774. 1998.

Gish, W. and States, D. J. Identification of protein coding regions by database similarity search. Nature Genet. 3:266-272, 1993.

Goodison, S., Yoshida, K., Churchman, M., and Tarin D. Multiple intron rentention occurs in tumor cell CD44 mRNA processing. Am. J. Pathol. 153:1221-1228, 1998.

Guldberg, P., thor Straten, P., Ahrenkiel, V., Seremet, T. Kirkin, A. F. and Zeuthen, J. Somatic mutation of the Peutz-Jeghers syndrome gene, LKB1/STK11, in malignant melanoma. Oncogene 18:1777-1780, 1999

Hastings M. L, Krainer A. R. Pre-mRNA splicing in the new millennium. Curr Opin Cell Biol (United States) 13:302-9, 2001.

Hellwinkel, O. J-C., Holterhus, P-M., Struve, D., Marschke, C., Homburg, N. and Hiort, O. A unique exonic splicing mutation in the human androgen receptor gene indicates a physiologic relevance of regular androgen receptor transcript variants. J. Clin. Endocrinol. Metab. 86:2569-75, 2001.

Hide, W. A., Babenko, V. N., van Heusden, P. A., Seoighe, C. and Kelso, J. F. The contribution of exon-skipping events on chromosome 22 to protein coding diversity. Genome Res. 11:1848-53, 2001.

Hubank, M., and Schatz, D. G. Identifying differences in mRNA expression by representational difference analysis of cDNA. Nucleic Acids Res. 22:5640-5648, 1994.

Keydar, I., Ohno, T., Nayak, R., Sweet, R., Simoni, F., Weiss, F., Karby, S., Mwsa-Tejada, R. and Spiegelman, S. Properties of retrovirus-like particle produced by a human breast cancer cell line: immunological relationship with mouse mammary tumor virus proteins. Proc. Natl. Acad. Sci. USA 81:4188-4192, 1984.

Kienzle N., Young D. B., Liaskou D., Buck M., Greco S., and Sculley T. B. Intron Retention May Regulate Expression of Epstein-Barr Virus Nuclear Antigen 3 Family Genes. J Virology 73:1195-1204, 1999.

Kim, J-H. et al. J Biol. Chem. 277:17520-17530, 2002.

Krug, R. M. The regulation of export of mRNA from nucleus to cytoplasm. Curr. Opin. Cell Biol. 5:944-949, 1993.

Labat, M. L. Possible retroviral etiology of human breast cancer. Biomed and Pharmacother. 52:6-12, 1998.

Lisitsyn, N., Lisitsyn, N., and Wigler, M. Cloning the difference between two complex genomes. Science 259: 946-951, 1993.

Lisitsyn, N. A., Lisistina, N. M., Dalbagni, G., Barker, P., Sanchez, C. A., Gnarra, J., Linehan, W. M., Reid, B. J. and Wigler M. H. Comparative genomic analysis of tumors: Detection of DNA losses and amplification. Proc. Natl. Acd. Sci. USA 92: 151-155, 1995.

Ma, Y. et al. Oncogene 22:4924-2932, 2003.

Matsumoto, K., Wassarman K. M. and Wolffe A. P. Nuclear history of a pre-mRNA determines the translational activity of cytoplasmic mRNA. EMBO J. 17:2107-2121, 1998.

Matsumura, Y., Sugiyama, M., Matsumura, S., Hayle, A. J., Robinson, P., Smith, J. C. and Tarin, D. Unusual retention of introns in CD44 gene transcripts in bladder cancer provides new diagnostic and clinical oncological opportunities. J. Path. 177:11-20, 1995.

Moore, D. H., Charney, J., Kramarsky, B., Lasfargues, E. Y. and Sarkar, N. H. Search for a human breast cancer virus. Nature 229:611-615, 1971.

Nakai, K. and Sakamoto, H. Construction of a novel database containing aberrant splicing mutations of mammalian genes. Gene 141:171-177, 1994.

Nishizawa, T., Okamoto, H., Konishi, K., Yoshizawa, H., Miyakawa, Y. and Mayumi, M. A novel DNA virus (TTV) associated with elevated transaminase levels in posttransfusion hepatitis of unknown etiology. Biochem. and Biophys. Commun. 241: 92-97, 1997.

Oettgen, P., Carter, K. C., Augustus, M., Barcinski, M., Boltax, J., Kunsch, C. and Libermann, T. A. The novel epithelial-specific Ets transcription factor gene ESX maps to human chromosome 1q32.1. Genomics 45:456-457, 1997a.

Oettgen, P., Alani, R. M., Barcinski, M. A., Brown, L., Akbarali, Y., Boltax, J., Kunsch, C., Munger, K., and Liberman, T. A. Isolation and characterization of a novel epithelium specific transcription factor, ESE-1, a member of the Ets family. Mol. Cell. Biol. 17: 4419-4433, 1997b.

Oettgen, P., Barcinski, M., Boltax, J., Stolt, P., Akbarali, Y. and Libermann, T. A. Genomic organization of the human ELF3 (ESE-1/ESX) gene, a member of the Ets transcription factor family, and identification of a functional promoter. Genomics 55: 358-362, 1999.

Piedrafita F. J., Molander R. B., Vansant, G, Orlova E. A., Pfahl M., and Reynolds W. F. An Alu Element in the myeloperoxidase promotor contains a composite SP1-thyroid hormone-retinoic acid response element. J Biol. Chem. 271: 14412-14420, 1996.

Pogo B. G. and Holland J. F. Possibilities of a viral etiology for human breast cancer. A review. Biol Trace Elem. Res. 56:131-142, 1997.

Poiesz B. J., Ruscetti F. W., Gadzar A. F., Bunn P. A., Ninna J. D., and Gallo R. C. Detection and isolation of type C retrovirus particles from fresh and cultured lymphocytes of a patients with cutaneous T-cell lymphoma. Proc. Natl Acad Sci USA 77:7415-7419, 1980.

Raynor M. et al. BMC Cancer 2:1-14, 2002.

Rohlfs E. M., Puget N., Graham M. L., Weber B. L., Garber J. E., Skrzynia C., Halperin J. L., Lenoir G. M., Silverman L. M., and Mazoyer S. An Alu-mediated 7.1 kb deletion of BRCA1 exons 8 and 9 in breast and ovarian cancer families that results in alternative splicing of exon 10. Genes Chromosomes Cancer 28(3):300-7, 2000.

Rosen P. P. Pages 249-343, Chapters 13, 14, 15 in Rosen's Breast Pathology Second Edition Lippincott Williams and Wilkins, Philadelphia, 2001a.

Rosen P. P. Lobular Carcinoma In Situ and Atypical Lobular Hyperplasia. Pages. 581-626, Chapters 33 in Rosen's Breast Pathology Second Edition. Lippincott, Williams and Wilkins, Philadelphia, 2001b.

Roux K. H. Optimization and troubleshooting in PCR. PCR Methods Appl. 4: 5185-5195, 1995.

Roy-Engel A. M., et al. Alu insertion polymorphisms for the study of human genomic diversity. Genetics 159:279-290, 2001.

Schmid C. W. Does SINE evolution preclude Alu function? Nucl. Acid Res. 26:4541-4550, 2000.

Sigfusson B. F., Anderson I, Aspergren K et al. Clustered breast calcifications. Acta Radiol 24:373-381, 1983.

Stella A., Wagner A., Shito K., Lipkin S. M., Watson P., Guanti G., Lynch H. T., Fodde R. and Liu B. nonsense mutation in MLH1 causes exon skipping in three unrelated HNPCC families. Cancer Res. 61:7020-4, 2001.

Stutz F. and Rosbash M. Nuclear RNA export. Genes Devel. 12:3303-3319, 1998.

Szmulewicz M. N., Novick G. E., and Herrera R. J. Effects of Alu insertions on gene function. Electrophoresis 19:1260-1264, 1998.

Tabar L, Akerlund E, Gad A. Five-year experience with single-view mammography randomized controlled screening in Sweden. Recent Results Cancer Res. 90:105-113, 1984.

Tymms M. J., Ng A. Y. N., Thomas, R. S., Schutte, B. C., Zhou, J., Eyre, H. J., Sutherland, G. R., Seth, A., Rosenberg, M., Papas, T., Debouck, C., and Kola, I. A novel epithelial-expressed Ets gene, ELF3: human and murine cDNA sequences, murine genomic organization, human mapping to 1q32.2 and expression in tissues and cancer. Oncogene 15:2449-2462, 1997.

Vansan G., and Reynolds W. F. The consensus sequence of a major Alu subfamily contains a functional retinoic acid response element. Proc Natl Acad Sci USA 92:8229-8233, 1995.

Verbeek A L M, Hendriks J H C L, Holland R. et al. Reduction of breast cancer mortality throuugh mass screening with modern mammography: first results of the Nijmegen Project. 1975-81. Lancet 1:1222-1224, 1984.

Wang Y., Holland J. F., Bleiweiss I. J., Melana S., Liu X., Pelisson I., Cantarella A., Stellrecht K., Manis S. and Pogo B. G. Detection of mammary tumor virus env gene-like sequence in human breast cancer. Cancer Res. 55:5173-5179, 1995.

Wang Y., Go V., Holland J. F., Melana S. M. and Pogo B. G. Expression of mouse mammary tumor virus-like env gene sequences in human breast cancer. Clin Cancer Res 4:2565-256. 1998.

Wellings S R, Jensen H M, Marcum R G. An atlas of subgross pathology of the human breast with special reference to possible precancerous lesions. J. Natl Cancer Inst. 55:231-275, 1975.

Yoshida, K., Bolodeoku, J., Sugino, T., Goodison, S., Matsumura, Y., Warren B. F., Toge, T., Tahara, E. and Tarin, D. Abnormal retention of intron 9 in CD44 gene transcripts in human gastrointestinal tumors. Cancer Res. 55:4273-4277, 1995.

Yuan, L., Shan, J., De Risi, D., Broome, J., Lovecchio, J., Gal, D., Vinciguerra, V., and Xu, H. P. Isolation of a novel gene, TSP50, by a hypomethylated DNA fragment in human breast cancer. Cancer Res. 59:3215-3221, 1999.

U.S. Pat. No. 6,326,173.
U.S. Pat. No. 6,436,909.

The diagnosis of breast cancer requires great skill by pathologists to properly classify biopsies into current pathological groupings. The proper interpretation of pathological findings has great consequences to patients as it can determine the choice of treatment for primary cancer. However, there remains confusion about the relationship between different forms of breast cancer. For example, there is uncertainty as to how invasive lobular cancer is different from invasive duct carcinoma. It is also not known whether all forms of invasive duct carcinoma are the same.

In spite of burgeoning molecular genetic technology and widespread human genome sequence information, no unique genetic marker has been found for the most common forms of breast cancer. The BRCA I and II genes have been useful in identifying patients at risk for familial forms of breast and ovarian cancer, but only a small percentage of most breast cancers occur in patients with the BRCA abnormalities. BRCA genes can be tested from DNA isolated from peripheral blood but this technology is not offered routinely to most women with breast cancer. Gene chip technology allows scientists to look for overexpression or underexpression of otherwise normal genes. Studies with gene chips are beginning to reveal various patterns of gene expression in breast cancer cells that do not occur with normal cells. However, gene chip technology is complex and expensive and is currently performed on actual biopsy tissue, which is not always available.

Another genetic marker, the ELF3 gene, is overly expressed in intraductal carcinoma (also called ductal carcinoma in situ [DCIS]). The ELF3 protein belongs to the Ets family of transcription factors, which contain a helix-loop-helix motif that is required to bind in the major groove of DNA sequences centered over a conserved core GGAA/T motif, and which is important for HER2/neu function (Chang et al., 1997; Oettgen et al., 1997a; Tymms et al., 1997; Andreoli et al., 1997; Choi et al., 1998; Chang et al., 1999; Oettgen et al., 1999; Oettgen et al., 1997b).

The ELF3 gene, which has also been called ESE-1, ERT, jen, and ESX, is a member of the subfamily of ELF (E74-like-factor) genes. The human ELF3 gene contains 9 exons and 8 introns (Chang et al., 1999; Oettgen et al., 1999), is located on chromosome 1q32.1-32.2 (Oettgen et al., 1997a; Tymms et al., 1997), and its transcribed RNA product is ~5.8 kb. It is thought to be expressed only in epithelial cells (Chang et al., 1997; Tymms et al., 1997; Brembeck et al., 2000) and its expression is induced during epidermal differentiation. The epithelial-specific expression pattern of ELF3 is unique among members of the Ets family, and to date very few epithelial-specific transcription factors have been identified. Its DNA-binding domain, conserved among all Ets family members, is located in exons 8 and 9 (Oettgen et al., 1999).

As a transcriptional regulatory gene, ELF3 overexpression or alteration may play a role in carcinogenesis. ELF3 mRNA is overexpressed in ductal carcinoma in situ (DCIS) (Id.) in which there is a high incidence of HER2-neu amplification and overexpression (Barnes et al., 1992). Excess chromosome 1 is common in breast cancer (as well as lung and prostate cancer), and ELF3 may be similarly amplified.

Currently, it is believed that DCIS is the precursor lesion of invasive duct carcinoma (Rosen, 2001a). DCIS apparently arises from the terminal duct-lobular unit where the cell of origin is believed to be a terminal ductal epithelial cell (Rosen, 2001a, Wellings, 1975). Many different forms of DCIS exist including comedo, cribiform, micropapillary and solid type (Rosen, 2001a). Diagnoses of these forms of DCIS have been increasing in part because mammography has played an increasingly major role in detecting these often non-palpable tumors. As many as 43% of tumors detected mammographically have been DCIS (Andersson, 1984; Sigfusson et al., 1983; Tabar et al., 1984; Verbeek et al., 1984; Fonseca et al., 1997). Invasive duct carcinoma is believed to occur when the ductal carcinoma cells breech the myoepithelial basement membrane and invade into the stroma. Invasive duct carcinoma is often found in conjunction with a DCIS lesion (Rosen, 2001a).

DCIS is generally distinctly different from lobular carcinoma which can also form both in situ-like lesions (lobular carcinoma in situ) and invasive lesions (invasive lobular carcinoma). Lobular carcinoma in situ arises from the lobular cell itself (Rosen, 2001b). Most authorities do not consider lobular carcinoma in situ as a neoplastic lesion but as an indicator of increased cellular activity. This increased cellular activity is associated with an increased risk of other forms of breast cancer notably DCIS and invasive duct carcinoma as well as invasive lobular carcinoma. Some authorities feel, however, that lobular carcinoma in situ is the precursor lesion of invasive lobular carcinoma. Lobular carcinoma in situ lesions are inconspicuous and non-palpable, are often multicentric, can form signet ring-like cells and are associated with a distinctive type of infiltration (Rosen, 2001a). Mucin can be seen in an intracytoplasmic location in these cells. C-adherins are absent from these lesions. The cellular origin of these lesions is presumed to be the lobular cell.

Currently there is no genetic marker present that distinguishes lesions of terminal duct origin from those of lobular origin. In biopsy material from neoplastic breast lesions, these different cancers can be distinguished using some stains of mucin, cytokeratin and C-adherin, but there is no useful genetic marker that distinguishes these different cancers.

There is thus a need for new genetic markers to identify breast cancer, particularly DCIS. The present invention provides such markers.

SUMMARY OF THE INVENTION

Accordingly, the present invention is based on the discovery of an association between cancer and novel ELF3 gene and/or ELF3 message (mRNA) sequences. The novel sequences include intron retention in the mRNA, a novel Alu sequence in the ELF3 gene and a novel 5' untranslated region (UTR) in the ELF3 gene.

Thus, in some embodiments, the present invention is directed to cDNAs of a human ELF3 gene. In these embodiments, the cDNAs comprise an intron of the ELF3 gene or a portion of an intron of the ELF3 gene. Vectors comprising the cDNA and cells transfected with those vectors are also envisioned.

In other embodiments, the invention is directed to sets of two primers useful for amplifying any of the ELF3 sequences associated herein with cancer, e.g., mRNA retaining an ELF3 intron, $Alu_{kwd}$, and the novel 5' UTR described herein.

The present invention is additionally directed to isolated nucleic acids or mimetics comprising a sequence homologous to at least a portion of an intron of a human ELF3 gene.

The invention is also directed to isolated nucleic acids or mimetics comprising a sequence at least 95% homologous to SEQ ID NO:13 or SEQ ID NO:15.

Vectors comprising any of the above nucleic acids or mimetics, and cells comprising those vectors, are also within the scope of the invention.

Additionally, the invention is directed to probes comprising any of the above nucleic acids or mimetics. In these embodiments, the probes further comprise a detectable label.

In additional embodiments, the invention is directed to pairs of cell cultures, where each cell culture is of the same tissue type and is derived from cancerous mammalian tissue, and where one of the cell lines is of cancerous cells and the other cell line is of matched noncancerous cells.

The present invention is also directed to methods for determining whether a patient has cancer or is at risk for cancer. The methods comprise evaluating whether a cell in the patient comprises an ELF3 nucleic acid sequence disclosed herein to be associated with cancer. These sequences include an ELF3 mRNA retaining at least a portion of an intron, SEQ ID NO: 15, and an $Alu_{kwd}$.

The invention is additionally directed to kits for evaluating whether a patient has cancer or is at risk for cancer. These kits comprise sets of two primers homologous to a portion of an ELF3 gene. The primers are useful for determining whether the patient comprises a nucleic acid sequence described herein as associated with cancer. These sequences include ELF3 mRNA retaining at least a portion of an intron, the novel ELF3 gene 5' UTR, and $Alu_{kwd}$. The kits also comprise instructions directing the use of the primers for determining whether a nucleic acid sequence amplified by the primers is present in a nucleic acid preparation.

In related embodiments, the invention is directed to additional kits for evaluating whether a patient has cancer or is at risk for cancer. These kits comprise probes useful for determining whether the patient comprises a nucleic acid sequence described herein as associated with cancer. These sequences include ELF3 mRNA retaining at least a portion of an intron, the novel ELF3 gene 5' UTR, and $Alu_{kwd}$. The kits also comprise instructions directing the use of the probe for determining whether a nucleic acid sequence homologous to the probe is present in a nucleic acid preparation.

In additional embodiments, the invention is directed to methods for determining whether a cell or other sample comprises a virus. The methods comprise adding contents of the cell or adding a portion of the sample to a culture, where the culture comprises a susceptible cell that is capable of acquiring a particular characteristic upon infection with a virus. The particular characteristic can be intron retention of ELF-3 mRNA and/or acquisition of $Alu_{kwd}$ in an ELF3 gene. The methods further comprise determining whether the susceptible cell has acquired the characteristic after addition of the contents of the cell.

BRIEF DESCRIPTION OF THE DRAWINGS

FIG. 1 shows results from experiments relating to genomic DNA Southern blots for probe GC3. Panel A shows a Southern blot using probe GC3 with 5 μg of HpaII and MspI digested genomic DNA prepared from K151 breast cancer cell cultures (lane T) and normal cell lines from the same effusion (lane N). The GC3 probe only hybridized to tumor genomic DNA, but not to normal amplicon DNA with either HpaII or MspI digestion. Panel B shows the Hpa II or Msp I digested tumor (lane T) and normal (lane N) genomic DNA electrophoresis before transfer to the blot membrane for GC3 probe treatment, which served as the DNA digestive and quantitative control.

FIG. 5 shows gels of electrophoresed PCR products showing that the 202 bp GC3 product was abolished by RNase digestion of isolated mRNA, but not by DNase I digestion. Total cellular RNA prepared from K151 tumor cell lines was subjected to DNase I (lane D) and RNase (lane R) digestion before cDNA synthesis. RT-PCR was performed using GC3 primers. The 202 bp GC3 product was produced on the DNase I-digested RNA isolate but not on RNase-digested RNA isolate. The result verified that the 202 bp GC3 is generated by amplification of mRNA; contamination with genomic DNA is excluded.

FIG. 9 shows schematic diagrams illustrating different forms of the ELF3 gene and their relation to cancer. Panel a shows the genomic organization of the human ELF3 gene. Exons 1 to 9 are represented by filled boxes, and the introns in between are represented by lines. Panel b shows where unspliced ELF3 mRNA was found. The entire intron 4, 5 and 6, as determined by 5' RACE, and the GC3 fragment, as determined by RT-PCR, are indicated. The numbers indicate the locations in the genomic sequence. Panel c shows the fully spliced ELF3 mRNA. The exon 1 in the darkened box indicates a different 5' UTR from previously published sequences.

FIG. 20 is a diagram summarizing the result of genomic walking in human ELF3 gene (Panel A) and the location of of the Alu$_{kwd}$ antisense insertion in the ELF3 gene (Panel B). The exons are represented as numbered solid boxes and the introns as thin lines. Panel A. The locations of the exons in the ELF3 gene are labeled as numbers above the exons. The DNA fragments from the genomic upstream and downstream walk are shown as boxes with the library's name inside. The location of the primers used for genomic upstream and downstream walking are indicated as arrows with numbers. Panel B. The 351 bp antisense insertion of Alu$_{kwd}$ is shown as a box with the insertion point indicated by numbers below the box. The location of GC3 and Alu primers are represented as arrows with numbers.

DETAILED DESCRIPTION OF THE INVENTION

Figure 2:
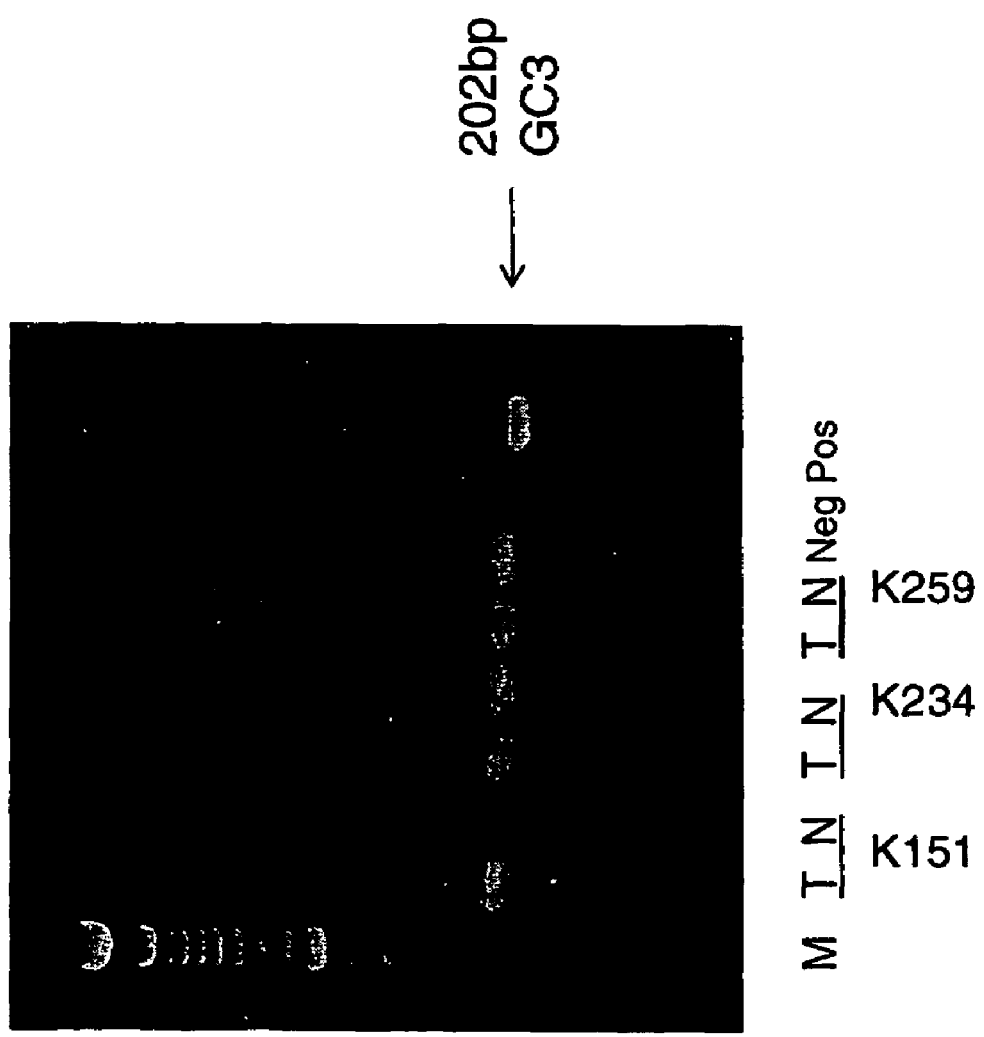
FIG. 2 shows a gel of electrophoresed PCR products establishing the presence of the GC3 202 bp DNA fragment in both breast tumor and normal cell lines. DNA isolations from 3 breast tumor cell lines and matched normal cell lines were amplified by GC3 primers, designed from the GC3 DNA sequence, in PCR reactions. Lane M, 100 bp DNA ladder; lane T and N represent tumor and normal cell lines respectively, GC3 plasmid served as a positive control.

The present invention is based on the discovery of novel ELF3 gene and ELF3 message (mRNA) sequences. The novel sequences include intron retention in the mRNA; a novel Alu sequence in the ELF3 gene and mRNA; and a novel 5' untranslated region (UTR) in the ELF3 gene. These novel sequences, which can be isolated from cancerous tissue biopsies as well as peripheral blood mononuclear cells (PBMCs), are associated with the presence of cancer in a patient having the novel sequences. In particular, the sequences are associated with breast cancer, especially ductal carcinoma in situ (DCIS).

Based on the association between the sequences and cancer, methods which detect the presence of any of the sequences in a patient is useful in the diagnosis of cancer.

While the strongest association of the presence of these sequences is with DCIS, the sequences have also been associated with other cancers, in particular other forms of breast cancer, and methods for detecting other forms of cancer using these sequences are also useful. Nevertheless, the very strong association with DCIS allows one to distinguish DCIS from other forms of breast cancer, with a high probability, using these sequences.

Thus, in some embodiments, the invention is directed to cDNAs of a mammalian ELF3 gene, or fragments thereof at least 20 nucleotides long, which comprise an intron of the ELF3 gene or a portion of an intron of the ELF3 gene. Fragments of the cDNA are preferably longer than 20 nucleotides long, for example at least 50, at least 100, at least 500, or at least 1000 nucleotides long.

As used herein, a cDNA has its common meaning, that is a DNA comprising the sequence of a reverse-transcribed polyA-containing mRNA. This includes amplified products of the reverse-transcribed mRNA, such as products from an RT-PCR procedure. Since a cDNA is a reflection of the mRNA that is present, an ELF3 cDNA that retains an intron of the ELF3 gene indicates that the mRNA has inappropriately retained an ELF3 gene intron, which is associated with cancer, particularly DCIS (See Example 1). An example of a normally spliced ELF3 cDNA (without an intron or portion) is provided as SEQ ID NO:2.

In preferred embodiments, the ELF3 cDNA comprises intron 4, intron 5, intron 6, intron 7, intron 8, portions of any of those introns, or combinations of any of those introns or portions. Introns 4, 5, 6, 7 and 8 of the ELF3 gene can be readily identified by the skilled artisan by consulting public databases such as GenBank, where a human ELF3 gene is provided as Accession AF110184 (SEQ ID NO:1). An amino acid sequence (SEQ ID NO:3), the translation of SEQ ID NO:1 (after mRNA processing), is also provided under Accession AF110184. See Appendix, identifying SEQ ID NO:5, SEQ ID NO:6, SEQ ID NO:7, SEQ ID NO:8 and SEQ ID NO:9 as introns 4, 5, 6, 7 and 8, respectively.

An example of a retained sequence that is associated with cancer is SEQ ID NO:11 (Example 1—also identified therein as GC3), which is present in the mRNA (and derived cDNA) of cancer patients as retained portions of introns 7 and 8.

These embodiments are not limited to any specific ELF3 cDNA or intron sequences such as SEQ ID NO:2, 5, 6, 7, 8, or 9. Rather, homologous sequences from any mammal, or alternative human sequences are also envisioned as within the scope of the invention. The skilled artisan would understand that there could be small variations among ELF3 gene, cDNA, or amino acid sequences between mammals, or among humans. For example, SEQ ID NO:3 and SEQ ID NO:4 provide alternative amino acid sequences resulting from the translated gene provided as SEQ ID NO:1 (starting at nt 5319) and the cDNA SEQ ID NO:2, respectively (see Appendix).

In some aspects of these embodiments, the cDNA or portion also comprises an $Alu_{kwd}$. $Alu_{kwd}$ is a novel Alu sequence that is present as insertions into ELF3 introns in cancerous tissue as well as PBMCs of cancer patients (see Example 2). In particular, $Alu_{kwd}$ is found in breast cancer, especially DCIS.

One example of $Alu_{kwd}$ consists of the sequence provided herein as SEQ ID NO:13. However, based on the understanding that Alu sequences have many variants, such that they can be logically divided into families that are at least about 90%, more preferably 95%, homologous to each other (Roy-Engel et al., 2001), it would be expected that $Alu_{kwd}$ exists as several different sequences that are at least about 90% homologous to each other. It would also be expected that any one of those forms of $Alu_{kwd}$ would be associated with cancer.

In preferred embodiments, the $Alu_{kwd}$ is found in cDNAs of cancer patients within a retained intron 8. In more preferred embodiments, the $Alu_{kwd}$ is between nucleotides 8762 and 8763 using the numbering of SEQ ID NO:1.

In some embodiments, the cDNA of the present invention comprises the entire ELF3 gene coding region, i.e., from the 5' UTR to the polyA tail. In other embodiments, the cDNA consists of only a fragment of the full length coding region, comprising at least 20 nucleotides of the coding region. The latter fragment could be obtained through reverse transcription polymerase chain reaction (RT-PCR) of cellular mRNA or total RNA, using PCR primers that do not amplify the entire coding region. Such methods are well known.

In some preferred embodiments, the cDNA comprises introns 4, 5, 6 and 7 of the ELF3 gene, for example those provided as SEQ ID NO:5, 6, 7 and 8, respectively. In other embodiments, the cDNA comprises the 5' UTR of the ELF3 mRNA. Preferably, the 5' UTR comprises the nucleotide sequence provided herein as SEQ ID NO:15, or a variant of SEQ ID NO:15 that is at least about 90% homologous to SEQ ID NO:15.

A preferred example of a full length cDNA comprising SEQ ID NO:15 is SEQ ID NO:2, where the cDNA is interspersed by one or more introns.

In preferred embodiments, the cDNA of the present invention is prepared from a composition comprising a cell, for example a tissue or blood sample from a patient or from PBMCs. In some of these embodiments, the cell further comprises genomic DNA comprising an $Alu_{kwd}$, for example consisting of SEQ ID NO:13. Preferably, the $Alu_{kwd}$ is between nucleotides 8762 and 8763 of an ELF3 gene in the cell, using the numbering of SEQ ID NO:1.

In other preferred embodiments, the cDNA is prepared from a composition comprising a cell, where the cell is obtained from a patient being tested for breast cancer. Preferably, the patient is at high risk for breast cancer. In these embodiments, the cell composition is preferably a blood or PBMC composition or a biopsy of tissue (preferably breast tissue) or an effusion suspected of being cancerous.

The preparation of the cDNA can utilize any method known in the art. In preferred embodiments, the cDNA is prepared using RT-PCR. Those RT-PCR methods would utilize primers suitable for amplifying at least a portion of an ELF3 gene sequence suspected of being associated with cancer, such as ELF3 intron 4, 5, 6, 7 or 8, an $Alu_{kwd}$, or the novel ELF3 5' UTR identified herein. See Examples.

Included herein as an RT-PCR technique is the nucleic acid sequence-based amplification ("NASBA") method, as described, for example, in U.S. Pat. No. 6,326,173, and references cited therein.

Primers (i.e., a set of two primers) are suitable for amplifying a region of an ELF3 gene when the primers flank the region and allow amplification of that region using PCR. Sequence-specific primers related to a mammalian ELF3 gene, ELF3 mRNA or corresponding cDNA, or to an intron of the ELF3 gene are also useful in methods of detecting target ELF3 sequences by sequencing reactions, as an alternative to PCR-based methods.

The present invention is also directed to vectors comprising any of the above-described cDNAs. As used herein, a vector takes its common molecular biology meaning, that is a piece of nucleic acid capable of replication in a host cell. Preferred examples include plasmid vectors and viral vectors. Such vectors are useful for preserving and increasing the amount of a cDNA in a cell.

In related embodiments, the invention is also directed to cells transfected with any of the above vectors, such that the vector is capable of replication in the cell. Any cell supporting replication of the vector, including prokaryotic and eukaryotic cells, is envisioned as within the scope of these embodiments. Also included are cells where the vector sequence comprising the cDNA is integrated into a chromosome of the cell, or where the vector autonomously replicates in the cell, independent of chromosomal replication.

In other embodiments, the invention is directed to various isolated nucleic acid or mimetic sequences. Each of the sequences is useful for, e.g., determining whether the sequence is present in a sample, for example a PBMC preparation or a biopsy. The sequences are preferably greater than 10 or 20 nucleotides long and less than 50 kB. More preferably, the sequences are less than 12 kB. An example of a useful sequence less than 12 kB is a full length sequence of the ELF3 gene from a patient being diagnosed for cancer, e.g., DCIS. The sequence could be analyzed for the novel 5' UTR or the novel $Alu_{kwd}$ both identified in the experiments discussed in the Examples. In other aspects the sequences are less than 2 kB, or 1 kB, or 500 nt, e.g., to be able to more usefully clone the novel 5' UTR or the novel $Alu_{kwd}$, perhaps with flanking sequences, into a vector to clone into a cell such as an *E. coli* or a mammalian cell. Optionally, the sequences can incorporate a detectable label, to identify the novel 5' UTR, the novel $Alu_{kwd}$, or any intron retained in an ELF3 sequence by hybridization. Many detectable labels are known; the invention is not narrowly limited to any particular type of label. The type of label can be chosen as most appropriate for the particular use being employed. Examples include radioactive, fluorescent, chemiluminescent, an enzyme suitable for use in an enzyme detection system (e.g., alkaline phosphatase or horseradish peroxidase), spin, or hapten labels. The latter are labels that are detected using antibodies that specifically bind to the hapten. A well-known example is digoxigenin.

These sequences can be comprised of DNA, RNA or a mimetic. As used herein, a mimetic is a nucleotide analog that differs chemically from a naturally occurring nucleotide, but that is capable of oligonucleotide-like noncovalent binding to a homologous nucleotide sequence. See, e.g., U.S. Pat. No. 6,436,909 for a discussion of useful mimetics. A preferred example of a useful mimetic is a phosphorothioate mimetic, which are well known.

In some embodiments the nucleic acids or mimetics comprise a sequence homologous to at least a portion of an intron of a human ELF3 gene, and may optionally incorporate a detectable label. These sequences are useful, e.g., for determining if ELF3 mRNA from the sample has retained at least a portion of an intron. In preferred embodiments, the intron to which the nucleic acids or mimetics are homologous is intron 4, intron 5, intron 6, intron 7 or intron 8, exemplified herein as SEQ ID NO:5, 6, 7, 8 or 9, respectively.

In other embodiments, the nucleic acids or mimetics comprise a sequence at least 95% homologous to at least a portion of SEQ ID NO:13, useful, e.g., for determining whether a member of the $Alu_{kwd}$ family is present in either DNA or mRNA from the sample. Preferably, the sequence is completely homologous to SEQ ID NO:13. As with previous embodiments, this sequence can optionally comprise a detectable label. The sequence can also comprise regions of the ELF3 gene where the $Alu_{kwd}$ is expected, for example the regions on either side of nucleotides 8762 and 8763 of the ELF3 gene, regions where $Alu_{kwd}$ inserts (see Example 2).

As used herein, a first sequence is at least 95% homologous to a second sequence when the first sequence is 95% identical to the second sequence or the complement of the second sequence. Where no percentage of homology is used, "homologous" means completely homologous. A sequence, e.g., a primer, is homologous to a longer sequence, e.g., an ELF3 gene, when the sequence has complete identity to a portion of the longer sequence, or its complement.

In still other embodiments, the nucleotide or mimetic sequence is at least 95% homologous to at least a portion of SEQ ID NO:15, indicating that the novel 5' UTR is present in either DNA or mRNA from the sample. Also useful are sequences encoding an ELF3 open reading frame such as SEQ ID NO:3 or SEQ ID NO:4 or their complement, adjoining the 3' end of SEQ ID NO:15.

Also included within the scope of the invention, are vectors comprising any of the nucleic acids described above. Cells transfected with these vectors are also envisioned. These include either prokaryotic and eukaryotic cells, including cells within multicellular organisms that have been transfected with the vectors to determine the effect of the presence of the nucleic acid on the organism.

In related embodiments, the invention is directed to probes which comprise any of the nucleic acid or mimetic sequences described above, further comprising a detectable label, as discussed above.

The sequences described herein as being associated with cancer could also be identified using sets of two primers that are suitable to amplify (e.g., using PCR or RT-PCR) and detect those sequences. Thus, the invention is also directed to sets of two primers, wherein each primer is homologous to a portion of the ELF3 gene. Preferably, the primers are less than about 50 nucleotides in length, more preferably less than about 40 nucleotides in length, and most preferably less than about 30 nucleotides in length.

In some aspects, at least one primer is homologous to a portion of an intron of the ELF3 gene. In these aspects, when the primers are used in a procedure such as RT-PCR, the primers amplify a defined mRNA sequence only if an intron was present in the sequence.

In other aspects, primers that are homologous only to exon sequences are useful if each of the two primers are homologous to different exons. In that situation, the product of amplification would be one size if intron retention was not present in the amplification product, and a larger size if an mRNA, or a portion thereof, that does retain an intron is amplified.

As used herein, a primer is defined as homologous to another nucleotide sequence if that primer is homologous to either strand of the duplex of that sequence, provided the primer is useful when used with another primer in amplification methods. Introns 4, 5, 6, 7, and especially 8 are preferred as targeted by these primers. To determine if $Alu_{kwd}$ is present between nucleotides 8762 and 8763 of the ELF3 gene, one of the primers would be homologous to a region of an ELF3 gene 5' to nt8762 of the ELF3 gene, and the other of the two primers is homologous to a region of the ELF3 gene 3' to nucleotide 8763 of the ELF3 gene.

Other primer sets envisioned herein include sets suitable for amplifying an $Alu_{kwd}$. Examples of such primer sets are those where one or both primer is at least 95% homologous to SEQ ID NO:13, including those where one or both primers are completely homologous to a portion of SEQ ID NO:13. In the embodiments where only one primer is homologous to SEQ ID NO:13, the other primer is preferably homologous to a portion of an ELF3 gene, such as an intron of an ELF3 gene, for example intron 8, identified in Example 2 to harbor an $Alu_{kwd}$.

Additional primer sets envisioned as within the scope of the invention are sets suitable for amplifying an ELF3 5' UTR that is at least 95% homologous to SEQ ID NO:15. Preferably, at least one primer is homologous to SEQ ID NO:13 and the other primer is homologous to an ELF3 gene, for example the 3' end of the open reading frame of an ELF3 gene.

Since it is expected that cancers in any mammal would be associated with the presence of any of the above ELF3 sequences, e.g., mRNAs retaining introns or portions of the ELF3 gene, the novel 5' UTR, and $Alu_{kwd}$, the invention encompasses these sequences from any mammalian species, although in preferred embodiments, the mammal is a human.

Any ELF3 nucleotide sequence, including gene, cDNA, mRNA, primer, and probe sequences, and ELF3 amino acid sequences from any mammal can be readily identified by the skilled artisan as being at least about 80% homologous to the analogous sequences provided herein. More preferably, the variants are at least about 90% homologous; even more preferably about 95% or 99% homologous; and most preferably completely homologous to the sequences provided herein. All human ELF3 gene, cDNA and amino acid sequences would be expected to be at least about 95% homologous to the analogous sequences provided herein. The sequence of any mammalian ELF3 gene, cDNA, or amino acid sequence could be obtained without undue experimentation by well known methods.

Also envisioned as within the scope of the invention are pairs of cell cultures, where both cell cultures are of the same tissue type and are derived from cancerous mammalian tissue, and where one of the cell lines is of cancerous cells and the other cell line is of matched noncancerous cells. Examples include pairs of cell cultures prepared as described in Example 1, for example the pair designated K259.

The invention is also directed to methods for determining whether a patient has cancer or is at risk for cancer. The methods comprise evaluating whether a cell in the patient comprises any of the ELF3 nucleic acid sequences established herein to be associated with cancer. The sequences include those indicating intron retention in an ELF3 mRNA, the novel 5' UTR (exemplified as SEQ ID NO: 15) and an $Alu_{kwd}$ (exemplified herein as SEQ ID NO:13). The methods generally utilize any of the novel primers, probes, or nucleic acid sequences described above. These methods are preferably done with a sample of many cells, for example a PBMC preparation or a tissue biopsy from the patient such as from a breast lesion or lymph node with metastatic cancer or a cancerous effusion. As used herein, a biopsy is the removal of tissue from a patient, including the removal of fluid from effusions, for example breast cancer pleural effusions. The cells in the sample can be of one or more than one cell type.

In some embodiments, these methods utilize primers in a polymerase chain reaction (PCR) to amplify DNA to establish the presence or absence of the tested ELF3 sequence. Reverse transcription of mRNA is also useful in some embodiments to prepare cDNA for PCR, e.g., when determining whether mRNA intron retention is present. See discussion of RT-PCR in the Examples. PCR could also be used without reverse transcriptase, for example when determining whether the novel 5' UTR is present in the genome of the cell. A preferred PCR method is real-time PCR, due to its sensitivity and ability to semi-quantitate the sequence that is amplified. All of the above methods can be utilized with the instant invention without undue experimentation.

In other embodiments, these methods utilize one of the probes described above in northern hybridization. As is well known, northern hybridization generally involves isolation of mRNA from the cell, electrophoresis of the mRNA on a gel, blotting of the gel to transfer the mRNA to a membrane, and treating the membrane with a probe, to determine whether a sequence homologous to the probe is present on the gel and thus in the mRNA of the cell.

Other embodiments of these methods utilize one of the above-described probes in Southern hybridization. As is well known, Southern hybridization generally involves isolation of DNA from the cell, electrophoresis of the DNA on a gel, blotting of the gel to transfer the DNA to a membrane, and treating the membrane with a probe, to determine whether a sequence homologous to the probe is present on the gel and thus in the DNA of the cell.

The invention is also directed to kits for evaluating whether a patient has cancer or is at risk for cancer. The kits of these embodiments comprise at least one set of two primers that are homologous to a portion of an ELF3 gene, wherein the primers are useful for amplifying a nucleic acid sequence established herein to be associated with cancer. As previously discussed, the nucleic acids established herein to be associated with cancer include intron retention in an ELF3 mRNA, the novel ELF3 5' UTRs identified herein (exemplified by SEQ ID NO:15), and an $Alu_{kwd}$ (exemplified herein by SEQ ID NO:13).

These kits also comprise instructions directing the use of the primers for determining whether the nucleic acid sequence is present in a nucleic acid preparation such as an mRNA, cDNA or genomic preparation, as appropriate. These instructions need not be physically associated with the primers, but could refer to the use of the primers from a source physically separated from the primers, e.g., from a web site or a separately mailed paper.

As discussed above in the context of the primers of the invention, when the primers are directed to determining whether there is intron retention in an ELF3 mRNA, at least one primer is homologous to a portion of an intron of the ELF3 gene, or the two primers are homologous to portions of the ELF3 gene that flank an intron of the ELF3 gene.

In related embodiments, the invention is also directed to other kits for evaluating whether a patient has cancer or is at risk for cancer. These kits comprise a nucleic acid sequence and/or probe, as discussed above, which is useful for determining whether a sample has one of the ELF3 gene sequences identified herein as being associated with cancer. These kits also comprise instructions directing the use of the nucleic acid sequence or probe for determining whether a nucleic acid sequence homologous to the probe is present in the sample.

In some embodiments, these kits comprise a gene chip having numerous probes or nucleic acid sequences, for example probes or sequences for each of the retained ELF3 introns and/or $Alu_{kwd}$. Probes or sequences diagnostic for other diseases, e.g., a BRCA I probe, could also be included. Gene chip technology is well known in the art.

In further embodiments, the presence in a sample of one of the ELF3 gene sequences identified herein as being associated with cancer is detected by sequencing RNA, cDNA or DNA of the sample, wherein the sequencing may be accomplished by any of the various sequencing methods known in the art.

The inventors have also discovered that addition of a virus, e.g., Epstein-Barr Virus (EBV), to a cell in culture, for example a BJAB cell, causes ELF3 mRNA intron retention and/or ELF3 $Alu_{kwd}$ appearance. See Example 3. Based on this finding, a cell suspected of harboring a virus that causes ELF3 mRNA intron retention can be easily assayed for presence of a virus.

Thus, the invention is also directed to methods for determining whether a cell comprises a virus. The methods comprise a first step of adding the contents of the cell to a culture, where the culture comprises a susceptible cell that is capable of acquiring a characteristic upon infection with a virus. As disclosed herein, the characteristic is ELF3 mRNA intron retention and/or acquisition of an $Alu_{kwd}$, for example SEQ ID NO:13, in an ELF3 gene. The methods further comprise a second step of determining whether a susceptible cell has acquired either or both of the above characteristics after addition of the contents of the cell. An example of a susceptible cell is a BJAB cell, which is an EBV-negative Burkitt's lymphoma. In preferred embodiments, the virus is related to Epstein-Barr virus, preferably a member of the Herpesviridae, more preferably a member of the Gammaherpesviradae, and most preferably a Lymphocryptovirus.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Unspliced Elf3 Cytoplasmic mRNA in Human Breast Cancer Cells

Example Summary

Using modified representational difference analysis (mRDA), a DNA fragment (denoted GC3) was isolated as a difference between a human breast cancer cell line K151 (tester) and a normal cell line (driver) from the same patient. GC3 proved to be a fragment of intron 7 of the ELF3 gene which appears to be amplified in the K151 breast cancer cell line. The ELF3 gene belongs to the Ets family of transcription factors which are frequently altered in several types of cancer. This intron fragment of the ELF3 gene was expressed in human breast cancer cell lines and 4 of 6 breast cancer tissues but not in matched normal cell lines and normal tissues after testing by reverse transcriptase PCR (RT-PCR). Genomic DNA contamination of RNA isolates was excluded by DNAse I and RNAse digestion analysis. mRNA of GC3 was detected in both nuclear and cytoplasmic RNA fractions of breast cancer cell lines, indicating that intron containing ELF3 mRNA had not been properly spliced prior to export to the cytoplasm of these cancer cells. These findings were verified using the 5' and 3' rapid amplification of cDNA ends (5' RACE and 3' RACE) procedures to search for cDNA sequences in RNA from these cancer cell lines. This revealed the presence of partially unspliced ELF3 mRNA and fully spliced ELF3 mRNA in the same breast cancer cell line. Sequence analysis confirmed that GC3 was indeed retained in cytoplasmic mRNA. Partially unspliced ELF3 mRNA contained introns 4, 5, 6 and 7 without any nucleotide mutation at intron/exon splice junction borders. Fully spliced 1959 bp ELF3 mRNA showed a different 5' UTR from the published ELF3 mRNA, and was predicted to encode a 371 amino acid protein which shared 98% homology to the ELF3 protein sequence. This is the first report of intron retention of ELF3 and/or the pathological appearance of both spliced and unspliced cytoplasmic ELF3 mRNA present simultaneously in human breast cancer cells. The finding that intron 7 of the ELF3 gene is present in breast cancer cells lines and tissues (4 of 6 tested) from breast cancer and not in normal autologous breast tissue and cell lines may be very important in the understanding of the pathogenesis of breast cancer.

Introduction

The search for a viral etiology of human breast cancer has been the subject of numerous investigations, especially since the discovery of a transmissible agent in milk causing breast cancer in mice (Bittner, 1942). Representational difference analysis (RDA) is a recently developed technique (Lisitsyn et al, 1993; Hubank and Schatx, 1994) that has been useful in detecting viral sequences and unique genes. It was instrumental in the discovery of herpes virus 8 (Chang et al., 1994), hepatitis virus TTV (Nishizawa et al., 1997) and the novel gene TSP50 (Yuan et al., 1999). Using a modified RDA (mRDA) technique, this study describes the isolation of a DNA intronic fragment of the ELF3 gene in breast cancer cells which appears to be uniquely retained in the cytoplasmic mRNA in breast cancer cells and cell lines.

Breast cancer cell lines and matched normal cell lines were developed from malignant effusions. DNA from a cancer cell line was used as "tester" and matched normal cell line DNA was used as "driver" in an mRDA method. Two DNA fragments, denoted GC2 and GC3 unique to the cancer DNA, were found. This report focuses on GC3, a 531 bp DNA fragment. This fragment was found to be within intron 7 (bp7514-8045) of the ELF3 gene (Chang et al., 1997; Oettgen et al., 1997b; Tymms et al., 1997; Andreoli et al., 1997; Choi et al., 1998).

In this study, GC3 appeared as a difference between breast cancer and matched normal cells, and is present in the amplicon and genomic DNA Southern blotting of the cancer lines but not the matched controls. In order to determine whether there was transcription of this GC3 intron 7 area, cytoplasmic mRNA was analyzed by reverse transcription polymerase chain reaction (RT-PCR). Using RT-PCR, cDNA was found to be retaining intron 7. This observation was confirmed by application of the 5' and 3' RACE procedure which revealed an ELF3 cDNA sequence including introns 4, 5 and 6 without nucleotide mutation at the intron/exon junctions. In addition to the partially unspliced cDNA, a fully spliced 1959 bp ELF3 cDNA sequence was isolated which was identical to the mRNA of ELF3, and predicted to encode a 371 amino acid protein sharing 98% homology to the ELF3 protein. Although the coding sequence was almost identical to the published ELF3 gene, the 5' UTR was different, and extended from 4976 to 5006 instead of from 4777 to 4888 of the ELF3 nucleotide sequence (Tymms et al., 1997).

Intron retention of the GC3 intronic area was found in the cytoplasm of breast cancer cell lines and in breast cancer tissue and appears as a pathological defect which may be unique to breast cancer. Unspliced ELF3 mRNA in breast cancer suggests altered regulatory pathways in the splicing of ELF3 mRNA. In eukaryotic cells, most cytoplasmic mRNA does not contain unspliced sequences as unspliced nuclear mRNA is enzymatically destroyed in the nucleus after splicing (Darnell et al., 1997; Cramer et al., 2001; Hide et al, 2001; Stutz et al., 1998; Krug, 1993; Hastings and Krainer, 2001). However, retroviruses (Cullen, 1998; Flint et al., 2000; Favaro and Arrigo, 1997) and some herpes viruses (Cheung et al., 2000; Ellison et al., 2000; Kienzle et al., 1999) are able to induce intron retention in mRNA which enables them to use this mechanism to produce different viral proteins (Cullen, 1998; Flint et al., 2000; Favaro and Arrigo, 1997) and allows them to alter the splicing of cellular proteins important to the function of the virus (Cheung et al., 2000; Ellison et al., 2000). The finding of intron retention in the ELF3 gene in breast cancer cells may be an important finding in understanding the pathogenesis of breast cancer and suggests a mechanism to search for a viral cause of breast cancer.

Materials and Methods

Cell Lines. Paired human breast cancer and normal cell lines were established from malignant breast cancer effusions. All effusions were obtained from patients with metastatic breast cancer using an investigational review board approved protocol. Briefly, mononuclear cells from effusions were isolated and cultured in RPMI media (GIBCO-BRL) with 20% fetal bovine serum (FBS)-at 37° C. in a 5% $CO_2$ atmosphere. After 2 to 3 days, non-adherent cells were transferred to another flask and cultured separately. Cells were monitored regularly for morphology and growth characteristics. The adherent cells were passed by trypsinization and diluted 1:2 when adequate growth appeared. Non-adherent cells were also passed at the same dilution. When independent and continuous growth sustained recurrent passage, cytogenetic analysis was performed in the Cell Genetics Laboratory of North Shore University Hospital using standard cytogenetic techniques, which measure chromosome number and morphology. Expression of epithelial glycoprotein (EGP2), a cell surface glycoprotein present in most epithelial cells and tumors, and cytokeratin-19 (K19), a primitive keratin expressed by all epithelial cells, was assessed using RT-PCR as described (Gazdar et al., 1998). MCF-7 human breast tumor cell lines, U-937 human histiocytic lymphoma cell lines and Jurkat human T cell leukemia cell lines were routinely cultured with RPMI 1640 (GIBCO-BRL) supplemented with 10% FBS at 37° C. in a 5% $CO_2$ atmosphere. The MCF-7 human breast cancer cell line, human histiocytic lymphoma cell line (U-937) and the human T cell leukemia cell line (Jurkat) were obtained from the American Type and Tissue Culture Collection (ATCC).

Modified RDA. mRDA was performed as described (Yuan et al., 1999). In brief, two mg of DNA isolated from a breast cancer cell line (K151, tester) and its matched normal cell line (driver) by the QIAamp DNA blood kit (Qiagen Inc.) were cleaved with the restriction enzyme HpaII (10 U/μl; Boehringer Mannheim) in a 50 μl reaction at 37° C. overnight. Preparation of tester and driver master amplicons and subtractive hybridization were performed as described (Lisitsyn et al., 1993; Hubank and Schatz, 1994). After a second round of subtractive hybridization/PCR amplification, the difference products were subjected to a 2% agarose gel electrophoresis and purified by a DNA gel extraction kit (Qiagen, Inc). The purified DNA fragments were cloned in the pPCR-script Amp SK(+) cloning vector by using a PCR-Script Amp Cloning Kit (Stratagene). The inserts from positive clones were amplified and used as probes in master amplicon Southern blot. The candidate probes were then further tested by human genomic DNA southern blot.

Amplicon And Genomic DNA Southern Blotting. 6 mg of tester amplicon DNA (K151 cancer cell lines) and driver amplicon DNA (K151 normal cell lines) on 1.5% agarose gel were transferred to a positively charged nylon membrane (Boehringer Mannheim) and immobilized by exposure to UV light. The plasmids containing interesting inserts from RDA were used as templates with T3 and T7 primers for probe labeling using the PCR DIG probe synthesis kit (Boehringer Mannheim). Southern blotting and detection was carried out with the non-radiation Southern Blot detection kit (Genius, Boehringer Mannheim) according to the instruction of the manufacturer. For genomic DNA Southern blot, 5 μg of genomic DNA from the K151 cancer cell line and normal cell line were digested with HpaII or MspI overnight and then hybridized with the probe by using the same procedure as amplicon Southern blotting.

5' And 3' Rapid Amplification Of cDNA Ends (5' RACE And 3' RACE). A search for cDNA sequences was performed by using the SMART RACE cDNA amplification kit (Clontech Inc.). In brief, total cellular RNA was isolated from K151 and K259 cancer cell lines by using the high pure RNA isolation kit (Roche). Five hundred ng RNA was used for construction of the first-strand cDNA library. For the 5' RACE, the cDNA was synthesized using a modified lock-docking oligo (dT) primer and SMART II oligo primer provided in the kit. For the 3' RACE, cDNA was constructed using a traditional reverse transcription procedure, but with a special oligo (dT) primer provided by manufacturer. The protocol followed the instructions from the manufacturer. The primers used in the SMART RACE procedure are listed in Table 1. The cDNA fragments derived from 5' and 3' RACE were gel purified and sequenced by cloning and sequencing protocol as described.

TABLE 1

Primers used in Examples

| Primer name[a] | Sequence - 5'→3' (SEQ ID NO:) | Position[b] | Tm[c] |
|---|---|---|---|
| GC3-S | CCTGTCCACTGACTCCAGTG (SEQ ID NO: 16) | 7722-7741 | 57 |
| GC3-AS | ACTTGGCCACAGCATGCAG (SEQ ID NO: 17) | 7923-7905 | 57 |

TABLE 1-continued

Primers used in Examples

| Primer name[a] | Sequence - 5'→3' (SEQ ID NO:) | Position[b] | Tm[c] |
|---|---|---|---|
| GC3 UPF-AS | ACCAAAGGCCATGCGGAGGCCAGAGAA (SEQ ID NO: 18) | 7572-7598 | 67 |
| GC3 UPN-AS | CAACAACCCGCAGTGCCCCAGGAAGCCC (SEQ ID NO: 19) | 7523-7551 | 67 |
| GC3 DF-S | GCAGGGCTGGCTGGCCTTGGGTGAGAGG (SEQ ID NO: 20) | 7943-7970 | 67 |
| GC3 DN-S | CTTGCAGCGCCCAGAGGCACCCACCTG (SEQ ID NO: 21) | 8004-8030 | 67 |
| GC3 (1-3)-S | GCTACCTGGCGGAACTGGATTTCTC (SEQ ID NO: 22) | 4819-4843 | 61 |
| GC3 (1-3)-AS | CGCTTGCGTCGTACTTGTTCTTCTC (SEQ ID NO: 23) | 6240-6216 | 61 |
| GC3 (3-6)-S | AAGACGCAGGTTCTGGACTGGATCAG (SEQ ID NO: 24) | 6180-6205 | 63 |
| GC3 (3-6)-AS | TGGGATCCAGGTCCACGTCACTTC (SEQ ID NO: 25) | 7194-7171 | 63 |
| GC3 (6-8)-S | TCCTCAGACTCCGGTGGAAGTGACG (SEQ ID NO: 26) | 7155-7179 | 63 |
| GC3 (6-8)-AS | CCGGCTCAGCTTCTCGTAGGTCATG (SEQ ID NO: 27) | 8198-8174 | 63 |
| GC3 (8-9)-S | AGCTCAACGAGGGCCTCATGAAGTG (SEQ ID NO: 28) | 8065-8089 | 61 |
| GC3 (8-9)-AS | TCCCAGGACGATGGCTGACAATACAC (SEQ ID NO: 29) | 9352-9327 | 61 |
| ES31 | CCCCAGCCATGTACGTTGCTATCC (SEQ ID NO: 30) | (β-actin) | |
| ES33 | GCCTCAGGGCAGCGGAACCGCTCA (SEQ ID NO: 31) | (β-actin) | |
| GC3DD-S | CCTGTGTCCAGGAGTACACTAGATCATC (SEQ ID NO: 32) | 8569-8596 | 67 |
| INSE-S | AGAGGCAAGGGTCTCTACGTTG (SEQ ID NO: 33) | 8659-8680 | 62 |
| INSE-AS | TCCCTGGCCTTAAAAGTCATGT (SEQ ID NO: 34) | 8774-8795 | 62 |

[a]S-sense primer; AS-antisense primer
[b]Nucleotide positions are numbered with reference to ELF3 genomic sequence AF110184 (SEQ ID NO: 1)
[c]° C.

RNA Purification. All RNA isolations were extracted from 1-5×10⁶ exponentially growing cells by using the High Pure RNA isolation kit (Roche, Indianapolis, Ind.) according to the manufacturer's protocol. RNA in the cell lysate was selectively bound to a glass fiber fleece in a microcentrifuge filter tube during DNase I treatment and DNA removal. The bound RNA was purified by washing steps and eluted in 75 μl nuclease-free water. All RNA isolates were tested for genomic DNA contamination by PCR amplification before synthesis of cDNA. For RNase and Dnase I digestion analysis, ~2 μg total cellular RNA isolated from the K151 breast cancer cell line was digested with either 1 μg of RNase (Roche, Indianapolis, Ind.) in a total of 200 μl ddH₂O or 200 U of RNase-free DNase I (Roche, Indianapolis, Ind.) in 200 μl DNase dilution buffer at 37° C. for 20 min. RNase or DNase I was then inactivated by incubation at 70° C. for 10 min. The RNA in this mixture was then isolated using the same RNA isolation procedure as described. The RNA was eluted in 15 μl ddH$_2$O. The RNA was quantified by measuring the absorbance at 260 and 280 nm ($A_{260/280}$) and its integrity was verified on a formamide-agarose gel.

Separation Of Nuclear And Cytoplasmic RNA. RNA was extracted from the nuclear and cytoplasmic fraction of various cell lines. Cells (~5×10$^6$) were washed with ice-cold phosphate-buffered saline (PBS) 3 times and then disrupted with 375 μl lysis buffer (0.5% NP-40, 20 mM Tris-HCl, 100 mM NaCl, 5 mM MgCl$_2$, 1 mM dithiothreitol, and 1000 U of RNasin per ml) for 5 min on ice. This preparation was then gently centrifuged at 2000 rpm for 2 min. The pellet, which consists of nuclei, was resuspended in 200 μl of PBS for nuclear RNA isolation. The cytoplasmic enriched supernatant was centrifuged for another 2 min at 12,000 rpm to remove any contaminating nuclei. The supernatant was used for cytoplasmic RNA isolation. The RNA was then purified from the separated cytoplasm and nuclear fractions by using the same protocol as for total cellular RNA isolation.

RT-PCR And DNA-PCR Analysis. Before cDNA synthesis, all RNA isolates were tested for the presence of genomic DNA contamination by using β-actin primers to assure that there was no genomic DNA contamination in the RNA isolates. β-actin primers (ES31: 5'-CCCCAGCCATGTACGT-TGCTATCC-3' [SEQ ID NO:30] and ES33: 5'-GCCT-CAGGGCAGCGGAACCGCTCA-3' [SEQ ID NO:31]) were prepared to amplify a 394 bp fragment β-actin expressed gene in the same PCR conditions as GC3 primers which are listed in Table 1. cDNA was synthesized from purified total RNA, nucleic RNA or cytoplasmic RNA at 42° C. for 30 min in the presence of oligo d(T)16 primer with MuLV-reverse transcriptase by using RNA PCR kit (Perkin Elmer). PCR amplification (25 μl) was performed in PCR buffer containing 0.2 μM of each primer, 2.5 μl of the first-strand cDNA samples or 10-50 ng of DNA (for PCR), 200 μM each of deoxynucleoside trisphosphate (dNTP) and 2.5 U of Platinum Taq DNA polymerase (Gibco). When the PCR products were used for sequencing purposes, reading proof PWO DNA polymerase (Roche) mixed with AmpliTaq DNA polymerase (Perkin Elmer) (1:5 ratio) was used. The touch down PCR was used to improve the specificity (Hastings and Krainer, 2001; Cullen, 1998). The conditions of touch down PCR were as follows: initial denaturation was carried out at 94° C. for 3 min, then followed by 10 cycles, each consisting of denaturation at 94° C. for 1 min, annealing at 5° C. higher than actual primer annealing temperature for 1 min, extension at 72° C. for 1 min, and then followed by 25 cycles, characterized by denaturation at 94° C. for 1 min, annealing at actual primer annealing temperature for 1 min, and extension at 72° C. for 1 min. A final extension was carried out at 72° C. for 10 min. The amplified products were separated by electrophoresis on 2% agarose gels containing ethidium bromide in TAE buffer (40 mM Tris-acetate, 1 mM EDTA). The gel was photographed under UV light with Polaroid 677 film. The primers in PCR and RT-PCR reactions in our study were designed by Gene Runner 3.0 (Hasting Software, Inc.) based on the ELF3 gene sequence in GenBank (AF110184) (SEQ ID NO:1) and listed in the Table 1.

Northern Blot Analysis. Total RNA was isolated from freshly harvested K259T, Jurkat and MCF-7 cell lines using RNeasy Mini Kit combined with DNase digestion with the RNase-free DNase set (QIAGEN) according to the manufacturer's instructions. Ten μg of each RNA aliquot was fractionated on 1.25% SeaKem Gold agarose gel from Reliant RNA Gel System (Camnrex, Rockland, Me.). RNA was transferred to nylon membrane by capillary transfer and immobilized by UV cross-linking. Probes were labeled with [α-$^{32}$P] dCTP using the Prime-It II kit (Strategene, La Jolla, Calif.). A cDNA clone from 5'RACE library containing ELF3 mRNA from exon 1 to exon 7 without intron retention was used to generate a probe that was 922 bp in length. This probe encoded amino acid residues 1-262 along with a 135 bp 5'UTR, which differed from the published ELF3 mRNA 5' UTR. The GC3 DNA clone from the original RDA protocol was used to generate a probe that was 531 bp in length and contains 496 bp of ELF3 gene intron 7 from nt 7514 to 8010 and 35 bp of exon 8 from nt 8011 to 8045. A cDNA clone containing a β-actin RT-PCR product was used to synthesize a 392 bp probe which encodes amino acid residues 153-283. Hybridization was performed at 68° C. in the ExpressHyb™ hybridization solution (CLONTECH, Palo Alto, Calif.) for 3 h. The blots were washed according to the manufacturer's instructions. The blots were reprobed with μ actin cDNA to verify that there was equal loading of RNA for each cell line. The size of transcripts was estimated by comparison to RNA markers 0.2-10 kb (Sigma, St. Louis, Mo.).

DNA Sequencing. The DNA fragments from RDA, and the cDNA fragments from 5' RACE and 3' RACE were cloned in PCR-Script Amp SK(+) cloning vector by using the PCR-Script Amp Cloning Kit (Stratagene). Plasmids were purified by the Bio-Rad Plasmid Miniprep Kit, and sequenced by T3 and T7 primers in both directions. The DNA fragments from the PCR reaction were diluted 1:10 with dH$_2$O and sequenced with primers used in the PCR reaction. Sequencing was done at the North Shore University Hospital (New York) DNA Sequencing Facility using an ABI Prism 377 DNA Sequencer. Nucleotide and protein BLAST of the National Center for Biotechnology Information was used to searching for homologous sequences (Altschul et al., 1990; Gish and States, 1993; Altschul et al., 1997).

Breast Cancer Tissue and Normal Tissue Samples: cDNA prepared from breast cancer biopsies and normal tissue from the same patient are described in Yuan et al. (1999) and provided by Dr. H. P. Xu.

Results

Establishment Of Human Breast Tumor And Matched Normal Cell Lines. Paired human breast cancer and normal cell lines were established from effusions of patients with breast cancer. After 8 months in culture, adherent cells (denoted K151) showed normal myofibroblast cell morphology with normal chromosomes in cytogenetic analysis. K151 non-adherent cells became partially adherent and showed morphologically malignant characteristics. Malignant cells revealed polyploidy. Cytogenetic analysis revealed two extra chromosome 1 copies, as well as numerous unassigned small chromosomal fragments. These cells expressed both EGP2 and K19, while the K151 myofibroblast cell line only expressed K19. These two cell lines are referred to as the cancer cell line and the normal cell line in mRDA analysis. Using the same method, breast cancer cell lines denoted K234 and K259 were established and used for characterization of the DNA fragments isolated from modified RDA of K151.

Isolation Of A Highly Amplified DNA Sequence GC3 From Human Breast Tumor Cell Lines BY mRDA. The DNA isolated from K151 breast cancer cell lines (tester) and matched normal cell lines (driver) were cleaved with the HpaII enzyme and applied to the modified RDA protocol. After two rounds of DNA amplification/subtraction and PCR amplification, different products (DP2) were isolated from breast tumor cell lines. The gel purified DP2 fragments were cloned into pPCR-script AMP SK(+) cloning vector and amplified as described. Among 21 clones, 9 clones had different size DNA fragment inserts defined by restriction enzyme digestion. These were used as probes for amplicon Southern blotting. The clones which hybridized only to tester amplicon (cancer) and not to driver amplicon (normal) were sent for sequencing. The nucleotide BLAST search showed that two clones denoted GC2 and GC3, encoded the ELF3 gene 7677-8045 (368 bp) and 7514-8045 (531 bp) respectively (using the numbering system of SEQ ID NO:1). The nucleotide BLAST search against GenBank Human Expressed Sequences Tags Database (EST) revealed that 365 bp of our GC3 is 98% homologous to a sequence tag of human cDNA (accession number BG960569) derived from the Human Cancer Genome Project and this sequence is located within intron 7 of the ELF 3 gene from nt 7514 to 7878.

The DNA fragment of GC3 had CCGG on both ends (SEQ ID NO:11). The 5' terminus is located in a CpG island within intron 7 and the 3' terminal extended to the 5' position at 35 bp of exon 8 of the ELF3 gene. We focused our attention on the larger GC3 DNA fragment. To confirm the difference observed in the tester and diver amplicons, genomic DNA Southern blotting was carried out by using GC3 DNA fragment as a probe to hybridize to tester and driver DNA. The same amount of genomic DNA digested by HpaII and MspI from K151 cancer and matched normal cell lines was applied to Southern blotting. The GC3 DNA fragment only hybridized to the DNA from the breast cancer cell lines, but not to the DNA from the matched normal cell lines, whether HpaII or MspI enzymes were used for digestion (FIG. 1).

To determine whether the GC3 DNA fragment exists exclusively in our breast cancer cell lines, a sensitive PCR technique was employed. Primers which amplify a 202 bp fragment from intron 7 of the ELF3 gene were synthesized based on the sequence derived from GC3. PCR was carried out on DNAs from 3 paired breast cancer and normal cell lines (K151, K234 and K259). ~200 bp PCR products were produced both in breast cancer cell lines and normal cell lines (FIG. 2). The band appearing in the normal cells of K151 was considerably weaker than that of the cancer cell line (FIG. 2). The result showed that the GC3 DNA fragment in intron 7 of ELF3 selected by modified RDA was not uniquely present in the DNA of the cancer cell lines. Nonetheless this sequence does appear as a difference using the less sensitive Southern blotting and amplicon Southern blotting (FIG. 1). This difference thus appears to be due to amplification of this gene product in the tester and not due to mutation within this gene. RDA can produce a difference this way when a DNA fragment is highly repeated or multiple copies are present in the tester in contrast to the driver (Lisitsyn et al., 1995).

Figure 3:
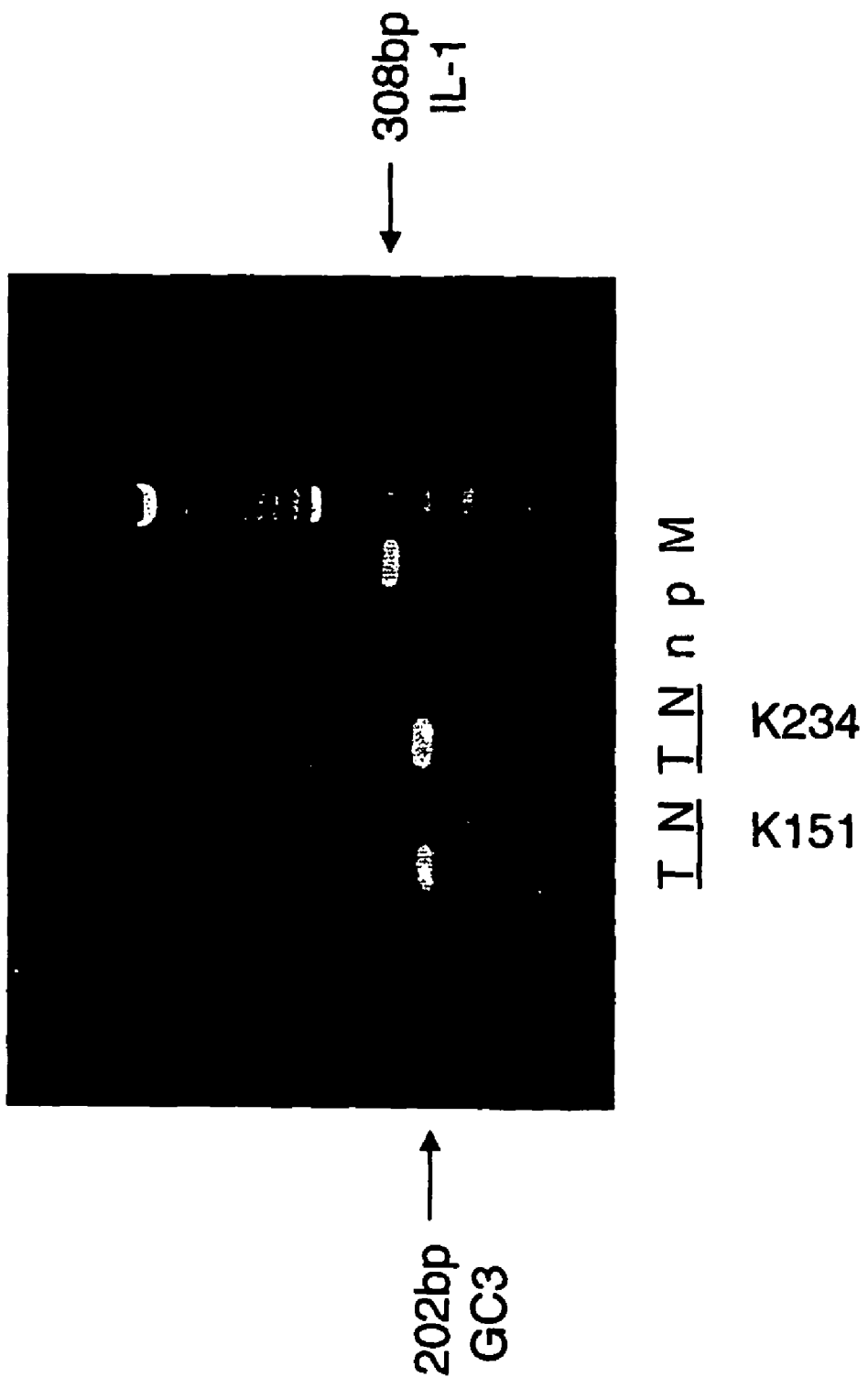
FIG. 3 shows a gel of electrophoresed products from a reverse transcriptase-polymerase chain reaction (RT-PCR) amplification of GC3 in breast tumor cell cultures and matched normal cell cultures. The 202 bp GC3 was amplified from breast tumor cell lines but not matched normal cell lines, indicating the presence of GC3 in mRNA from the tumor lines but not the normal lines. Lane T, breast tumor cell lines; lane N, normal matching line. K151 is a myofibroblast cell line; K234 is a CD4+ T lymphocyte line. IL-1 served as a positive control for RT-PCR (lane p); lane n, negative control; lane M, 100 bp DNA ladder.
Figure 4:
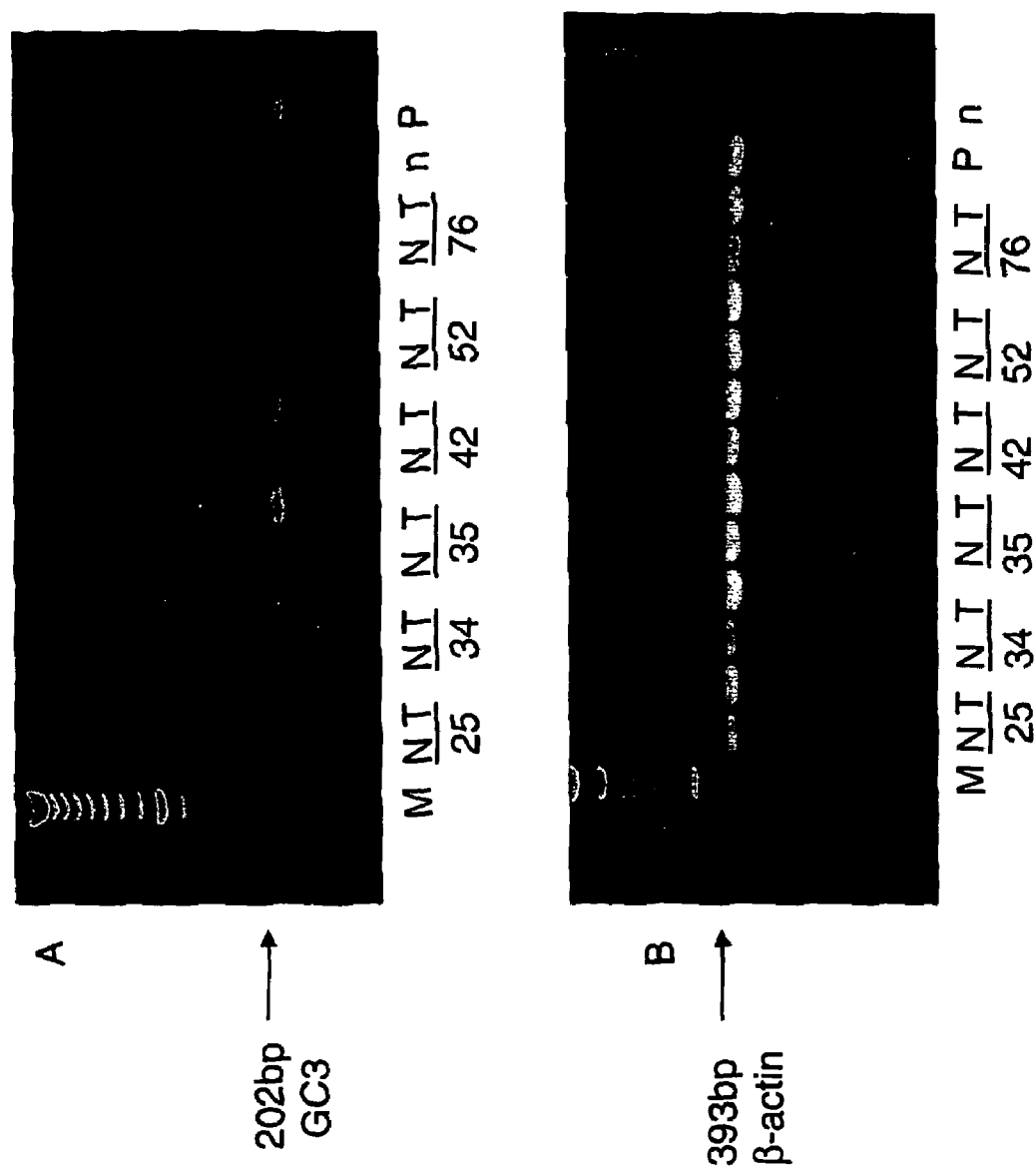
FIG. 4 shows gels of electrophoresed PCR products of cDNAs from breast tumor tissues and matched normal tissues. The gels demonstrate that the 202 bp GC3 fragment is present in mRNA of breast tumor tissues but not in matched normal tissues. Six paired cDNAs from breast tumor and matched normal tissues were amplified by GC3 primers in PCR reactions. GC3 was expressed in four of six breast tumor tissues, but none of the six matched normal tissues (Panel A). The presence of intact input RNA was checked in all samples by amplification of human β-actin (Panel B). Lane M, 100 bp DNA ladder; lane N and T represent normal tissue and breast tumor respectively. The patient ID numbers are below the N and T lanes. DNA from K151 tumor cells were used as a positive control (lane p); double distilled $H_2O$ was used as a negative control in the PCR reactions.
Figure 6:
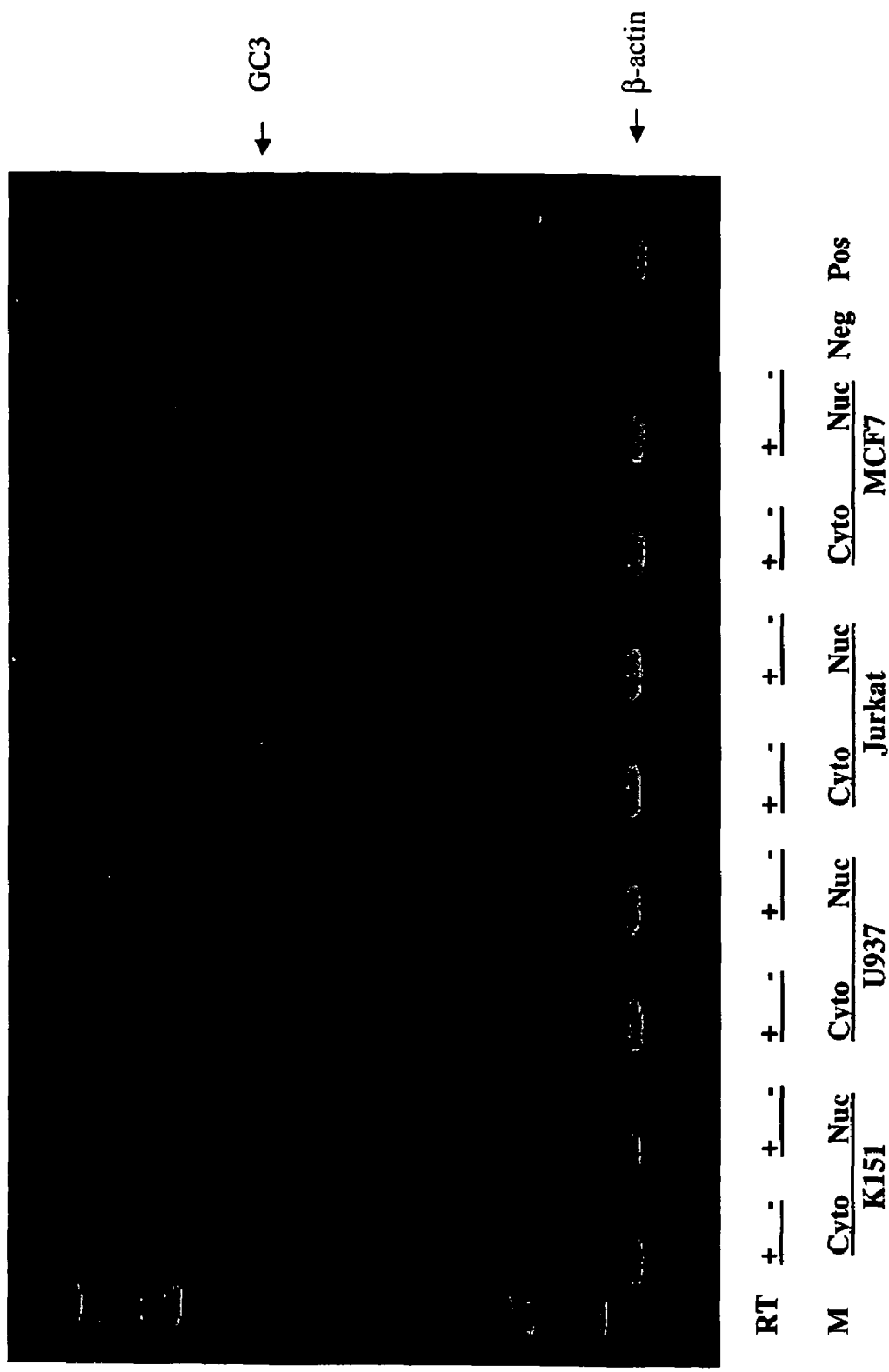
FIG. 6 shows a gel of electrophoresed PCR products evaluating nuclear or cytoplasmic presence of GC3 in RNA from breast tumor cells. RNA was isolated from nuclear (Nuc) and cytoplasmic (Cyto) fractions. PCR using GC3 primers was performed on the RNA isolates with (RT+) or without (RT−) a prior reverse transcription step. The presence of intact input RNA was checked in all samples by amplification of human β-actin. Lane M, 100 bp DNA ladder. DNA from K151 tumor cells was used as a positive control (Pos); $ddH_2O$ was used as a negative control. The GC3 202 bp product was produced from both nuclear and cytoplasmic mRNA from K151 tumor cell lines and nuclear mRNA from MCF7 cell lines; weakly produced on cytoplasmic mRNA from MCF7 cell lines; and produced in nuclear mRNA from U937 cell lines only when the mRNA was reverse transcribed to cDNA. No GC3 or β-actin products were produced on RNA isolates without reverse transcription, ruling out contamination of RNA isolates with genomic DNA.

Retention Of GC3 In Cytoplasmic mRNA Of ELF3 Gene In Human Breast Cancer Cells. RT-PCR was performed on the mRNA isolated from paired cell lines (K151 and K234) by using the same GC3 primers. The results showed that GC3 was expressed in the breast cancer cell lines but not in matched normal cell lines (FIG. 3). Sequence analysis of this 202 bp RT-PCR product showed 100% homology to the GC3 sequence defined by GC3 primers. cDNA from six paired human breast cancer and matched normal tissues, provided by Dr. H. P. Xu and prepared as described in Yuan et al. (1999), were also examined for expression of intron 7 with GC3 primers. GC3 was present in the mRNA of 4 of 6 breast cancer tissues, but not in normal tissue (FIG. 4). Expression of GC3 in breast cancer cell lines K151, K234 and most breast cancer tissues indicates that intron retention occurs in many breast cancer cells. In order to exclude RT-PCR products that might have resulted from amplification of contaminating genomic DNA in the preparation of RNA, differential DNase I and RNase digestion was performed on the total RNA preparation from K151 cancer cell line before cDNA synthesis. The RT-PCR product showed that GC3 and β-actin was generated in the RNA isolated only after DNase I treatment, but not in the sample after RNase digestion (FIG. 5). This confirmed that GC3 was retained in the RNA fraction of the cells and was not there as a result of genomic DNA contamination in our RNA preparation prior to reverse transcription. To elucidate whether GC3 is retained in the cytoplasmic mRNA of the breast cancer cells, RNAs were purified from nuclear and cytoplasmic fractions prepared from the K151 and the MCF-7 human breast cancer cell line, from the human histiocytic lymphoma cell line (U-937) and the human T cell leukemia cell line (Jurkat). cDNA was prepared from these RNAs, and b-actin and GC3 primers were used to detect normal exonic b-actin and abnormal intronic GC3. The same GC3 and b-actin primers were used on the RNA prepared prior to preparation of the cDNA from these cells to rule out any genomic DNA contamination prior to reverse transcription. In an RT-PCR reaction, ~200 bp GC3 products were produced in the nuclear and cytoplasmic RNA of both the K151 and MCF7 breast cancer cell lines (FIG. 6). GC3 was also weakly produced in the nuclear RNA but not in the cytoplasmic RNA of the U-937 cell line. There was no GC3 RT-PCR product in either the nuclear or cytoplasmic RNA from the Jurkat cell line. No GC3 or β-actin amplification occurred in any nuclear or cytoplasmic RNA samples prior to the reverse transcription step, excluding any genomic DNA contamination in the RNA isolates. The positive β-actin results in the RT-PCR reaction demonstrated the integrity of the RNA and assured that equal amounts of RNA were present in each sample (FIG. 6). mRNA was further purified from all cytoplasmic and nuclear RNA extracts by oligo (dT)$_{20}$ coated magnetic beads. This mRNA was then subjected to RT-PCR and the cDNA was tested with GC3 and β-actin primers. The same results were obtained with this method of RNA purification. GC3 amplification was seen only in the breast cancer cell lines K151 and MCF7 but not in U937 and Jurkat cell lines (data not shown). These results confirmed that GC3 is retained in the cytoplasmic mRNA of human breast cancer cells.

Figure 21:
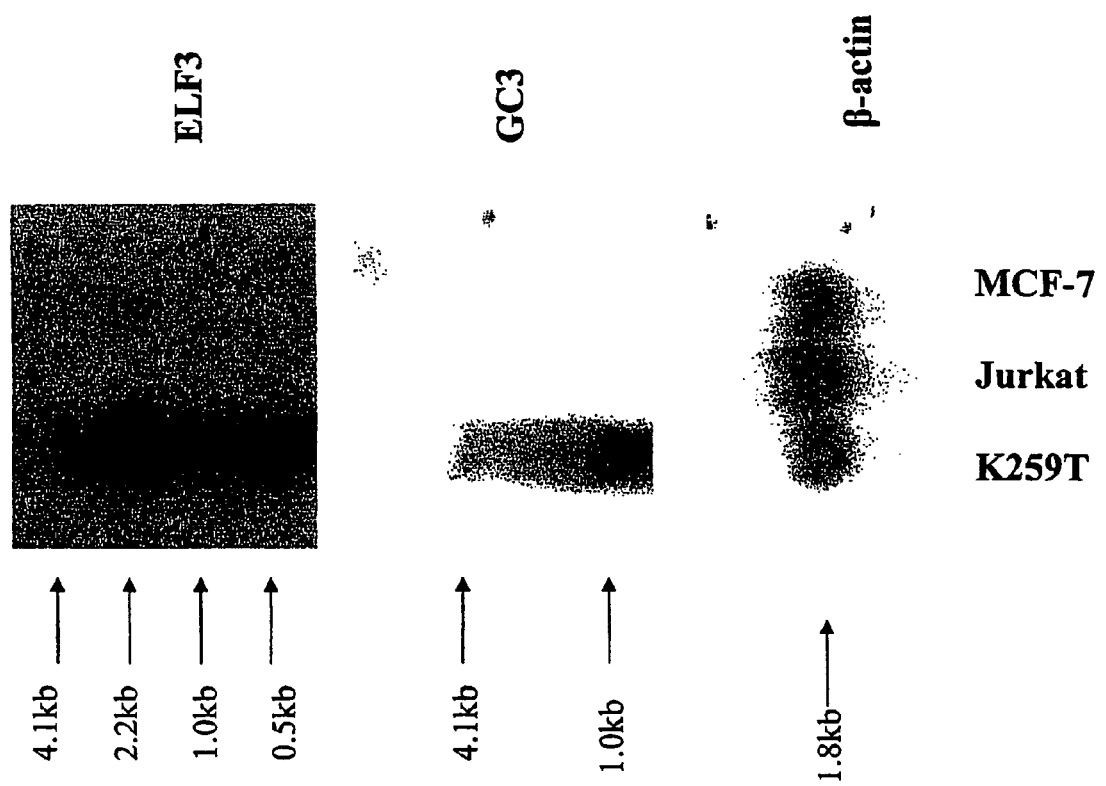
FIG. 21 shows the results of a northern blot analysis of GC3 (intron 7) and normal ELF3 mRNA expression in human breast cancer cell lines. Total RNA was isolated from fresh harvested cell lines K259T, Jurkat, and MCF-7. Each lane was loaded with 10 μg of RNA. The blot was sequentially hybridized with radiolabeled ELF3 (top panel), GC3 (middle panel) and β-actin (lower panel) probe as described in Materials and Methods. The position and size of RNA markers are shown. Fully spliced ELF3 can be seen as a transcript with a molecular weight of 2.2 kd. Other transcripts are seen at 4.1, 1.0 and 0.5 kd. The 4.1 and 1.0 kd transcripts hybridize to the GC3 probe indicating retention of this intronic area.

Fully Spliced and Unspliced ELF mRNA Demonstrated by Northern Blot Analysis. In order to determine if intron retention is significantly present in ELF3 mRNA in breast cancer, total mRNA was prepared from human breast cancer cell lines K259T, MCF-7 and the human T cell leukemia cell line Jurkat. A northern blot was prepared and probed for the expression of ELF3, GC3 and μ action mRNA (FIG. 21). A highly expressed 2.2 kb ELF3 fully spliced mRNA transcript was observed in K259T, which was also weakly visible in the MCF-7 cell line mRNA. A 4.1 kb ELF3 mRNA was also noted in K259T along with 1.0 kb and 0.5 kb bands. There was no ELF3 expression in Jurkat cell lines. Using the GC3 intron 7 probe, there were two bands at 4.1 kb and 1.0 kb obseved in K259T mRNA. These two bands represent retained intron products in the ELF3 mRNA from this cell line. These two bands appear at the same molecular weight seen with the fully spliced ELF mRNA probe, which is undoubtedly due to binding to the exonic portion in these mRNA transcripts.

Figure 7:
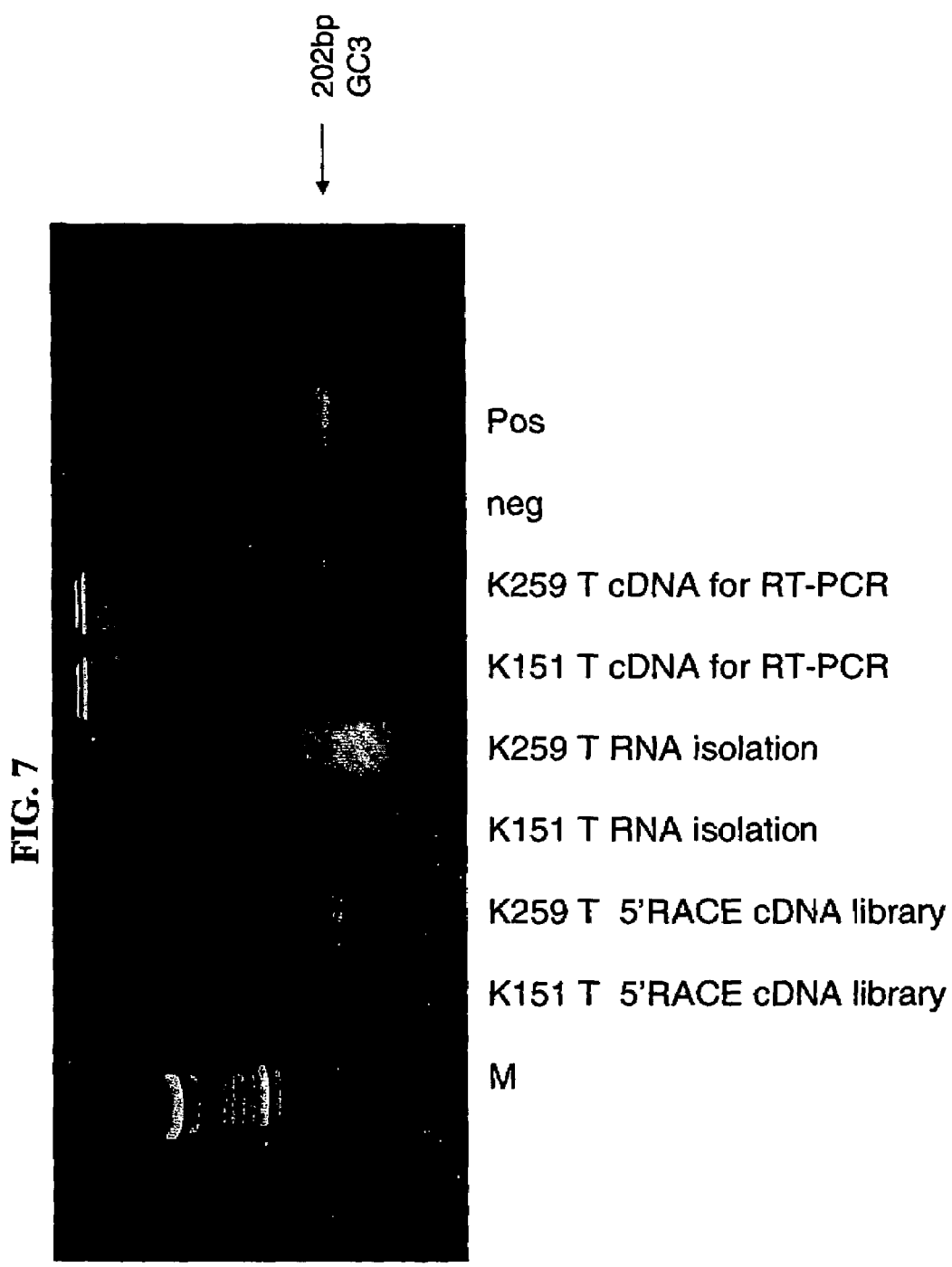
FIG. 7 shows a gel of electrophoresed PCR products evaluating GC3 expression on cDNA libraries from K151 tumor cell lines for 5' RACE and RT-PCR. The 5' RACE cDNA library was synthesized by modified lock-docking oligo(dT) primer and SMART II oligo (SMART RACE cDNA Amplification Kit, Clontech Inc.); cDNA was synthesized by oligo (dT)16 (RNA PCR Kit, Perkin Elmer) as well as total cellular RNA, and was amplified using GC3 primers. GC3 was amplified from both tumor cell lines, irregardless of the method employed for cDNA synthesis. More importantly, GC3 was not amplified from 1 µg total cellular RNA from K151 tumor cell lines and 3 µg total cellular RNA from K259 tumor cell lines, demonstrating no genomic DNA contamination in the RNA isolations. A GC3 plasmid was used as a positive control for the PCR reaction.
Figure 8:
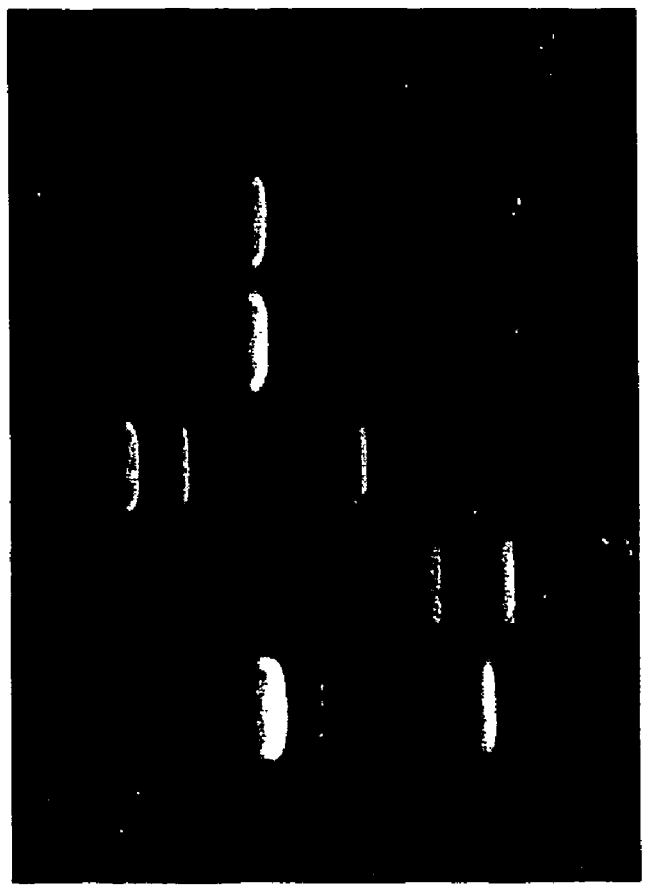
FIG. 8 shows a gel of electrophoresed PCR products evaluating 5' RACE and 3' RACE results from K151 and K259 cDNA. cDNAs for 5' RACE and 3' RACE were synthesized by using RNA from K151 and K259 breast tumor cell lines. In the 5' RACE, GC3 UPF (SEQ ID NO:18) and GC3 UPN (SEQ ID NO:19) were used as the first and second primers. In 3' RACE, GC3 DF (SEQ ID NO:20) and GC3 DN (SEQ ID NO:21) were used as the first and second primers.

Presence Of Partially Unspliced ELF3 mRNA Sequence In Human Breast Cancer Cell Lines. To verify the RT-PCR results and determine that GC3 is retained in cytoplasmic mRNA of breast cancer cells as part of intron 7 of ELF3, the RACE technique was used to determine the cDNA sequence of ELF3 gene. RNA was extracted from K151 and K239 cell lines as described above. After RNA extraction, RNA preparations were screened to assure the absence of genomic DNA contamination using PCR amplification with GC3 primers as shown in FIG. 5A. After establishing the 3' and 5' RACE cDNA libraries, GC3 was confirmed to be present in these libraries using the GC3 primer (FIG. 7). When GC3 UPF (SEQ ID NO:18) and GC3 UPN (SEQ ID NO:19) were used as the first primer and nested primer, respectively, in our 5' RACE experiments, an ~1000 bp DNA fragment and an ~300 bp DNA fragment were produced in the K151 cDNA library, and ~400 bp and ~100 bp DNA fragments were produced in the K259 cDNA 5' RACE library (FIG. 8). The ~1000 bp DNA fragment from the K151 5' RACE was gel purified and cloned. All nine positive plasmids containing this DNA fragment were selected. Three of these were sequenced. The sequence from 2 of the 3 sequenced positive plasmids showed 100% homology to 1002 bp of the ELF3 genomic DNA sequence (AF110184) from 6550 to 7551 (SEQ ID NO:12) which contains the entire intron 4, 5, and 6 and 71 bp from the 5' end of intron 7 (FIG. 9). All intron/exon splice junction borders conform with the splice site consensus G/GT . . . C/AG rule without any single nucleotide mutation. The third sequenced clone had 100% homology to the normal cDNA sequence of ELF3 which contains exon 1 to exon 7 without any intron retention.

When GC3 DF(S) (SEQ ID NO:20) and GC3 DN(S) (SEQ ID NO:21) were used as the first primer and nested primer in the 3' RACE experiments, an ~1000 bp DNA fragment was produced in both K151 and K259 cDNA 3' RACE libraries (FIG. 8). The product from K151 was gel purified and cloned. Sequence analysis revealed all the sequences had normal cDNA of ELF3 which contained properly spliced exon 8 and exon 9, 3' UTR and a polyA tail. In order to demonstrate GC3 (as part of intron 7) retention in the ELF3 mRNA, 5' RACE was pursued with GC3 primers. The sequence analysis showed homology to the ELF3 genomic sequence from 7270 to 8198, which contained the entire intron 7. The sequencing results indicated GC3 was retained as part of intron 7 of ELF3 in the mRNA pool. Additionally, introns 4, 5, 6 and 7 were retained in their entirety in the ELF3 mRNA from breast cancer cell line K151. The 5' RACE and 3' RACE results from the breast cancer cell line K151 is summarized in FIG. 9.

Figure 10:
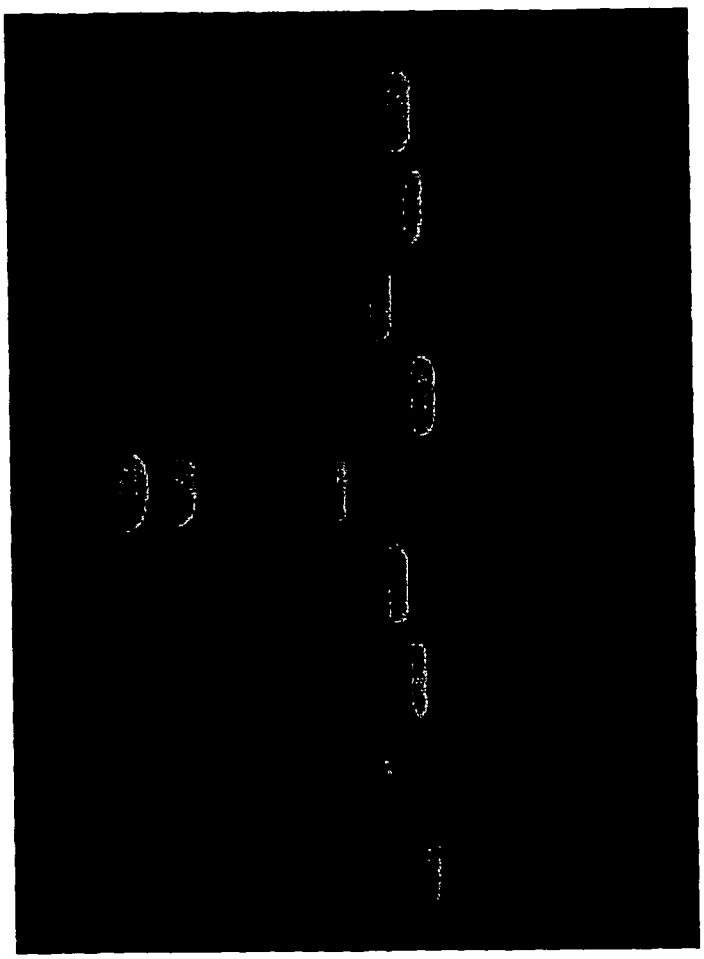
FIG. 10 shows a gel of electrophoresed PCR products evaluating the presence of spliced ELF3 mRNA in breast tumor cell lines in RT-PCR reactions. Primers 1-3, 3-6, 6-8 and 8-9 amplified ELF3 exon 1 to 3, 3 to 6, 6 to 8 and 8 to 9 respectively. The length of DNA fragments with and without intron retention are labeled. DNA fragments without intron retention were observed in exon 1 to 3, 3 to 6, 6 to 8 and 8 to 9 on both breast tumor cell lines K151 and K259.

Presence of Normal ELF3 mRNA In Human Breast Cancer Cells The fully spliced mRNA from our breast cancer cells provided herein as SEQ ID NO:2 is 1959 bp and is predicted to encode a 371 amino acid protein (SEQ ID NO:4), which shares 98% homology to the ELF3 protein sequence. Even though the coding sequence (CDS) was 98% homologous to the published cDNA sequence of the ELF3 gene (Oettgen et al., 1999; Oettgen et al., 1997a; Brembeck et al., 2000; Lisitsyn et al., 1995), the 5' UTR was different and was derived from 4876 to 5006 instead of 4777 to 4888 of the ELF 3 genomic DNA sequence (SEQ ID NO:1). The presence of fully spliced mRNA of the ELF3 gene in our breast cancer cells was further confirmed by the sequence analysis of RT-PCR products, in which the PCR reaction was performed on K151 and K259 cDNA libraries prepared for the 5' RACE (FIG. 10). Primers were chosen which spanned intronic areas [Table 1-GC3(1-3)S and AS (SEQ ID NO:22 and 23); GC3 (3-6)S and AS (SEQ ID NO:24 and 25); GC3(6-8) S and AS (SEQ ID NO:26 and 27); GC3(8-9)S and AS (SEQ ID NO:28 and 29)]. The fully spliced exon 1, 2, 3 (343 bp), exon 3, 4, 5, 6 (460 bp), exon 6, 7, 8 (369 bp) and exon 8, 9 (409 bp) were amplified with four different pairs of primers, indicative of appropriate splicing of introns in these products. The result indicates that fully spliced mRNA of ELF3 constitute much of the ELF3 mRNA. The sequence analysis reveals normal splicing of all 8 introns from mRNA of ELF3. The RT-PCR and cDNA sequence analysis indicated that both partially unspliced ELF3 mRNA which contains intron 4, 5, 6 and 7 and fully spliced normal ELF3 mRNA are present in human breast cancer cell lines (FIG. 10).

Discussion

Malignant breast cancer effusions were used to obtain normal and cancer cell lines from the same patient in order to find genetic differences between the autologous cell lines. An mRDA technique using the malignant cell lines as a tester and the normal cell lines as a driver was utilized. A 531 bp DNA fragment, denoted GC3 (SEQ ID NO:11), positioned at 7514-8045 in intron 7 and exon 8 of the ELF3 gene, was obtained as a difference. As the GC3 sequence was normal, amplification of GC3 was felt to be responsible for the difference, as RDA can detect small restriction fragments with different sequences, but can also detect amplified sequences that are enriched by kinetic factors and cannot be completely subtracted by the driver (Lisitsyn et al., 1995). Cytogenetic analysis of the malignant line K151 used in the procedure revealed two extra copies of chromosome 1, the site of ELF3. Fluorescence in situ hybridization (FISH) has shown ELF3 amplification in the SK-BR-3 (5 to 6 copies) and BT-474 (4 copies) breast cancer cell lines, which results predominantly from an increase in chromosome 1q number (Chang et al., 1997).

As GC3 was assumed to be upregulated in the malignant clone, expression of this area was sought and found by RT-PCR. GC3, as part of intron 7 of ELF3 gene, was retained in the ELF3 cytoplasmic mRNA transcript in breast cancer cell lines and most breast cancer tissues (4 of 6) but not matched normal cell lines and tissues. Great care was taken to exclude DNA contamination as an artifactual cause of the findings. The 5' and 3' RACE procedures were used to confirm GC3 intron sequences in ELF3 cytoplasmic mRNA. These procedures further showed that there was retention of introns 4, 5, and 6 in mRNA, along with fully spliced 1959 bp normal transcripts of mRNA.

Our northern blot analysis, with normal mRNA as a probe, showed the presence of the 2.2 kb mRNA of fully spliced ELF3 gene in both K259 and MCF7 cell lines. A larger-sized 4.1 kb transcript as well as a 0.5, 1.0 and 2.2 kb transcript in the blot of K259 was also seen. When GC3 intron 7 was used as a probe, the 4.1 and 1.0 kb transcripts revealed the presence of ELF3 intron 7 in the mRNA in the transcripts of K259 cells, confirming that ELF3 intron 7 is retained in these transcripts. The 4.1 kb transcript can be seen in several other published studies (Chang et al., 1997; Oettgen et al., 1997; Tymms et al., 1997; Andreoli et al., 1997; Chang et al., 2000; Barnes et al., 1992; Kim et al., 2002; Ma et al., 2003; Raynor et al., 2002). Alternate size transcripts of ELF-3 were first described by Oettgen et al. (1997) who demonstrated 1.9 kb and 1.1 kb alternate splice forms of ELF3 mRNA (ESE-1) in skeletal muscle, called ESE2a and ESE2b. On the same gels one can see a higher molecular weight transcript in the northern blots of various organs in fetal and human adult tissues. A higher molecular weight transcript is also seen in all northern blots of mouse embryonal carcinoma cells (EC) and is upregulated by retinoic acid along with the 2.2 kb transcript using the mouse homologue of ELF3 as a probe (Kim et al., 2002). This higher molecular weight band along with fully spliced 2.2 kb ELF3 transcript also appears in northern blots of the BEAS-2B broncoepithelial cell line induced by retinoic acid (Ma et al., 2003). One can see a weak higher molecular weight band felt to represent "genomic DNA" contamination in breast cancer cell line MCF7, T47D, PMC42, Hs.578t, MDA-MB-231, and MDA-MB453 cells using RT-PCR techniques in spite of the fact that in 5 other cDNAs studied there does not appear to be genomic contamination. A similar and more distinct band can be seen in mononuclear cells spiked with MDA-MB453 cancer cells in the same study (Raynor et al., 2002).

The appearance of this large ELF3 transcript in the northern blots has been speculated to appear because 1) it contains additional 3' untranslated sequences which result from differential polyadenylation (Tymms, 1997); 2) it may also represent a preprocessed ELF3 transcript; 3) it may cross-hybridize to a homologous species (Ma et al., 2003). Our results support the second possibility, i.e., the presence of unspliced preprocessed mRNA transcripts. Our RACE results further confirm these findings and show the large sized ELF3 transcript containing unspliced introns, as well as the fully spliced ELF3 mRNA.

This is the first time that transcripts of ELF3 with multiple introns were found to be retained in cytoplasmic ELF3 mRNA in breast cancer. Intron retention in breast cancer cell lines and breast cancer tissue has also not been previously described. Clearly this is a pathological process and distinguishes breast cancer cells from normal cells. These findings indicate that abnormal mRNA processing is involved. Aberrant mRNA processing may take place by a variety of mechanisms, and may cause appropriate effects as well as pathological states. Exon skipping, abnormal splice site selection, and full intron selection have been described (Stutz and Rosbach, 1993; Krug, 1993; Stella et al., 2001; Hellwinkel et al., 2001; Beghini et al., 2000). Intron sequences have been shown to have motifs which can alter gene expression by influencing transcription rate (Matsumoto et al., 1998). Introns may code for independent proteins (Krug, 1993), may extend the coding sequence of an adjoining exon, or may provide alternate translation termination signals (Beghini et al., 2000). The appearance of introns in cytoplasmic mRNA is unusual in eukaryotic cells, though physiologic alternate splicing provides a mechanism for expanding protein expression (Hide et al., 2001). Splice site mutation may slow or prevent intron removal, but these incompletely spliced mRNAs are not transported into the cytoplasm (Stutz and Rosbash, 1998; Krug, 1993). Export of rRNA through the nuclear membrane usually requires splicing of all introns (Darnell et al., 1997; Cramer et al., 2001).

A database of aberrant splicing in mammalian genetic disorders has shown that genomic mutation with resultant intron retention is relatively rare (Nakai and Sakamoto, 1994). A nonsense mutation causing exon skipping and intron retention of LKB1/STK11, a Peutz-Jeghers syndrome gene, may contribute to tumorigenesis in a small fraction of malignant melanomas (Guldberg et al., 1999). Intron retention of non-mutated ELF3 (intron 4, 5, 6, 7) in breast cancer cells and tissue containing multiple normal stop codons excludes alternate splicing as a cause.

Intron retention associated with cancer cells is seen with the CD44 gene. Intron 9 and intron 18 of the CD44 gene are retained in the cytoplasmic mRNA transcripts in tumors. CD44 is known to be composed of at least 20 exons, ten or more of which can be alternatively spliced to produce various isoforms (Cooper, 1995; Matsumura et al., 1999; Goodison et al., 1998; Yoshida et al., 1995).

While intron retention appears rare in cancer cells it is commonly used by viruses to make more proteins from a simple nucleic acid organization. In HIV-1, the rev protein is able to bind to the rev response element and prevent the splicing out of introns, allowing full transcripts of the HIV RNA to enter the cytoplasm. It protects the viral RNA from intron splicing and helps bind the mRNA to the nucleopore for external transport of unspliced mRNA to the cytoplasm (Cullen, 1998; Flint et al., 2000; Favaro and Arrigo, 1997). In herpes simplex 1, the protein ICP27 acts like Rev to make the cellular gene for α-globin appear in an unspliced fashion in the cytoplasm. ICP27 may act after pre mRNA to prevent degradation of some intron-containing fragments and then help those fragments out of the nucleus through an alternative nuclear export pathway (Cheung et al., 2000; Ellison et al., 2000).

Some viruses have been speculated to cause human breast cancer, including a retrovirus (Ketdar et al., 1984; Moore et al., 1971; Wang et al., 1998; Wang et al., 1995; Pogo et al., 1997; Al-Sumidaie, 1988), a polyoma (Fluck et al., 1996) and a herpes virus (Bonnet et al., 1999). One could speculate that the ELF3 intron retention could be caused by some viral product which acts indirectly on the ELF3 gene similar to the way ICP27 acts on the α-globin gene. The appearance of intron retention of the ELF3 gene could thus be used to search for a potential viral protein which may result in breast cancer.

EXAMPLE 2

Cytoplasmic Intron Retention and a New Alu Element in the mRNA of the ELF3 Gene in Peripheral Blood Mononuclear Cells from Patients with Breast Cancer Example Summary Example 1 describes the retention of intron 7 of the ELF3 gene in cytoplasmic mRNA in breast cancer tissue and breast cancer cell lines but not in autologous normal breast epithelial cells. That finding, along with retention of introns 4, 5 and 6 of ELF3 and expression of fully spliced ELF3 mRNA was demonstrated using reverse transcriptase PCR (RT-PCR) and by 5'- and 3'-rapid amplification of cDNA ends (RACE). As described in this Example, downstream genomic DNA walking from intron 7 of ELF3 led to the discovery of a new Alu element, termed $Alu_{kwd}$ (SEQ ID NO:13), which was found inserted in an antisense orientation between nt 8762 and nt 8763 of the ELF3 gene (SEQ ID NO:1). This $Alu_{kwd}$ was found to be retained in the cytoplasmic mRNA as a fragment of intron 8 in breast cancer tissues and cell lines similar to intron 7. In order to see if $Alu_{kwd}$ and intron 7 retention occurred in other cells than breast epithelium, peripheral blood mononuclear cells (PBMCs) from breast cancer patients were tested for these gene fragments in the total RNA from these PBMCs. Great care was taken to assure that there was no contamination of the RNA with genomic DNA prior to creation of cDNA libraries. PBMCs from 13 of 28 patients with ductal carcinoma in situ (DCIS) with or without invasion were found to have intron 7 retention while of 28 had $Alu_{kwd}$ retention. All patients with $Alu_{kwd}$ had concomitant intron 7 retention. Three of 25 patients without DCIS but with invasive duct cancer or invasive lobular cancer had intron 7 and/or $Alu_{kwd}$ retention. Only 2/20 PBMCs from normal patients had intron 7 retention while 0/20 normals had $Alu_{kwd}$ retention. The association of retention of intron 7 and/or of $Alu_{kwd}$ with DCIS was highly statistically significant (p value=0.008) using the Chi square test. The presence of intron retention of this epithelium-specific mRNA within PBMCs has not been previously shown. The cause of this unusual intron retention in these cells is not known, but this finding is useful in understanding the pathogenesis of DCIS, and as the basis for an assay to distinguish DCIS from other forms of breast cancer. A better understanding of the biology of ELF3 might provide a new target for developing better chemotherapy for breast cancer.

Introduction

In this Example, ELF3 gene walking upstream of intron 7 led to the discovery of a previously undescribed Alu element inserted within another Alu element in a reverse orientation within intron 8 of the ELF3 gene. This Alu, designated $Alu_{kwd}$, is also found retained in cytoplasmic mRNA in breast cancer cells and breast cancer tissue along with the retention of a fragment of intron 7 which we designate as GC3. These phenomena were explored further using normal cells from breast cancer patients to determine whether there is a general error in ELF3 splicing, and to determine whether this $Alu_{kwd}$ might be linked to the cytoplasmic intron retention discussed in Example 1. Accordingly, we chose to study peripheral blood mononuclear cells from breast cancer patients to determine whether there might be some global defect in splicing of ELF3 in otherwise normal cells from these patients.

This investigation resulted in the finding of intron retention of $Alu_{kwd}$ along with the GC3 fragment of intron 7 in cytoplasmic mRNA in PBMCs from women whose breast cancer pathology indicated the presence of ductal carcinoma in situ (DCIS), with or without invasive carcinoma. This aberrant retention of Alu and intron sequences was seen infrequently in most normal patients without breast cancer, and in other forms of breast cancer in which DCIS was not seen pathologically. The association of intron retention in PBMCs from DCIS patients has not been previously described. This particular form of breast pathology (i.e., DCIS) appears to be a major precursor in the development of invasive ductal carcinoma. The finding of ELF3 gene expression in PBMCs is also a novel finding for this gene that heretofore was believed to be expressed only in epithelial cells and not in lymphoid tissue (Tymms et al., 1997; Chang et al., 1997; Andreoli et al., 1997; Choi et al., 1998; Chang et al., 1999; Oettgen et al., 1999; Oettgen et al., 1997a; Brembeck et al., 2000; Chang et al., 2000).

Materials and Methods

Human tumor cell lines. Human breast cancer and matched normal cells lines (K151, K234 and K259) were established in our laboratory as described in Example 1, and maintained with 20% FBS-1640 media in T75 flasks at 37° C. in a 5% $CO_2$ atmosphere. MCF-7 (human breast cancer), U-937, (human histiocytic lymphoma), Jurkat (human T cell leukemia) and C33-A (human cervical cancer) cell lines were obtained from the American Type and Tissue Culture Collection (ATCC) and routinely maintained in RPMI 1640 (GIBCO-BRL) supplemented with 10% FBS at 37° C. in a 5% $CO_2$ atmosphere.

Genomic DNA Walking. DNA was isolated from cells using the QIAamp DNA blood kit (Qiagen Inc.). The Universal GenomeWalker kit (Clontech Laboratories, Inc.) was used for genomic DNA walking based on the instructions provided by the manufacturer. Briefly, genomic DNA was digested by DraI EcoRV, PvuII and StuI overnight and ligated with the adaptor from the kit. The uncloned, adaptor-ligated genomic DNA fragments were used as genomic-walker libraries for polymerase chain reaction (PCR) amplification. Primary PCR used the outer adaptor primer provided in the kit (AP1) coupled with either sense (GC3 DF)(SEQ ID NO:20) or antisense (GC3UPF)(SEQ ID NO:18) primers derived from known sequences for downstream and upstream walking respectively. The primary PCR mixture was then diluted and used as a template for nested PCR with a nested adaptor primer from the kit (AP2) combined with either nested sense (GC3DN)(SEQ ID NO:21) or antisense (GC3 UPN)(SEQ ID NO:19) primers. The GC3 DD (SEQ ID NO:32) primer was used for further down-stream walking in the first and nested PCR reaction. The sequences of the primers are listed in Table 1, in Example 1). Each of the DNA fragments that begin in a known sequence at the 5' end of antisense primers (upstream walking) or the 3' end of sense primers (downstream walking) and which extend into the unknown adjacent genomic DNA were cloned and sequenced as described below.

Sequencing and GenBank searching. The DNA fragments from genomic walking were gel purified by using the Wizard PCR preps DNA purification system (Promega Corp.) and cloned in pPCR-script Amp SK(+) cloning vector by using the PCR-Script Amp Cloning Kit (Stratagene). Plasmids were purified using the Plasmid Miniprep Kit (Bio-Rad Laboratories), and sequenced by T3 and T7 primers in both directions. For PCR product sequencing, the DNA fragments from the PCR reaction were diluted 1:10 with distilled $H_2O$ and sequenced with primers used in the PCR reaction. The sequencing was done at the North Shore University Research Institute (New York) DNA Sequencing Facility using an ABI Prism 377 DNA Sequencer. Nucleotide BLAST of the National Center for Biotechnoloy Information was used for searching for homologous sequences (Altschul et al., 1990; Gish and States, 1993; Altschul et al., 1997).

RNA extraction. In this study, all RNA extraction was carried out with the High Pure RNA isolation kit (Roche, Indianapolis, Ind.) according to the manufacturer's protocol. Any co-purified DNA was ultimately digested with DNase I. All RNA isolates were tested for genomic DNA contamination by PCR amplification before reverse transcription to cDNA. Isolation of nucleic RNA and cytoplasmic RNA was performed according to a basic protocol (Ausubel, 1995) with slight modification. Briefly, freshly prepared cell pellets were suspended in 200 µl of lysis buffer containing the nonionic detergent P-40 for 5 minutes on ice. The lysates were centrifuged at 2000 rpm/min to separate a cytoplasmic fraction (supernatant) and a nuclear fraction (cell pellet). The supernatant containing the cytoplasmic extract was transferred to a fresh tube. The pellet, which consisted of nuclei, was resuspended in 200 µl of PBS buffer for nuclear RNA isolation. The supernatant was used for cytoplasmic RNA isolation after further centrifugation for 2 min at 12,000 rpm to further remove any contaminating nuclei. The RNA from the separated cytoplasm and nuclei were prepared by using the same protocol as total cellular RNA isolation. RNAase and DNAase I digestion analyses were performed to assure that there was no DNA contamination of RNA isolates prior to conversion to cDNA. Approximately 500 ng of total RNA was digested with either 5 µg of RNAase or 200 U of RNAase-free Dnase I (Roche, Indianapolis, Ind.) at 37° C. for 20 min. After incubation, RNAase or DNAase I was inactivated by incubation at 70° C. for 10 min. The reaction mixtures were subjected to the same procedure as RNA isolation.

Preparation of cDNA by RT-PCR and PCR. cDNA was synthesized from purified total RNA at 42° C. in the presence of oligo d(T)16 with MuLV-reverse transcriptase with the Perkin Elmer RNA PCR kit. Eight (8) paired cDNAs from breast cancer tissues and matched normal breast tissues were prepared as described in Example 1. PCR amplifications (25 µl) were performed in PCR buffer containing 0.2 µM of each primer, 2.5 µl of the first-strand cDNA samples or 10-50 ng of DNA (for PCR), 200 µM of each dNTP and 1 U of Platinum Taq DNA polymerase (Gibco). When the PCR products were used for sequencing, reading proof PWO DNA polymerase (Roche) mixed with AmpliTaq DNA polymerase (Perkin Elmer) (1:5 ratio) was used. Primers GC3 S (SEQ ID NO:16) and GC3 AS (SEQ ID NO:17) were used to amplify 202 bp of intron 7 of ELF3; primers INSE-S (SEQ ID NO:33) and INSE-AS (SEQ ID NO:34) were used to amplify a 451 bp sequence of intron 8 of ELF3 if Alu$_{kwd}$ is inserted, or a 136 bp DNA fragment if Alu$_{kwd}$ is not inserted (Table 1). Touch down PCR was used in PCR reactions to improve the specificity (Don et al., 1995; Roux, 1995). The conditions of touch down PCR for GC3 and β-actin amplification were as follows: Initial denaturation at 94° C. for 3 min followed by 10 cycles each of denaturation for 1 min at 94° C., primer annealing for 1 min at 62° C. and extension for 1 min at 72° C., followed by 25 cycles of denaturation for 1 min at 94° C., primer annealing for 1 min at 57° C., extension for 1 min at 72° C. and then final extension for 10 min at 72° C. For Alu$_{kwd}$ amplification the annealing temperature was at 64° for 10 cycles and 620 for the following 25 cycles. The amplified products were separated by electrophoresis on 1.5% agarose gels containing ethidium bromide in TAE buffer (40 mM Tris-acetate, 1 mM EDTA). The gel was photographed under UV light with Polaroid 677 film.

Clinical Material. After informed consent, whole blood was collected in EDTA tubes from breast cancer patients at North Shore Hematology/Oncology Associates (New York), a general medical oncology group practice. They were selected only by a diagnosis of breast cancer and willingness to consent to this study. The patient charts were retrospectively reviewed for pathological reports, staging, and demographic information. All clinical information was obtained without knowledge of the laboratory findings. PBMCs were isolated from whole blood by Ficoll-metrizoate (Lymphoprep, Nyegard, Oslo) density gradient centrifugation. Cell pellets were preserved at −70° C. for DNA and RNA isolation. PBMCs from 20 unknown blood donors were purchased commercially.

Results

Figure 11:
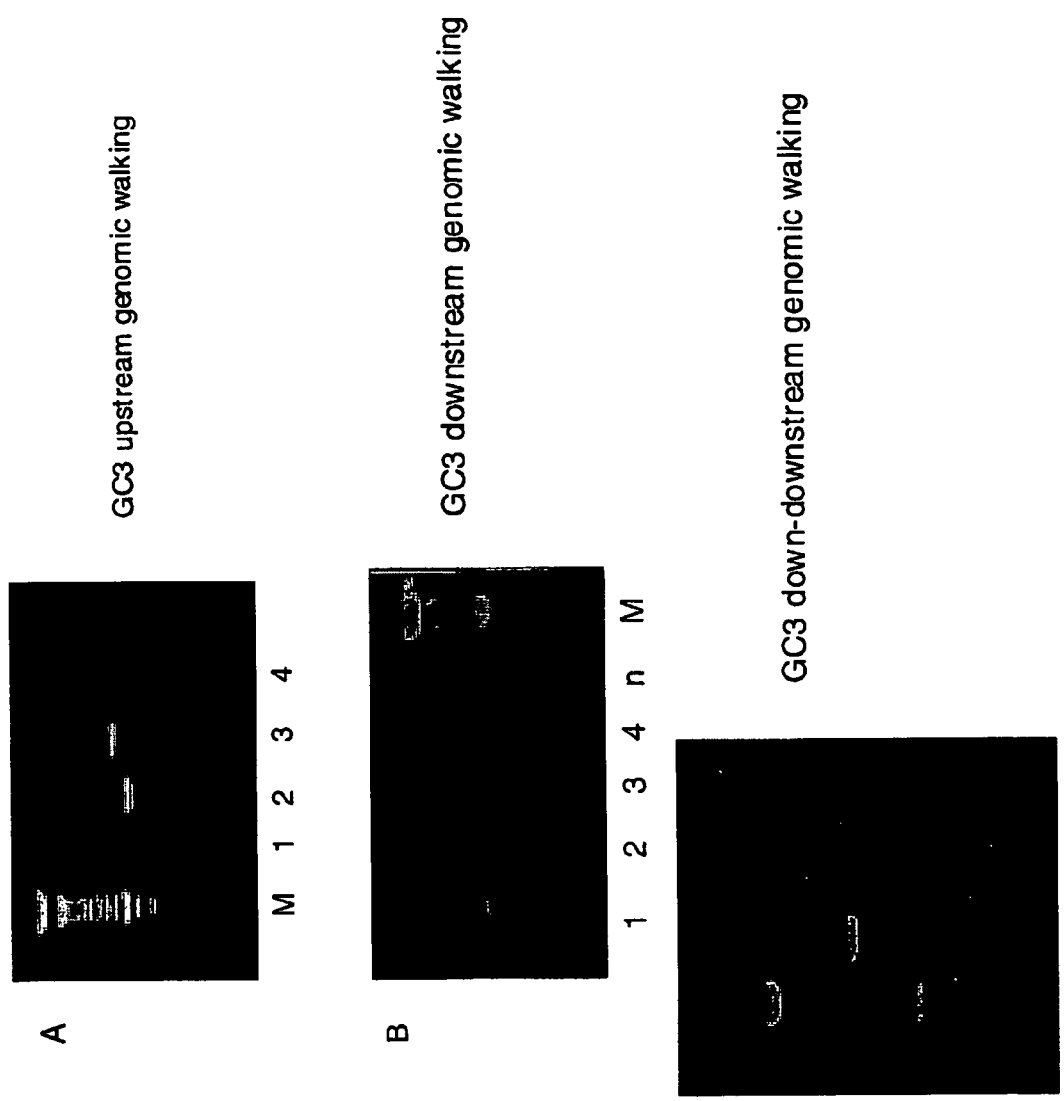
FIG. 11 shows gels of electrophoresed PCR products evaluating GC3 presence in genomic walking steps. Panel A. Upstream walking; Panel B. Down-stream walking; Panel C. Down-down stream walking. Lane M: 100 bp DNA ladder. Lane 1. DraI library; Lane 2. StuI library; Lane 3: PvuII library; Lane 4: EcoRV library.

Antisense insertion of a unique 315 bp Alu element within intron 8 of the ELF3 gene. We have shown that a fragment (GC3) (SEQ ID NO:11) of intron 7 of the ELF3 gene appeared as a difference in representational difference analysis (RDA) performed on a breast cancer cell line (tester) and a normal cell line (driver) prepared from the same neoplastic breast cancer effusion (Example 1). More importantly, intron 7 (GC3) was shown to be retained in the cytoplasmic ELF3 mRNA which was demonstrated by RT-PCR, and confirmed by cDNA sequencing. In order to search for any mutation or insertion near the intron 7 area which may have contributed to the retention of this intron in mRNA, genomic walking libraries were constructed from genomic DNA isolated from K151 breast cancer cell lines as described in Materials and Methods. Primers were designed based on the GC3 DNA sequence derived from K151 breast cancer cell lines for up-stream walking (GC3 UPF [SEQ ID NO:18] and GC3 UPN [SEQ ID NO:19]) and down-stream walking (GC3 DF [SEQ ID NO:20] and GC3 DN [SEQ ID NO:21]) (Table 1). DNA fragments from StuI and PvuII digested genomic walking libraries were produced for upstream walking. The sequence analysis of the 529 bp DNA fragment from the StuI library showed 98% homology to the ELF3 gene from nt 7022 to nt 7511. The 659 bp DNA fragment from the PvuII library showed 94% homology to the ELF3 gene nt 6892 to 7511. In the downstream walking library, a DNA fragment from the DraI library was predominant. The sequence revealed this to be a 629 bp DNA fragment with 96% homology to the ELF3 gene from nt 8003 to nt 8632. The next 40 bp sequence began with an A-enriched region, without homology to the ELF3 gene. To define this area more extensively, further downstream walking was carried out by using a primer (GC3 DD) (SEQ ID NO:32 located in nt 8569 to 8597 of ELF3. Another ~950 bp DNA fragment was produced in the StuI library by this further downstream walking. Sequence analysis revealed that this DNA fragment contained the sequence from nt 8569 to 9228 of the ELF3 gene. However, there was an antisense insertion of a unique 315 bp Alu element (SEQ ID NO:13) (designated Alu$_{kwd}$) within intron 8 between nucleotides 8762 and 8763 of the ELF3 gene which does not exist in the published ELF3 gene sequence deposited by Chang et al. (AF110184) (SEQ ID NO:1). This insertion occurs at the end of a 121 bp Alu region just after a 17 bp repeat from nt 8745 to nt 8762 (Appendix, under SEQ ID NO:13). This insertion is within intron 8 of the ELF3 gene, an area important for the Ets transcription regulation function of this gene (Tymms et al., 1997; Chang et al., 1997). The Alu$_{kwd}$ sequence provided as SEQ ID NO: 13 is only 85% homologous to any known Alu sequences deposited in GenBank. The genomic walking results and the Alu$_{kwd}$ insertion site results are summarized in FIGS. 11 and 20.

Figure 12:
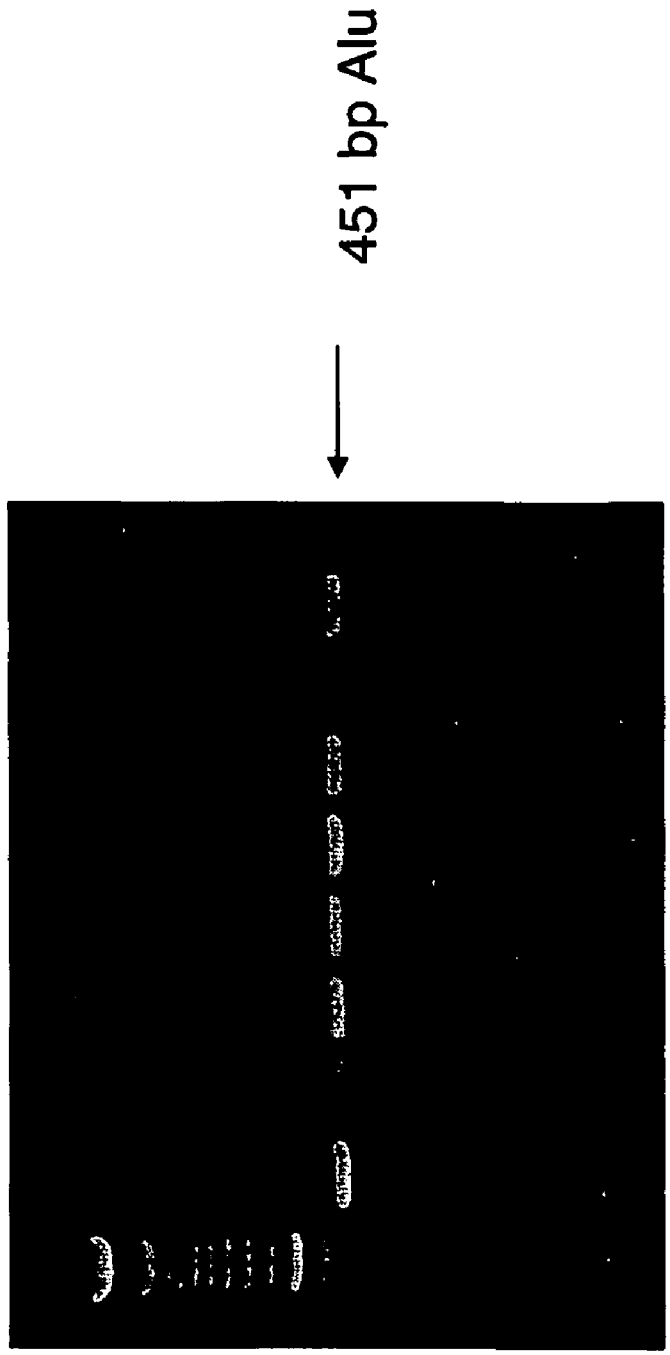
FIG. 12 shows a gel of electrophoresed PCR products evaluating the presence of the 315 bp $Alu_{kwd}$ sequence exemplified herein, in normal and breast cancer patients. The DNA from breast cancer cell lines (K151T, K234T and K259T), normal cell lines from patient with breast tumor (K234 N) and normal cells from donors without breast cancer (donor J and donor S) were amplified with $Alu_{kwd}$ primers. The 451 bp DNA fragment was amplified in all samples. A plasmid containing the $Alu_{kwd}$ DNA fragment from K151 tumor cells was used as a positive control.

To determine whether the antisense Alu$_{kwd}$ element insertion also exists in other breast cancer cell lines, breast cancer tissues or normal cells, another pair of primers (INSE-S [SEQ ID NO:33] and INSE-AS [SEQ ID NO:34]) were designed, which amplify a 451 bp DNA fragment in intron 8 of ELF3 where Alu$_{kwd}$ was found, flanked by normal intron 8 sequences, as shown in Appendix, under SEQ ID NO:14. PCR analysis was carried out using these primers on the DNA from breast cancer cell lines K151, K234 and K259, on the matched CD3$^+$ T lymphocytes derived from K234, and on normal donor PBMCs. This 451 bp DNA fragment was produced in all the tested samples. A ~140 bp DNA fragment was also observed, especially in the DNA isolated from K151 cancer cells (FIG. 12). This result suggests that Alu$_{kwd}$ is present both in breast cancer tissue and cultured cells from breast cancer patients, as well as in their normal PBMCs. DNA sequence analysis from the 451 bp PCR products reveals 100% homology to the sequence derived from genomic DNA walking, in which the 315 bp antisense Alu$_{kwd}$ sequence was inserted between nt 8672 and 8673 of the ELF3 gene. There was no difference in the DNA sequence found in the breast cancer cells, matched normal cells and PBMCs. The ~140 bp DNA fragment seen in the K151 cancer cells and some other samples indicated the presence of the ELF3 genomic DNA without the Alu$_{kwd}$ insertion, suggesting heterozygosity in these patient's ELF3 gene with one gene product missing the antisense Alu$_{kwd}$.

Figure 13:
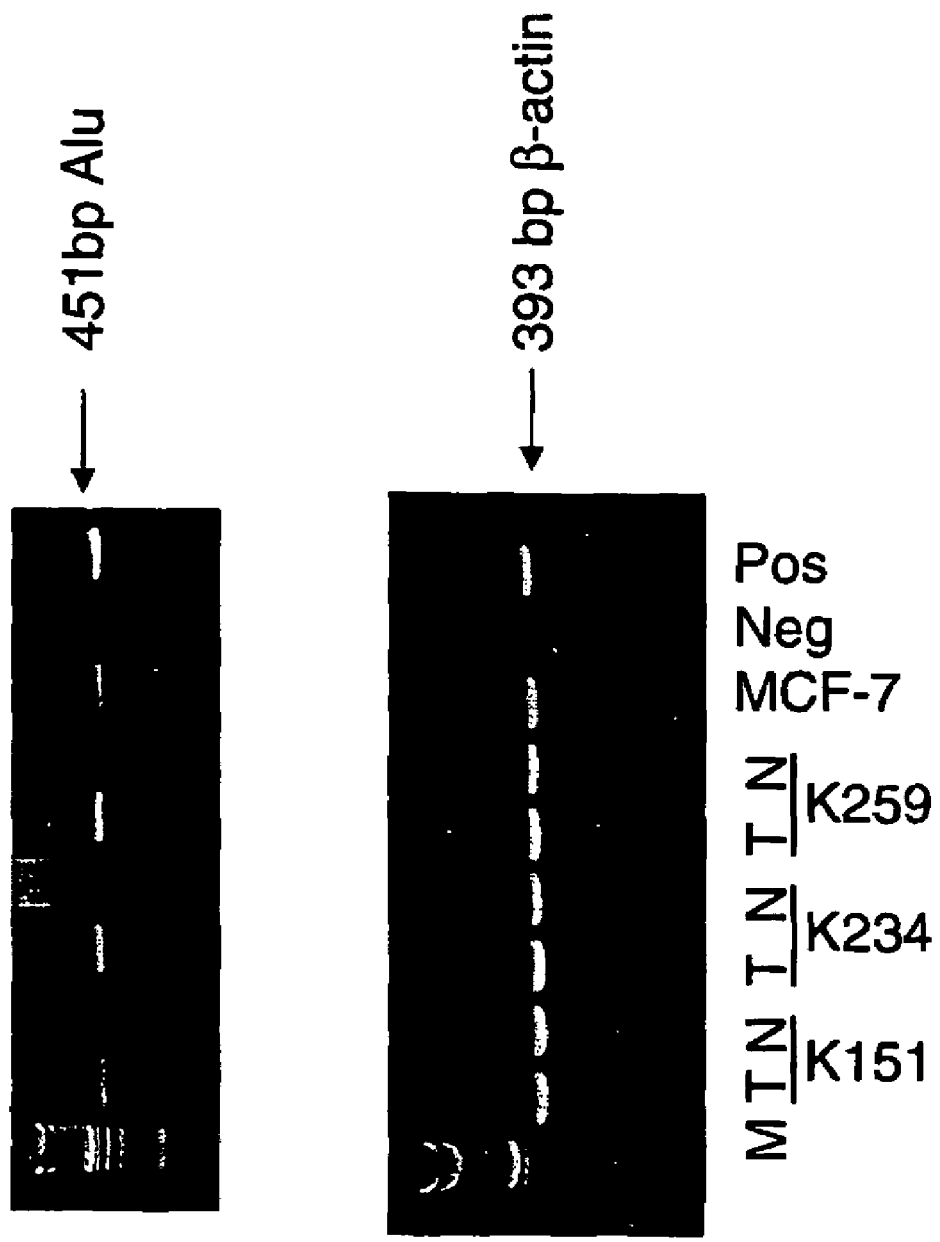
FIG. 13 shows gels of electrophoresed PCR products establishing $Alu_{kwd}$ retention in mRNA of breast tumor cell lines, but not normal cells. cDNA from K151 and K234 breast tumor and matched normal cell lines (lanes K151 and K234 T and N, respectively); K259 breast tumor cell line and donor 1 PBMC (lane K259-T and N, respectively); and MCF-7 breast cancer cell line were amplified by Alu primers (A) and β-actin primers (B). $Alu_{kwd}$ was present in mRNA from all breast tumor cells and no normal cells. β-actin presence in similar amounts in all samples except the negative control indicated RNA integrity and equivalent quantity in all of the samples tested.
Figure 14:
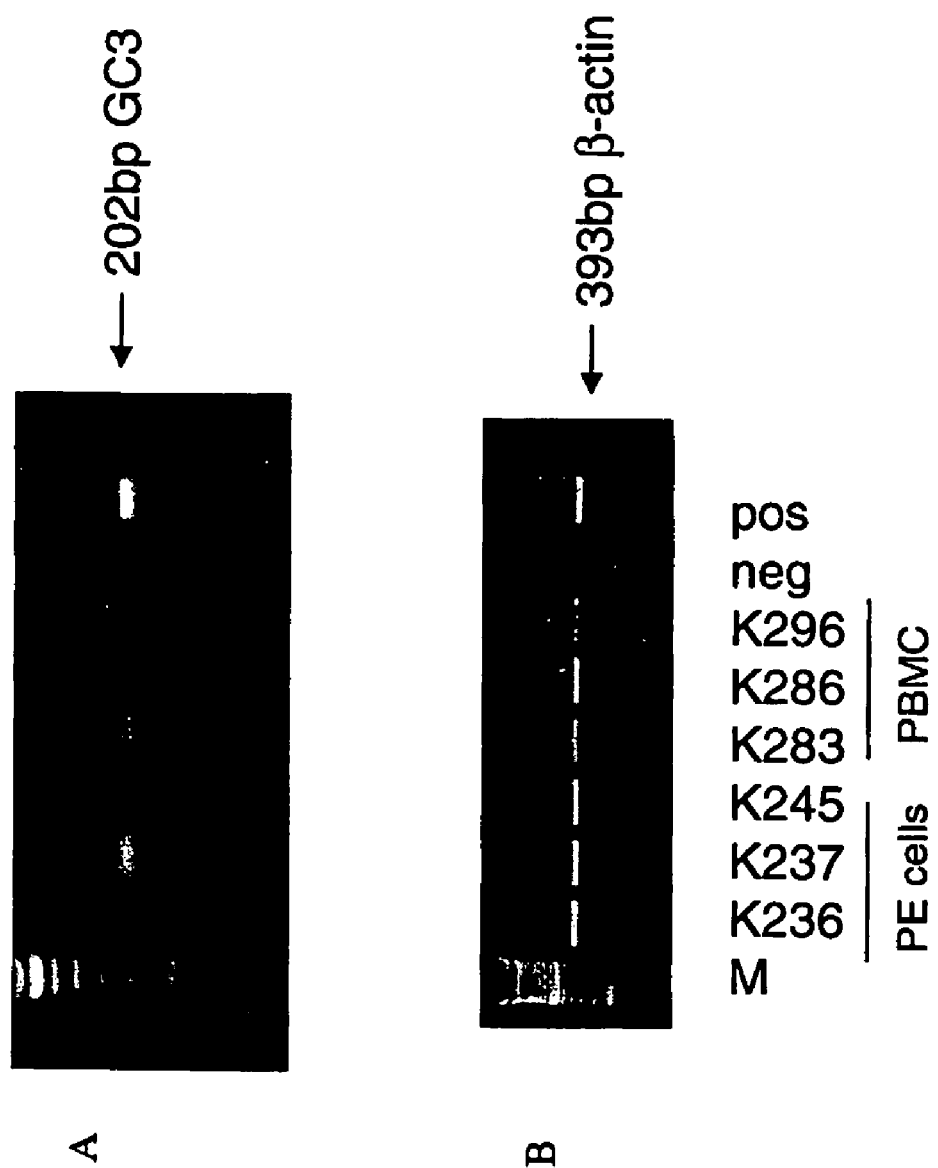
FIG. 14 shows gels of electrophoresed PCR products evaluating ELF3 intron 7 retention in mRNA in peripheral blood mononuclear cells (PBMC) from breast cancer patients with clinical remission. The mononuclear cells from pleural effusion (PE cells) in the late stage of breast cancer patients and PBMC in the remission period of breast cancer patients were used for RNA isolation. Synthesized cDNA was amplified with GC3 primers for intron 7 retention (Panel A) and β-actin primers for RNA integrity and quality control (Panel B). Intron 7 retention occurred in 2 of 3 cell preparations from pleural effusion of late stage of breast cancer patients and in 1 of 3 PBMC from early stage of breast cancer with clinical remission.

Retention of Alu$_{kwd}$ in ELF3 mRNA in breast cancer cells. A cDNA library was constructed from breast cancer cell lines and normal cell lines as previously described. This library was screened with primers made from the same Alu primers as in the PCR reaction to see if Alu$_{kwd}$ was expressed in these cells in a fashion similar to GC3 (intron 7) described in Example 1. We included a cDNA library from the well-studied human breast cancer cell line MCF-7 cell. The results are shown in FIG. 13. Alu$_{kwd}$ expression was present only in 4 breast cancer cell lines (K151, K234, K259 and MCF-7) but not in matched normal cell lines.

Figure 16:
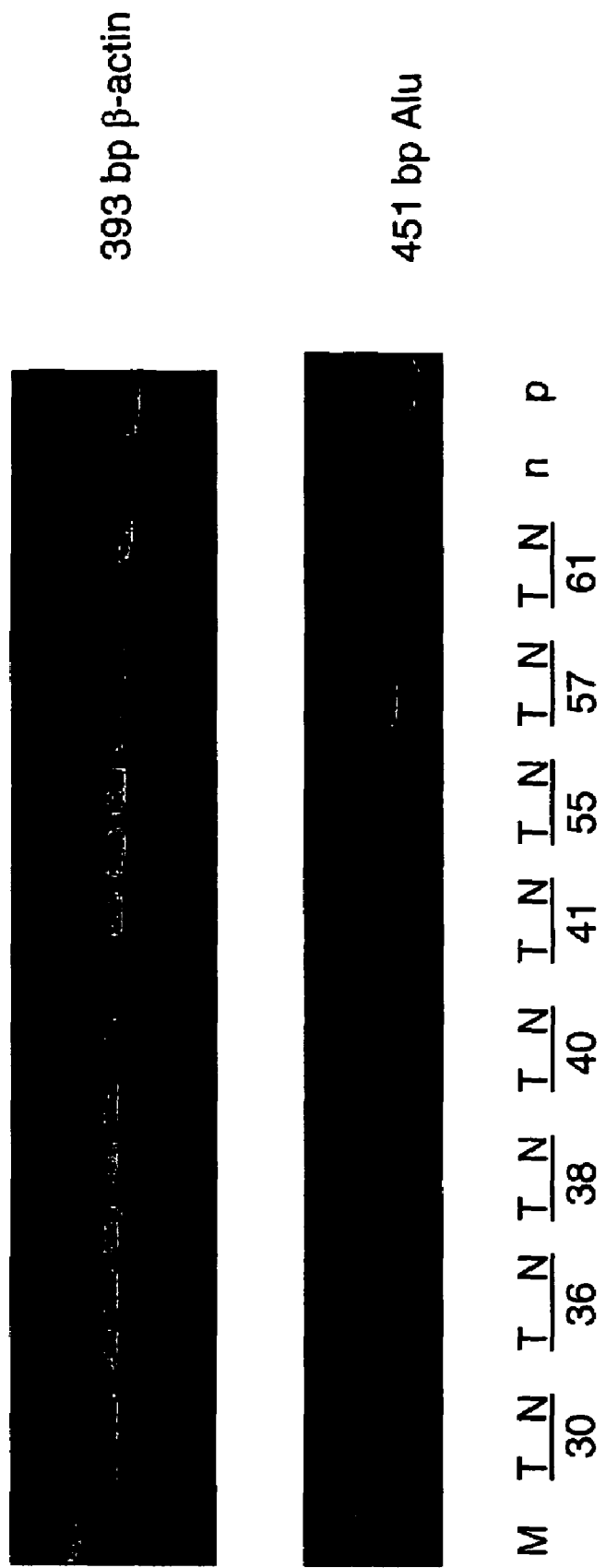
FIG. 16 shows gels of electrophoresed PCR products establishing that $Alu_{kwd}$ is present in retained intron 8 in ELF3 mRNA of breast tumor tissues but not matched normal tissues. cDNA from 8 sets of breast tumor and matched normal tissues were amplified by Alu$_{kwd}$ primers. Alu$_{kwd}$ was present in ELF3 mRNA of 5 of 8 breast tumor tissues and 0 of 8 normal tissues (Panel B). Integrity and quantity of RNA was checked in all samples by amplification of human β-actin (Panel A). Lane M, 100 bp DNA ladder; lane N and T represent normal tissue and breast tumor respectively. The patient ID numbers are below the N and T lanes. DNA from K151 tumor cells was used for a positive control (lane p); ddH$_2$O was the negative control (lane n).

Contamination with genomic DNA during RNA isolation may have resulted in contamination of our cDNA libraries. Such DNA would be amplified in the highly sensitive RT-PCR technique we used in our study. In order to exclude the possibility that the PCR products might result from amplification of contaminating genomic DNA in our RNA isolates, DNAase I and RNAase digestion was performed on the total RNA preparation from the K151 cancer cell line before cDNA synthesis by MuLV reverse transcriptase. The purified RNA after digestion was reverse transcribed to cDNA. In these studies, β-actin and Alu$_{kwd}$ amplifications were not detected in the RNAase digested RNA sample, but were present in the RNA sample after DNAase I treatment. This indicates that $Alu_{kwd}$ expression in the breast cancer cell lines was not the result of genomic DNA contamination and that $Alu_{kwd}$ was retained in mRNA isolates from breast cancer cell lines. We also tested for the presence of $Alu_{kwd}$ using the $Alu_{kwd}$ primers in 8 paired cDNAs prepared from human breast cancer tissue and matched normal tissues. The result is shown in FIG. 16. The 451 bp $Alu_{kwd}$ containing DNA fragment was produced in 5 of 8 breast cancer tissues (62.5%), but was not found in the matched normal tissues even though β-actin was expressed equally in all tissues.

Figure 17:
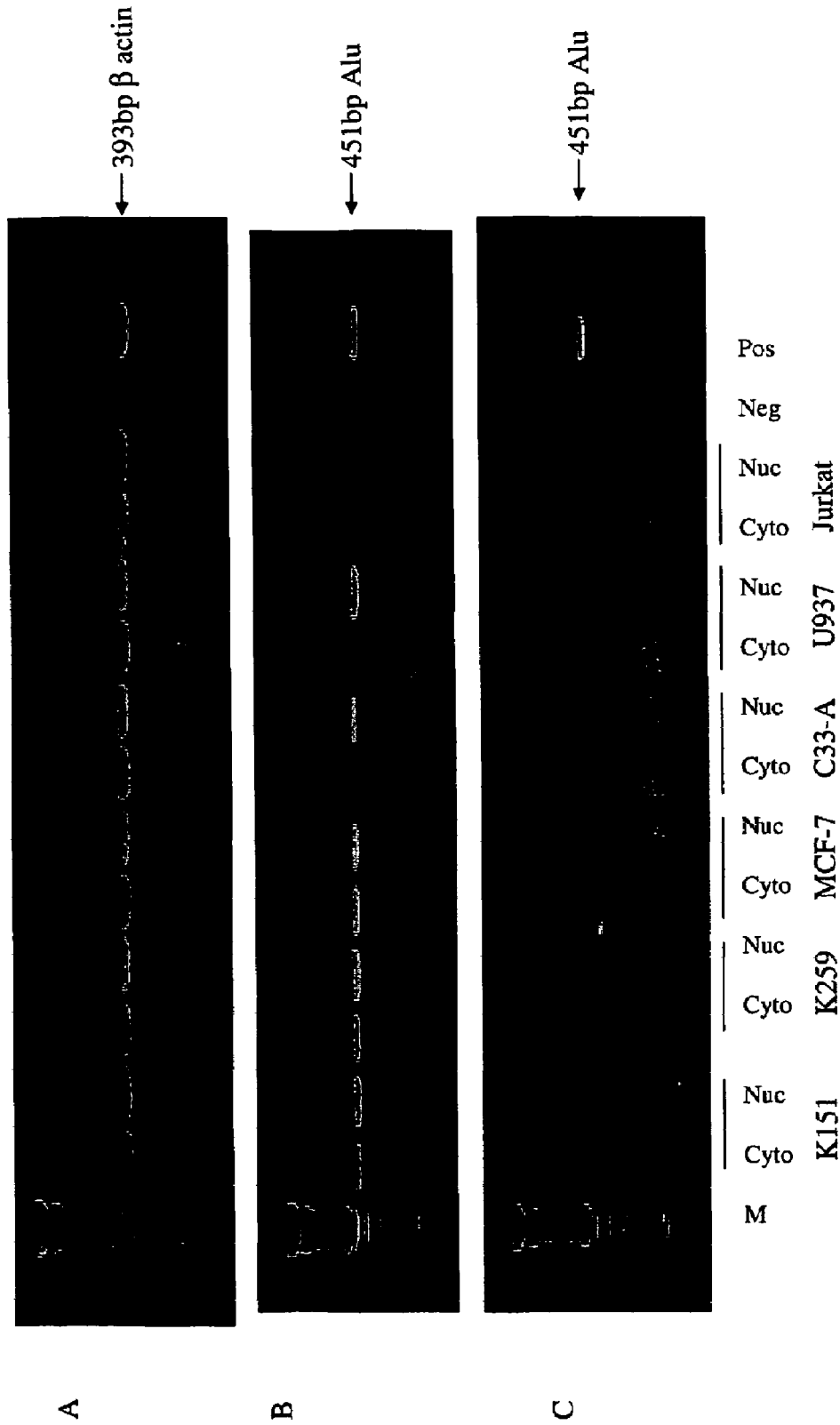
FIG. 17 shows gels of electrophoresed PCR products establishing the presence of Alu$_{kwd}$ expression in cytoplasmic and nuclear RNA in human breast cancer cell lines. Nuclear and cytoplasmic RNA was purified from human breast cancer cell lines K151, K259 and MCF-7, human cervical carcinoma cell lines C33-A, human histiocytotic lymphoma cell lines U-937, and human acute T cell leukemia cell line Jurkat. Integrity and quantity of RNA was checked in all samples by amplification of human β-actin (Panel A). Alu$_{kwd}$ was present in cytoplasmic and nuclear RNA from human breast cancer cell lines K151, K259 and MCF-7, and in C33-A and U-937 nuclear but not cytoplasmic RNA, and was absent in Jurkat cytoplasmic and nuclear RNA (Panel B). Negative Alu$_{kwd}$ PCR results in the same RNA isolation run in the same test demonstrated there were no DNA contamination in these RNA isolation (Panel C).
Figure 18:
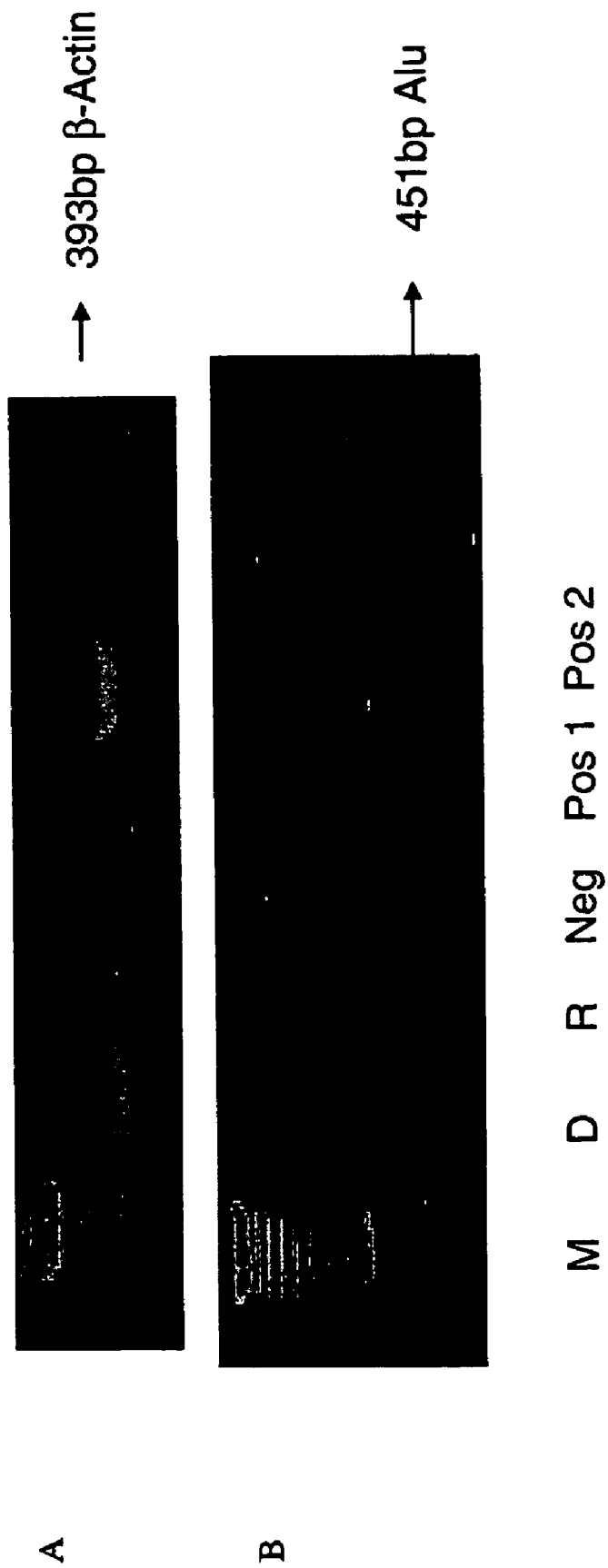
FIG. 18 shows gels of electrophoresed PCR products demonstrating that the Alu$_{kwd}$ and β-actin product was abolished by RNase digestion of RNA but not by DNase I digestion. Total cellular RNA prepared from the K151 tumor cell line was subjected to DNase I (lane D) and RNase (lane R) digestion prior to cDNA synthesis. RT-PCR was performed using β-actin primers (Panel A) and Alu$_{kwd}$ primers (Panel B). The expected PCR product was produced from the DNase I-digested RNA isolate but not from the RNase-digested RNA isolate, when both the β-actin and Alu$_{kwd}$ primers were used. The result verifies that the 415 bp Alu$_{kwd}$ product is generated by amplification of mRNA; contamination with genomic DNA is excluded. An RNA isolation from the K151 tumor cell line without digestion was used as positive control for RT-PCR (pos 1); DNA from the K151 tumor cell was used as a positive control for the PCR reaction (pos 2); ddH$_2$O was used as a negative control in the RT-PCR reaction (neg).

To verify that $Alu_{kwd}$ is retained in the cytoplasmic mRNA, RNA was purified from isolated nuclear and cytoplasmic fractions of K151, K259 and MCF-7 human breast cancer cell lines as described in Materials and Methods. Human histiocytic lymphoma cell line U-937, human T cell leukemia cell line Jurkat, and human cervical carcinoma cell line C-33A were similarly analyzed. RT-PCR results showed that the ~451 bp $Alu_{kwd}$-containing PCR product was generated in the cytoplasmic and nuclear RNA of K151, K259 and MCF7, but was present only in the nuclear RNA from C33-A and U937. No PCR product was produced in either the nuclear or cytoplasm RNA from Jurkat (FIG. 17B). The same amount of RNA prepared after DNAse digestion was not subjected to reverse transcription but was instead tested by PCR using the Alu primers. There was no amplification of the 451 bp DNA fragment in either the nuclear or cytoplasmic fraction (FIG. 17C). These results indicate that the 451 bp $Alu_{kwd}$-containing intron 8 fragment is retained in the cytoplasmic mRNA of human breast cancer cell lines K151, K259 and MCF7 and is not due to genomic contamination of RNA prior to preparation of cDNA. The 393 bp β-actin DNA could be found in all cDNA samples by RT PCR, demonstrating the integrity of the RNA and showing that similar amounts of RNA were present in each sample (FIG. 17A).

Association of intron 7 and intron 8 $Alu_{kwd}$ retention of ELF3 in PBMCs from patients with ductal carcinoma in situ (DCIS). As retention of intron 7 and intron 8 $Alu_{kwd}$ appeared to be exclusively in breast cancer tissues and cancer cell lines, we explored the possibility that these findings might be extrapolated to the peripheral blood, as a useful marker for breast cancer. cDNA libraries were prepared from peripheral blood mononuclear cells (PBMCs) and these libraries were screened for GC3 (intron 7) retention and for $Alu_{kwd}$ retention. The pathological diagnoses of these patients were unavailable during the analysis of the samples for intron retention. RNA was extracted from these cells as described above, and cDNA libraries were prepared. All RNA isolates were tested for genomic DNA contamination using the GC3 and β-actin primers. Only one sample demonstrated genomic contamination and it was not used in our analysis. Commercially purchased lymphocytes from normal healthy adult donors were similarly analyzed. The cDNA libraries from these cells were tested using both the GC3 primers for analysis of intron 7 retention and the Alu primers for intron 8 $Alu_{kwd}$ retention.

After analysis, charts and records were reviewed to determine the type of breast cancer present and to determine the stage of disease. Pathology reports were used to determine the type of cancer and were read by different pathologists at the time of biopsy and independent of this study. These reports indicated that many specimens were from patients with ductal carcinoma in situ (DCIS) either alone or in the presence of invasive ductal carcinoma (DCIS+/−IDC). Invasive ductal carcinoma (IDC) was sometimes reported without mentioning DCIS. Some patients had lobular carcinoma (ILC) with or without lobular carcinoma in situ (LCIS), and/or DCIS +/−IDC. In 2 patients adequate pathological descriptions could not be found and these samples were not used.

Figure 15:
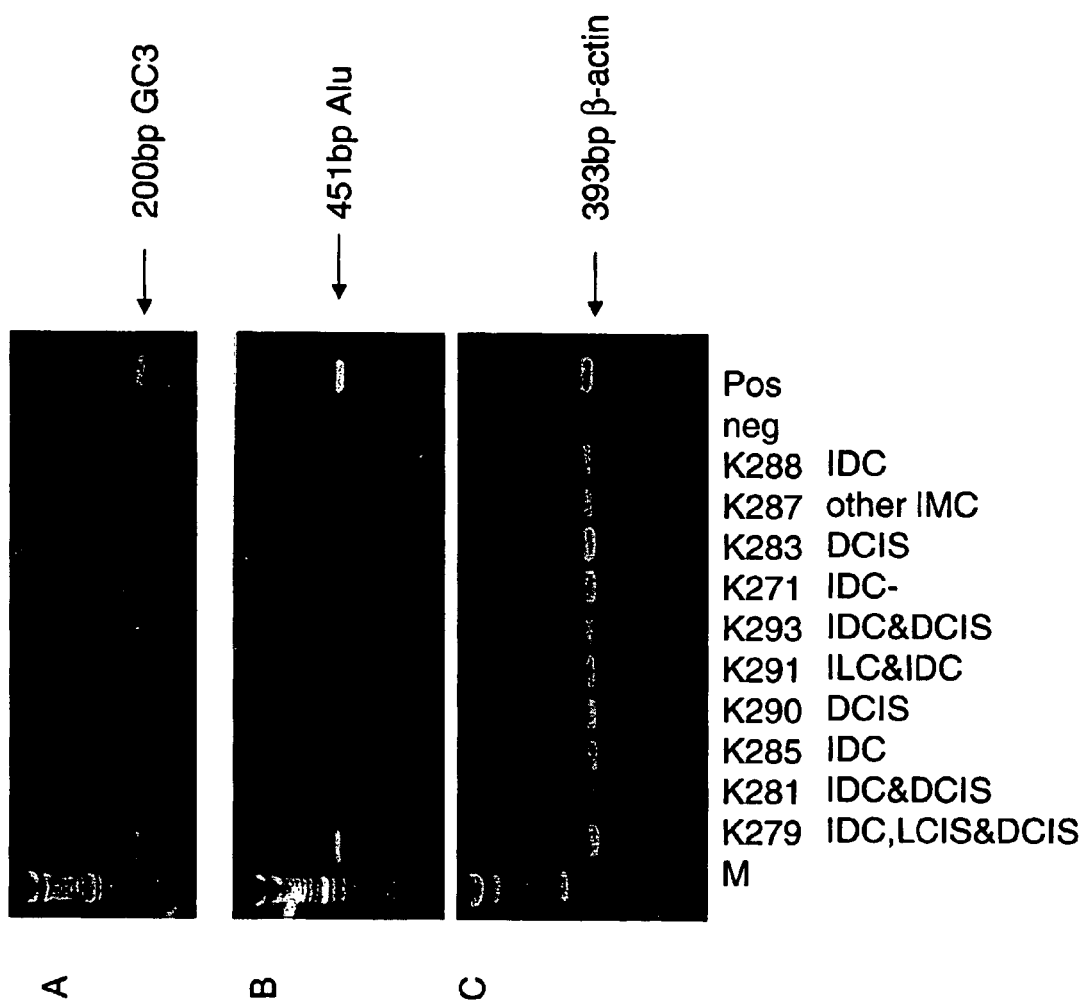
FIG. 15 shows gels of electrophoresed PCR products establishing the association of ELF3 mRNA multiple intron retention in PBMC with the human breast cancer DCIS. cDNA from 10 breast cancer patients were amplified with GC3 primers to test for intron 7 retention (Panel A), $Alu_{kwd}$ primers to test for intron 8 retention (Panel B), and β-actin primers for RNA quality control (Panel C). The results showed intron 7 retention occurred in 4 of 5 PBMC from patients with breast cancer with DCIS subtype and 0 of 5 PBMC from patients with breast cancer with other subtypes. Intron 8 $Alu_{kwd}$ retention occurred in PBMC from 3 of 5 patients with breast cancer with DCIS subtype and 0 of 5 patients with other subtypes of breast cancer. K151 5' RACE cDNA library served as a positive control in all assays.

Representative gels are shown in FIG. 15, and a summary of the results is presented in Table 2. In patients whose report indicated the presence of DCIS with or without other forms of invasive cancer, intron 8 $Alu_{kwd}$ retention was seen in 10/27 (37%) while it was present in only 3/25 (12%) patients who did not have a pathological description of DCIS. This difference was statistically significant at $p \leq 0.01$ by the chi square test. $Alu_{kwd}$ retention was not seen in any of the 20 normal blood donors (Table 2). The same samples when screened for GC3 retention showed this intron to be retained in 13/27 (48%) of DCIS+/−IDC while it was present in only 3/25 (12%) cancers without a description of DCIS. This difference was statistically significant $p \leq 0.01$. GC3 retention was present in on 2/20 normal PBMCs but these bands were very faint with insufficient DNA to adequately sequence to be certain these represented GC3 DNA. The association of $Alu_{kwd}$ and/or GC3 with DCIS IDC was statistically different from controls ($p \leq 0.01$). All patients showing $Alu_{kwd}$ retention also showed GC3 retention.

TABLE 2

Summary of clinical results

| | Breast cancer with DCIS related subtype (n = 21) | Breast cancer with non-DCIS related subtype (n = 28) | Normal donors (n = 20) |
|---|---|---|---|
| GC3 Retention (%) P value | 13/27 (48.15%) vs. non-DCIS <0.01 vs. normal <0.01 | 3/25 (12%) | 2/20 (10%) |
| Alu retention (%) P value | 10/27 (37.04%) vs. non-DCIS = 0.05 vs. normal <0.05 | 3/25 (12%) | 0/20 (0%) |

Figure 19:
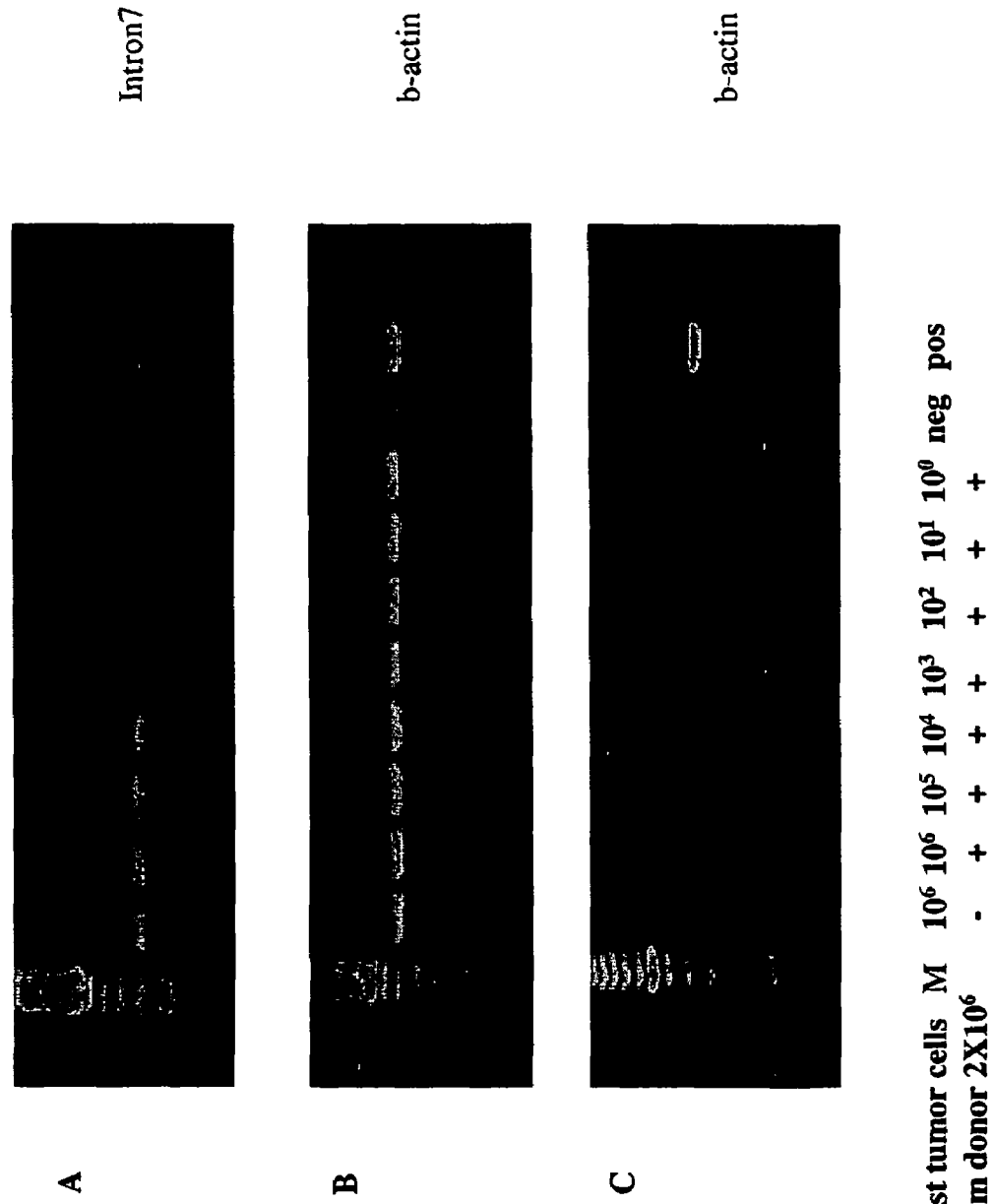
FIG. 19 shows gels of electrophoresed PCR products demonstrating ELF3 mRNA retention of intron 7 in breast tumor cells. Various concentrations of intron 7-expressing cells (K259 tumor cell lines) were spiked into 2×10$^6$ PBMC prepared from a normal blood donor. cDNA from those samples were amplified with GC3 primers for intron 7 expression (Panel A) or β-actin primers for RNA integrity and quality control (Panel B). In the same experiment, the RNA isolates were also amplified with β-actin primers to detect DNA contamination in those RNA isolates (Panel C). Negative (neg) and positive (pos) controls were ddH$_2$O and RNA from the K151 tumor cell line, respectively. Intron 7 retention was observed at a K259 breast tumor cell concentration from 10$^6$ to 10$^3$ per 2×10$^6$ normal cells. Positive β-actin expression in all samples that were reverse transcribed demonstrated equal amount of RNA input in RT-PCR reaction; negative β-actin expression in the RNA isolates that were not reverse transcribed ruled out the possibility of DNA contamination.

The Effect of Addition of Breast Cancer Cells to PBMCs on the Detection of ELF3 intron 7 (GC3). The presence of ELF3 expression in the form of intron retention could be the result of circulating breast cancer cells in the peripheral blood which were detected by our methodology. In order to understand the sensitivity of our detection system, we added 10 fold-increasing concentrations of GC3 expressing K259 breast cancer cells, from 1 cell up to $1 \times 10^6$ cells, into $2 \times 10^6$ PBMCs that did not demonstrate GC3 or $Alu_{kwd}$ retention. RNA was extracted from each dilution and 2 µl RNA (between 1-3 ng) was used for cDNA synthesis using methods described. These dilutions were tested for the presence of GC3 using GC3 primers which amplify 202 bp intron 7 of ELF3. As shown in FIG. 19, the correct PCR product was visible with a dilution of $1.0 \times 10^6$ to $1.0 \times 10^3$ per $2 \times 10^6$ PBMCs indicating an ability to detect at least 1 cancer cell in 2000 normal PBMCs. Many of the PBMCs which were tested for GC3 were from women who have been in remission from breast cancer for many years and/or from women who have been on therapy but were not considered to have active metastatic disease. This suggests that the presence of intron retention of GC3 or $Alu_{kwd}$ is not due to circulating breast cancer cells but due to some more basic abnormality, detectable in the PBMCs of women with breast cancer.

Discussion

Using cells, tissues, and cell lines from breast cancer patients, and applying gene walking technology, a unique novel Alu element in the ELF3 gene has been found. The Alu, dubbed $Alu_{kwd}$, is inserted in a reverse orientation into another Alu within intron 8 between positions 8762 and 8763. Two forms of intron 8 DNA exist in our cancer cell lines. One contains $Alu_{kwd}$ and another without this element, indicating heterozygosity of the ELF3 gene.

$Alu_{kwd}$ appears in cDNA in both human breast cancer cell lines and breast cancer tissue specimens. The presence of unspliced mRNA containing $Alu_{kwd}$ in the cytoplasm of the neoplastic cell lines is not due to genomic contamination of RNA prior to creation of cDNA libraries. The $Alu_{kwd}$ is also not found in normal breast epithelial cells or in a limited number of malignant cells from non-breast derived cell lines. Strikingly, PBMCs from 35.7% of breast cancer patients with DCIS, with or without invasion, express $Alu_{kwd}$ in their PBMCs. A fragment of intron 7 of the ELF3 gene, previously designated GC3, is similarly retained in the cytoplasm of 46.4% of the PBMCs from breast cancer patients with DCIS with or without invasion.

Alu elements are ubiquitous in the human genome, which contains 500,000 to 1,000,000 copies representing 5-10% of the total DNA. They can insert themselves into the genome by using "borrowed" reverse transcriptase (Schmid, 2000). They are generally not found within the coding region but have been found in introns and occasionally in non-translated regions of mRNA (Szmulewicz et al., 1998). Previously thought to be "junk DNA" derived from inactivated sequences, Alu cDNAs can insert themselves into genes where they can interfere with, or alter gene function, by interacting with promoters or enhancers as well as introns and exons. They have been shown to induce alternate splicing in some families with BRCA1 mutation.

It is unclear if $Alu_{kwd}$ interferes with splicing. Alu elements are generally spliced out of the final forms of mRNA. Finding retained $Alu_{kwd}$ in cytoplasmic mRNA of breast cancer cells and tissue, along with the previously described GC3 fragment of intron 7, evidence of a gross splicing defect is present in the ELF3 gene in breast cancer. The retention of introns 4, 5, 6, 7 and the Alu element in intron 8 also favors this assumption. This defect is not present in all breast cancer cell lines or tissue.

The expression of ELF3 is generally thought to occur only in epithelial cells. We have shown however that we can find unspliced mRNA of ELF3 which includes GC3 (intron 7) and the $Alu_{kwd}$ element within intron 8 in the PBMCs of patients with breast cancer, especially in those with DCIS with or without invasion, as opposed to all other diagnoses. It was not present in PBMCs from most normals or in patients whose pathological reports did not indicate DCIS. Its presence is apparently not due to circulating metastatic cancer cells, as most patients were in remission so it is unlikely that they had >1/2000 cancer cells/normal PBMCs, which is the limit of detection of cancer cells with abnormal intron retention in our system. This is evidence of an important ELF3 splicing error related to breast cancer. The ELF3 gene appears to be important in DCIS and may be associated with regulation of HER2/neu (Chang et al., 1997).

The presence of intron retention in the PBMCs of a certain cohort of cancer patients is consistent with a global splicing error in some patients with breast cancer, and may be due to some hidden viral element that interferes with splicing. If a putative virus is responsible in some way for breast cancer, it could be searched for using intron retention or $Alu_{kwd}$ as a marker for its presence, similar to the way reverse transcriptase was used as a marker to find the HTLV1 virus (Poiesz et al., 1980) and HIV-1 (Gallo et al., 1984). These findings open up a different approach to the epidemiology of breast cancer and provide new useful tools for the study of this disease.

EXAMPLE 3

Viral Induction of ELF3 mRNA Intron Retention and $Alu_{kwd}$

As established in the previous Examples, ELF3 intron 7 (GC3) and intron 8 (Alu) retention was only observed in certain breast cancer cells and tissues as well as in peripheral blood mononuclear cells (PBMCs) from about 50% of DCIS breast cancer patients. The hypothesis that a virus, specifically a retrovirus or a herpesvirus, may be involved in the cause of breast cancer has been proposed for a long time. To date no clear cut virus has been discovered although some have tried to implicate mouse mammary tumor virus and possibly EBV as a cause of human breast cancer. Therefore we evaluated whether virus infection could induce ELF3 intron 7 (GC3) retention in a cell line. Establishment of the induction of ELF3 intron retention by viral infection would establish that viral presence, particularly a virus associated with breast cancer, can be investigated by evaluating whether ELF3 introns are retained in mRNA. To this end we performed the following experiments.

RT-PCR was performed on RNA extracted from PBMCs of 8 HIV-1 infected patients, PBMCs of 1 HTLV-1 infected patient, and from 1 HTLV-1 infected T cell line. GC3 expression was not observed in any of these RNAs from these retrovirally-infected cells.

We next evaluated whether infection with any of 7 human herpesviruses could induce intron retention, by RT-PCR analysis of GC3 expression in RNA preparations from infected cells. Herpes simplex virus I (HSV 1), herpes simplex virus II (HSV2), Varicella zoster virus (VZV), Epstein Barr virus (EBV), cytomegalovirus (CMV), human herpes virus 6 (HHV6) and Human herpes virus 8 (HV-8) were the herpes viruses tested. Separate cultures of a MRC5 cell line were each inoculated with a laboratory strain of HSV1, HSV2, VZV and CMV. When the cytopathic effect (CPE) characteristic for each virus appeared, the infected MCR5 cells were collected, and cell pellets were kept at 90° C. EBV-transfected B cell lines, HHV6-infected cell line HSB2, and HHV8-positive cells from Kaposi's sarcoma cells were also used for this study. Uninfected MRC5 cell lines and HSB2 cell lines were used as normal controls. PCR of the RNAs without reverse transcriptase using GC3 primers, as in the previous examples, was performed to rule out DNA contamination.

In these studies, GC3 expression appeared only in the RNA extracted from EBV-infected cell lines. To confirm that EBV infection can induce ELF3 intron 7 (GC3) retention, further experiments were performed using EBV strain B95-8 (obtained from ATCC). This strain was used to infect the BJAB cells. BJAB is an EBV-negative B cell line that is also negative for intron retention of GC3. The cell pellets were prepared from EBV-infected BJAB cells at day 2, day 4, day 7, day 9, day 11 and day 14 after infection. BJAB without EBV infection was used as a control.

ELF3 intron 7 retention was produced on all EBV-infected BJAB cells from day 2 to day 14. There was no ELF3 intron 7 retention demonstrated in normal BJAB cell lines without EBV infection. These results indicate that EBV infection can induce ELF3 intron 7 retention in infected cell lines. This would suggest that an EBV-like virus or even EBV itself might play some role in the production of breast cancer. We have demonstrated that the cell lines described in the previous Examples that are derived from breast cancers do not show evidence of EBV infection when tested with appropriate EBV PCR primers. We thus believe that a novel virus may play some role in breast cancer and induce intron retention.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

Appendix—SEQ ID NO:s
SEQ ID NO:1 and SEQ ID NO:3—From GenBank Accession No. AF110184.
SEQ ID NO:1—ELF3 gene (annotated)—AF110184 and
SEQ ID NO:3—human ELF3 amino acid sequence alternative 1.
LOCUS AF110184 10772 bp DNA linear PRI 22-JUL-1999
DEFINITION *Homo sapiens* epithelium-restricted Ets protein ESX gene, complete cds.
ACCESSION AF110184
VERSION AF110184.1 GI:5565858
SOURCE human.
ORGANISM *Homo sapiens*
  Eukaryota; Metazoa; Chordata; Craniata; Vertebrata; Euteleostomi;
  Mammalia; Eutheria; Primates; Catarrhini; Hominidae; Homo.
REFERENCE 1 (bases 4802 to 9870)
  AUTHORS Chang, C. H., Scott, G. K., Kuo, W. L., Xiong, X., Suzdaltseva, Y., Park, J. W., Sayre, P., Erny, K., Collins, C., Gray, J. W. and Benz, C. C.
  TITLE ESX: a structurally unique Ets overexpressed early during human breast tumorigenesis
  JOURNAL Oncogene 14 (13), 1617-1622 (1997)
  MEDLINE 97275260
  PUBMED 9129154
REFERENCE 2 (bases 1 to 10772)
  AUTHORS Chang, C. H., Scott, G. K., Baldwin, M. A. and Benz, C. C.
  TITLE Exon 4-encoded acidic domain in the epithelium-restricted Ets factor, ESX, confers potent transactivating capacity and binds to TATA-binding protein (TBP)
  JOURNAL Oncogene 18 (25), 3682-3695 (1999)
  MEDLINE 99318560
  PUBMED 10391676
REFERENCE 3 (bases 1 to 10772)
  AUTHORS Chang, C. H., Scott, G. K. and Benz, C. C.
  TITLE Direct Submission
  JOURNAL Submitted (30 Nov. 1998) Hematology/Oncology, U.C.S.F., 505 Parnassus Ave., San Francisco, Calif. 94143-1270, USA

```
FEATURES      Location/Qualifiers
   source    1..10772
         /organism="Homo sapiens"
         /db_xref="taxon:9606"
         /chromosome="1"
         /map="1q32"
   misc_feature 34..622
         /note="similar to THC 213038"
   repeat_region 921..1524
         /rpt_family="Alu"
         /rpt_type=dispersed
   repeat_region 2978..3293
         /rpt_family="Alu"
         /rpt_type=dispersed
   CAAT_signal 4697..4702
         /evidence=not_experimental
   TATA_signal 4735..4736
         /evidence=not_experimental
   mRNA     join(4777..4888,5311..5481,6139..6360,6526..6618,
         6822..6941,7129..7218,7364..7480,8011..8206,9076..9872)
         /product="epithelium-restricted Ets protein ESX"
   5' UTR join(4777..4888,5311..5318)
```

-continued

```
exon    4777..4888
    /number=1
misc_feature 4785..4901
    /note="putative CpG island"
exon    5311..5481
    /number=2
CDS     join(5319..5481,6139..6360,6526..6618,6822..6941,
    7129..7218,7364..7480,8011..8206,9076..9190)
    /note="epithelial-restricted with serine box; Homo
    sapiens ESX cDNA ORF presented in GenBank Accession
    Number U66894"
    /codon_start=1
    /product="epithelium-restricted Ets protein ESX"
    /protein_id="AAD45237.1"
    /db_xref="GI:5565859"
    /translation (SEQ ID NO: 3) =
"MAATCEISNIFSNYFSAMYSSEDSTLASVPPAATFGADDLVLTLSNPQMSLEGTEKAS
WLGEQPQFWSKTQVLDWISYQVEKNKYDASAIDFSRCDMDGATLCNCALEELRLVFG
PLGDQLHAQLRDLTSSSSDELSWIIELLEKDGMAFQEALDPGPFDQGSPFAQELLDDGQ
QASPYHPGSCGAGAPSPGSSDVSTAGTGASRSSHSSDSGGSDVDLDPTDGKLFPSDGFR
DCKKGDPKHGKRKRGRPRKLSKEYWDCLEGKKSKHAPRGTHLWEFIRDILIHPELNEG
LMKWENRHEGVFKFLRSEAVAQLWGQKKKNSNMTYEKLSRAMRYYYKREILERVD
GRRLVYKFGKNSSGWKEEEVLQSRN"
repeat_region 5773..6059
    /rpt_family="Alu"
    /rpt_type=dispersed
exon    6139..6360
    /number=3
exon    6526..6618
    /number=4
exon    6822..6941
    /number=5
exon    7129..7218
    /number=6
exon    7364..7480
    /number=7
misc_feature 7401..7525
    /note="putative CpG island"
exon    8011..8206
    /number=8
```

-continued

```
   repeat_region 8655..8775
       /rpt_family="Alu"
       /rpt_type=dispersed
   exon    9076..9872
       /number=9
   3'UTR  9191..9872
   polyA_signal 9845..9850
       /evidence=not_experimental
   misc_feature complement(9952..10387)
       /note="similar to THC 209689"
   misc_feature 10358..10772
       /note="similar to THC 203540"
BASE COUNT 2486 a 2843 c 2985 g 2458 t
ORIGIN
     1 aagcttctta ggcatgtgta tgtgtgtttc ttgcagggga agcagaagta tacacttccg
    61 ctgtaccacg caatgatggg tggcagtgag gtggcccaga ccctcgccaa ggagactttt
   121 gcatccaccg cctcccagct ccacagcaat gttgtcaact atgtccagca gatcgtggca
   181 cccaagggca gttagaggct cgtgtgcatg gcccctgcct cttcaggctc tccaggcttt
   241 cagaataatt gtttgttccc aaattcctgt tccctgatca acttcctgga gtttatatcc
   301 cctcaggata atctattctc tagcttaggt atctgtgact cttgggcctc tgctctggtg
   361 ggaacttact tctctatagc ccactgagcc ccgagacaga gaacctgccc acagctctcc
   421 ccgctacagg ctgcaggcac tgcagggcag cgggtattct cctccccacc taagtctctg
   481 ggaagaagtg gagaggactg atgctcttct tttttctctt tctgtccttt ttcttgctga
   541 ttttatgcaa agggctggca ttctgattgt tcttttttca ggtttaatcc ttatttaat
   601 aaagttttca agcaaaaatt aagttacgga ttgagtgact attaaatttc ttccaccaga
   661 ggtcctcact gtgtttgttc aggaaaggtc actggggag gcccagagaa tgacagtatt
   721 ttcctgtcct cagggaacag ccagggtgaa ggaggtgggt gtcctacaca tgcatatgaa
   781 aaaaaatatg gcaaaatggc acagctggtg caggaaaatg aaaaaggaat agcattccag
   841 ttctccgtga agcagctgaa ttctctatct gcagcagcat tcccattatc ttttccatca
   901 ctaagaaaaa aaatgggct gggcacggtg gctcatgcct gtaatcccag cactttggga
   961 ggctgaggcg agaggatcgc ttgagcccag gagtttgaga ccaccctggc caacatagca
  1021 ggacttcatc tctaccaaaa aaaaaaaaaa aaaaaaaaa aagccaggcg tggtggctca
  1081 cgcctgtaat ctcaacactt tgggaggctg aggcaggcaa atcacttgag gtcagaagtt
  1141 tgagaccagc atggccaaca tggtgaaacc ccatctctac tgaaaaaaaa gatagatgca
  1201 aaaattagcc aggcatggtg gctcacacct gtagttccag ttacttggga ggctgaagca
  1261 ggagaaacac ttgaacctgg gaggtggagg ttgcagtaaa ctgagatcat gccactgcac
  1321 tccagcctgg gtgacagagt aagacttctc aaaaaaaaaa aaaaaaagct gggcgtggtg
  1381 gtgcattcct gtggtttcag ctactcagga ggctgaggca ggaggatcac ttgagcccaa
  1441 gaggtcaagg ccacagtgag tcttgattgt gccactgaac tccagcctga gtgacagagt
  1501 gagaccctgt ctcaaaaata aaataaagt gtcttatgac ttttatcta cccttctgcc
```

-continued

```
1561 catgcccaag gcttcactgg gcctcacctg tctttgatcc tagataacta tttgaatggt 1621 aatcaagtaa agtctttaga acttagcact aaattctgat ttcctggcct caacatgggg 1681 acctaaacag ttagcaatct gggtttggga gtgggatgag ggagggttg gaagaaatat 1741 ttagtgtgtt tcatttgcct ttcttaaata cagggcaccc ctgaaacagg ctttgttcgc 1801 agctctgctc tgtcctcgga tttaggttat cgaacaggct tcctccctcc cctgcacaag 1861 ggttgggaat gagtcgattt gctttcactc agcaagagca agggactagt ggtgaccaag 1921 tggtagactg gagaggcctc tgcccgtgg cacacagctc caccatcaga gagggtgatg 1981 tgggtcatag gtgagggatc tggaggcccg gtatcggaag agcttctcca ggcactggca 2041 ttttgacagc aaactgcttc cgtggctctt tcaggactgt tcctgggcaa tatgttattg 2101 gcaaggacta ttttagggct atccagttgt ctcccctct ccccaacctt ttatctagct 2161 tatcagtagc tatctttcct tgctctgtac aaaaacctat agcaccaata ggcccagtaa 2221 tcatgaaggg tcagtgcaag gaaaggctgg aagcccttcc tctaacagcc gtgctgtgac 2281 tccactaact ttgtggggtc tcccattaca tagcgtgggt atcctgagct gtgcagcctg 2341 cctcactcac caccttggta cctgacagga ctactggatg tgcctgtcct tttgtaggac 2401 attctcccat cccaaagatg aggctgtgct gccgtgtggg caagctctgt gggagaggg 2461 gaggccagtg ggttgttttt gccatcacag aatactggga agccctggc atcctgctcc 2521 atagctctct tcaccactat cctggaacct tctcccacc cccatcccca tgcctccaag 2581 gcactgacct caaatccaag tctttctcac ttatctcaag ctgccagcct gtagggattc 2641 cttatctcag ctccatgtca gcggtgagga agccccaaga aggcaaggga gctgacagcc 2701 ttctcatttt tctcgtacat cctcctgttc accccgccat cccgggagcc ccagccagat 2761 gctcttcagg gcagggagca cgtgagcagc cctggggcta gaagccggtt ctcccacatt 2821 cctgggtgag ggactgggtg gagggtgtgc ctgcctcagg ctccttgggg gaggccccct 2881 gaagggctgg ggaaaatcct actgagcccc aggctctcct gcctgcactg gcccagtgcg 2941 ggggcggggg ggcgggggga tcctacattt caaatgcata aaaatctaga tatgggctgg 3001 gcgcagtagc tcatgcctgt aatcccagca ctttgggagg ctgaggcagg cagatcatga 3061 ggtcaggaga tcgagtccat cctggctaac atggtgaaac cccgtctcta ctaaaaatac 3121 agaaagccgg gcatggcagc gggcgcctgt aatcccagct actcggaaag ctgaggcagg 3181 agaatcgctt gaacccacga gtcagaggtt gcagtgagca gatatcacgc cactgcactc 3241 caacctgggc gacagagcga gactccacct caaaacaaaa taaaccaaat actagatctg 3301 gaagagatct tagggattat taaattcaga caacctcatt ttttatagat ggggaaacaa 3361 gcacagactc caagggtctc atccaagatc acacagttgc agatgctggc tacaagtctc 3421 ctgcctcaac cacctgtatt accccattca gggtctcaag aagggtctat aagacactat 3481 ccattgtgtt tcgggctgag tccatagaga caaccacaga catgggggac tctgcccaca 3541 gggaaggcaa gggctctggc catggagctg gatgggaaga ctctgaagcc cgaagacatt 3601 gaatcctgtg cagggaaaga gcgagggttt tgtgtacaac acacctgcat acctggatgt 3661 gaatctcagc tccaccccctt caccaactct gtgtggcctg gcaagccat tctaagggaa 3721 ccctccacac tgcaactttc atgtctataa aatgggaata accatgcatt ccttacagga 3781 cttttttggt gtgaggatta aatgagagaa tatgttgaaa agtgcttggt aaatatatta 3841 atactatgca ttccctcttc tttgaatgac gtgacccagg tagtcaggct tctgaccact 3901 agagggcagc agaaggtact ggaaaactgg gccgagtgaa ccagagatta gatgggtcc
```

```
3961  agagagcagg gatgaactta cccgtgtgga ttctggcaac tccggcaggg agggctccag 4021  caggcgctga gggaagaact tcaagcaga gccgggtctc ttcaggagcg actgcagcaa 4081  ccctgatgct tggatggagt ccaggcaggt gatggtagtg aagaccttgc aacagagtg 4141  ggcgctggag aaggagccct ttagtgggga ccctggggcc acgactaggc tggcaggccc 4201  agccagcacc aattaatcca tgagtattgc ccagcattga gcctggagca ccttccagcc 4261  cctggccaga gtcctgggtg ttctgggaaa acccctaaa cctagtaact cctctcccta 4321  ctaggcctct tgttgctga atctctggaa tttaggggcc agcagctttc tgactcaggt 4381  cagccagggg ttcatgttcc ctcacttgcc ctcccccctgc ctggcccatc tctggcctgg 4441  cccctgggag gaatttcctg ggcagagggg cagccgaaag cacagatgcc caccccagca 4501  acgttcccgc cacctgccca ggcagtgcc ccgtgcccaa cccagagggg tgcgggatga 4561  cagactctga caatcattaa accagccggg cctgatttcc cagcactgcc tgctaagatc 4621  cgggccaagt ggcactgaat atgcaaatca cctggggcca ggagcccagt ctaaaggcca 4681  ggaaatcccc tccatccaat gagacaccag ctcaggttac tgcaggggac acactataaa 4741  gccctgagct caggaggag ctccctccag gctcta START mRNA> ttta gagccgggta
      ggggagcgca 4801  gcggccagat acctcagcgc tacctggcgg aactggattt ctctcccgcc tgccggcctg 4861  cctgccacag ccggactccg ccactccg INTRON1> gt aggattcccc gcctgtcatt ccctagccca 4921  gctcttggga aactgcagag gggtccagag gatttgcagt tctgaacctg cacactccag 4981  tctaggatct ccgagcaaga gcgtaggtgt cctgagggtc aaagaacaga gagagattgt 5041  ctctgggaag gcagaatggc catgacgccg ctagtctggc tccagggccc cagagatctg 5101  aggagggaag cccagctgga ggctcctgtg gtcctgccct ggtctgagat cttggagccc 5161  ttcttgaaga gacggtgtcc gcagagttgc tgatcttcct gcccctgggg gctactcttg 5221  cccagggttg gcaaagcag agtagctggg agtgtaagga gaggaccctc gtcccctcac 5281  caacctcatc ctctctcccc ctacccacag EXON2> gtagcctc START CDS> at ggctgcaacc
      tgtgagatta 5341  gcaacatttt tagcaactac ttcagtgcga tgtacagctc ggaggactcc accctggcct 5401  ctgttccccc tgctgccacc tttggggccg atgacttggt actgaccctg agcaaccccc 5461  agatgtcatt ggagggtaca INTRON2> ggtgggtctc agcggggtgg gatgggcac ggagtgggag 5521  acagatccat ctaagggcct gttagacaaa tgggggaata ggcagggagg agggtctcta 5581  ggcaaattcc agggctagag gctgagactt agtgactgag gtgctgggg ttgtgggggct 5641  gtgacaggca gagggaggtg tcagatacca ggacaagggt gttgtgaatg ctacctcctg 5701  cccctactct tgggatggct ccaagggctg aggtgtgaat cccagtgtg ctccaggaat 5761  ggggctgtgt gggctgggag tggtggctca cgcctgtaat cccagcactt gggaggctg 5821  agctgagcgg atcacctgag gtcaagagtt cgagaccagc ctagccaaca tggtgaaacc 5881  ccgtctctac taaaaataca aaaaaaatt tatcccagcg tggtggtggg cacctataat 5941  cccagctact ggggaggctg acgcaggagt atcgcttgaa cctgggaggt ggaggttgct 6001  gtgagccgag attgtgccat tgcaccccag cctaggtgac aggagtgaga ctccatctca 6061  aaaaaaaaaa aaaaaatggg gctgtaaggt ctgctgggtg gcctgagctg agcctgtttc 6121  cctgcctggc ccttgcag EXON3> ag aaggccagct ggttggggga acagccccag ttctggtcga 6181  agacgcaggt tctggactgg atcagctacc aagtggggaa gaacaagtac gacgcaagcg 6241  ccattgactt ctcacgatgt gacatggatg gcgccaccct ctgcaattgt gcccttgagg
```

```
6301 agctgcgtct ggtctttggg cctctggggg accaactcca tgcccagctg cgagacctca

6361 INTRON3> gtgagtccag gccctgag gctggggagc agctccacat gttgagctga gtcgagttca 6421 gtgtggccgt aggcaggccc tggagctctg gccagctgc acagccagag agagcccttg 6481 agggagggat taggggagtg tgacccttcc ttccttcctt gtcag EXON4> cttcc agctcttctg 6541 atgagctcag ttggatcatt gagctgctgg agaaggatgg catggccttc caggaggccc 6601 tagacccagg gcccttttg INTRON4> gt gagaaccgt tttctccttc cttccccagc ctgtcttgtc 6661 ccatccctgc ccctccacag agtgctagag atgaccccct ccccagactt cttcctccct 6721 caattagaaa aattgcagca ggtcatcaga cccatgggca gcatcacctg tcctggtctg 6781 gtcccctgag ccctctctga gttctcacct cctcttccca g EXON5> accagggca gccccctttgc 6841 ccaggagctg ctggacgacg tcagcaagc cagcccctac caccccggca gctgtggcgc 6901 aggagccccc tccctggca gctctgacgt ctccaccgca g INTRON5> gtgagagct ctctctgggc 6961 cacaacctcc cttccccgaa gtgtcccttg ttccctctgg ctcccagcac cataactcag 7021 gccttctggc aggaacagga acaggctggg aagtgtgtcc tgagagccag cagcgtggtt 7081 gaacagaagg tgggccggca ggggacttac tctgaccccg ccccccag EXON6> gg actggtgctt 7141 ctcggagctc ccactcctca gactccggtg gaagtgacgt ggacctggat cccactgatg 7201 gcaagctctt ccccagcg INTRON6> gt gagtcgaggg aggtccccaa gagggcgtcc catttagcaa 7261 tgcacagggg gcccggctct tcctgcagcc ttttcctgta gagggctac tctcctaac 7321 tcccctcttg ccccLccttg accttccacc accgtcccca cag EXON7> atggttt tcgtgactgc 7381 aagaagggggg atcccaagca cggaagcgg aaacgaggcc ggccccgaaa gctgagcaaa 7441 gagtactggg actgtctcga gggcaagaag agcaagcacg INTRON7> gtgagctccg ggggcacgtg 7501 ggtcctccct gcgccgggct gagcggcttc ctggggcact gcgggttgtt gcaggtatcc 7561 cttctcccgt tttctctggc ctccgcatgg cctttggtaa ggctgtgcac aagctggggg 7621 ctctatggta tcggtcacca cctaattgca gagcctggct tggtggtcct ggagaggagg 7681 aggaaataag gctcccagtg ggaggctcat ggtaccagag tcctgtccac tgactccagt 7741 gtcctgtcca ctgactccag ttctctctgc acttggccac tgtcctgccc tctgggacac 7801 cctcaatgtg aggaggcagc tggtgggtct taggtgggct gaggagaaaa gcagtcactg 7861 cagtacccgc acagagggca ctgcggggtc tctggagagg cttgctgcat gctgtggcca 7921 agtcagcagt gcactggggc gggcagggct ggctggcctt gggtgagagg ggacacctgg 7981 atggcaaact gatggaggct ggccttgcag EXON8> cgcccagagg cacccacctg tgggagttca 8041 tccgggacat cctcatccac ccggagctca acgagggcct catgaagtgg gagaatcggc 8101 atgaaggcgt cttcaagttc ctgcgctccg aggctgtggc caactatggg gccaaaaga 8161 aaaagaacag caacatgacc tacgagaagc tgagccgggc catgag INTRON8> gtga gctggcggcc 8221 aggaccctca cgatacagcc ggacatgggg acaggcgctc acactcccac cgccctcttt 8281 ctggctgcca cttggttttct tgcaacaggg ctgagtcctt agagtgagga caacatctgg 8341 gttggtctac ttcatggatt aaatgacaac atggagaaag tattagcctg gcagacagca 8401 gacacagtgc acttgagcta gcagcaacat ttcttgtatc gcctgtgagg cttgtcctca 8461 ggaaggcacc tggagagtgg gaaaggggc aggagccgtg cccacccagg gctggcttt 8521 ctcctcgttg aagcacttag gttgttttc tctgggcctc agtttcctcc tgtgtccagg 8581 agtacactag atcatcttaa gatcccgtcc agccctaaaa tcatgtactt acttttttt 8641 tctttttcttt ttttaaatag aggcaagggt ctctacgttg gccaggccgg tctcaaactc
```

```
-continued
 8701 ctggcctcaa atgactctcc tgcctcggcc tctcaaagtg ctgggattac aggtgtgagc
 8761 caccgtgccc agctccctgg ccttaaaagt catgtaattt aatgatcaga ccccagtcac
 8821 agccatagga tacaaagaag caaaggcaaa gagccctgtg tcctgggcac ggttacaggc
 8881 cagtgtaggg aaagagcttc tgcttgccag tgtgaagaac agaggagttt aggaagtgtg
 8941 agtcaggctc agcttagtca ggcagagacc agtgggcatg ggttacctgg gggtaacgcg
 9001 ggccaggtgg gcgggctggc agcctggggc ccatttcctg ccaaagcacc tctgaccatc
 9061 cttctcttca cccag EXON9> gtact actacaaacg ggagatcctg aacgggtgg atggccggcg
 9121 actcgtctac aagtttggca aaaactcaag cggctggaag gaggaagagg ttctccagag
 9181 tcggaactga END CDS gggttggaac tatacccggg accaaactca cggaccactc gaggcctgca
 9241 aaccttcctg ggaggacagg caggccagat ggcccctcca ctggggaatg ctcccagctg
 9301 tgctgtggag agaagctgat gttttggtgt attgtcagcc atcgtcctgg gactcggaga
 9361 ctatggcctc gcctccccac cctcctcttg gaattacaag ccctgggggtt tgaagctgac
 9421 tttatagctg caagtgtatc tccttttatc tggtgcctcc tcaaacccag tctcagacac
 9481 taaatgcaga caacaccttc ctcctgcaga cacctggact gagccaagga ggcctgggga
 9541 ggccctaggg gagcaccgtg atggagagga cagagcaggg gctccagcac cttctttctg
 9601 gactggcgtt caccctccctg ctcagtgctt gggctccacg ggcaggggtc agagcactcc
 9661 ctaatttatg tgctatataa atatgtcaga tgtacataga gatctattt ttctaaaaca
 9721 ttcccctccc cactcctctc ccacagagtg ctggactgtt ccaggccctc cagtgggctg
 9781 atgctgggac ccttaggatg gggctcccag ctcctttctc ctgtgaatgg aggcagagac
 9841 ctccaataaa gtgccttctg ggcttttttct a END mRNA acctttgtc ttagctacct gtgtactgaa
 9901 atttgggcct ttggatcgaa tatggtcaag aggttggagg ggaggaaaat gaaggtctac
 9961 caggctgagg gtgagggcaa aggctgacga agagggggagt tacagatttc ctgtagcagg
10021 tgtgggctta cagacacatg gactgggctg ggaggcgagc aaaggaagca gctgagactg
10081 ttggagaacg cttacaagac ttcatgcaag caaggacatg aactcagaac actgaggtca
10141 gaagcatcct gctgtcatga caccgctcga gtgaccttga ccttgaccaa gtctgtcctg
10201 tttaggactg attttttccta ttaggctagg gtttggacct gatgttctca agatgtctag
10261 aattgcatgg ctggccttgt ggaatagatg gttttgcatt ccagccaagt gtgctgtaaa
10321 ctgtatatct gtaatatgaa tcccagcttt tgagtctgac aaaatcagag ttaggatctt
10381 gtaaaggaaa aaaaaaaaaa caaacaaaa tggagatgag tacttgctga gaaagaatga
10441 gggaaggagt tggcatttgt tgaaagtata gtcttttctc cttttttttt taattgcaac
10501 ttttactta gatttaggag gtcgtgcgca ggtttgttac atgggtatat tgtgtgatgc
10561 tgagcttggg atgcgaatga tcctgtcacc caggtagtga gtatagcacc cagtgaaact
10621 gtagtctcat gccaggcact gtgctagccc actctggctc atttaatcct ctcctaagaa
10681 gagaggagac acagcgtccc catttgacag atgcagaaag aggttccaca ggtgtgcctt
10741 gattctgtcc taaaaccgtt tcccggaagc tt
//
```

SEQ ID NO:2—ELF3 cDNA and
SEQ ID NO:4—ELF3 amino acid sequence alternative 2

1959 bp full length of spliced mRNA of ELF3 gene in breast tumor cell lines and predicted amino acid sequence of ELF3 gene. The adenosine at the atg start codon is considered the number one nucleotide.

```
-135
ctccgccactccggtaggattccccgcctgtcattccctagcccagctcttgggaaac tgcagaggggtccagaggatttgcagttctgaacctgcacactccagtctaggatctc cgagcaagagcgtagcctc 1 atggctacaacctgtgagattagcaacatttttagcaactacttc
    M  A  T  T  C  E  I  S  N  I  F  S  N  Y  F 46 agtgcgatgtacagctcggaggactccaccctggcctctgttccc
    S  A  M  Y  S  S  E  D  S  T  L  A  S  V  P 91 cctgctgccacctttggggccgatgacttggtactgaccctgagc
    P  A  A  T  F  G  A  D  D  L  V  L  T  L  S 136 aaccccagatgtcattggagggtacagagaaggccagctggttg
    N  P  Q  M  S  L  E  G  T  E  K  A  S  W  L 181 ggggaacagccccagttctggttgaagacgcaggttctggactgg
    G  E  Q  P  Q  F  W  L  K  T  Q  V  L  D  W 226 atcagctaccaagtggagaagaacaagtacgacgcaagcgccatt
    I  S  Y  Q  V  E  K  N  K  Y  D  A  S  A  I 271 gacttctcacgatgtgacatggatggcgccaccctctgcaattgt
    D  F  S  R  C  D  M  D  G  A  T  L  C  N  C 316 gcccttgaggagctgcgtctggtctttgggcctctgggggaccaa
    A  L  E  E  L  R  L  V  F  G  P  L  G  D  Q 361 ctccatgcccagttgcgagacctcacttccagctcttcttatgag
    L  H  A  Q  L  R  D  L  T  S  S  S  S  Y  E 406 ctcagttggatcattgagctgctggagaaggatggcatggccttc
    L  S  W  I  I  E  L  L  E  K  D  G  M  A  F 451 caggaggccctagacccagggccctttgaccagggcagccccttt
    Q  E  A  L  D  P  G  P  F  D  Q  G  S  P  F 496 gcccaggagctgctggacgacggtcagcaagccagcccctaccac
    A  Q  E  L  L  D  D  G  Q  Q  A  S  P  Y  H 541 cccggcagttgtggcgcaggagccccctcccccggcagctctgac
    P  G  S  C  G  A  G  A  P  S  P  G  S  S  D 586 gtctccaccgcagggactggtgcttctcggagctcccactcctca
    V  S  T  A  G  T  G  A  S  R  S  S  H  S  S 631 gactccggtggaagtgacgtggacctggatcccactgatggcaag
    D  S  G  G  S  D  V  D  L  D  P  T  D  G  K 676 ctcttccccagcgatggttttcgtgactgcaagaaggggatccc
    L  F  P  S  D  G  F  R  D  C  K  K  G  D  P 721 aagcacgggaagcggaaacgaggccggccccgaaagctgagcaaa
    K  H  G  K  R  K  R  G  R  P  R  K  L  S  K 766 gagtgctgggactgtctcgagggcaagaagagcaagcacgcgccc
    E  C  W  D  C  L  E  G  K  K  S  K  H  A  P 811 agaggcacccacctgtgggagttcatccgggacatcctcatccac
    R  G  T  M  L  W  E  F  I  R  D  I  L  I  H 856 ccggagctcaacgagggcctcatgaagtgggagaatcgacatgaa
    P  E  L  N  E  G  L  M  K  W  E  N  R  H  E 901 ggcgtcttcaagttcctgcgctccgaggctgtggcccaactatgg
    G  V  F  K  F  L  R  S  E  A  V  A  Q  L  W 946 ggccaaaagaaaaagaacagcaacatgacctacgagaagctgagc
    G  Q  K  K  K  N  S  N  M  T  Y  E  K  L  S 991 cgggccatgaggtactactacaaacgggagatcctggaacgggtg
    R  A  M  R  Y  Y  Y  K  R  E  I  L  E  R  V 1036 gatggccggcgactcgtctacaagtttggcaaaaactcaagcggc
     D  G  R  R  L  V  Y  K  F  G  K  N  S  S  G 1081 tggaaggaggaagaggttctccagagtcggaactga 1116
```

```
 W  K  E  E  E  V  L  Q  S  R  N  *
gggttggaactatacccgggaccaaactcacggaccactcgaggcctgc aaaccttcctgggaggacaggcaggccagatggcccctccactggggaat gctcccagctgtgctgtggagagaagctgatgttttggtgtattgtcagc catcgtcctgggactcggagactatggcctcgccttccaccccttctctt ggaattacaaagccctgggtttgaactgactttatagcttgcaagtgta tctccttttatctggtgcctcctcaaacccagtcttcaaacactaaatgc agacaacaccttcttctgcaaacaccctggacttgacccaaggaggccct ggggaggccctaggggagcaccgtgatgagaggacagagcaggggctcca gcaccttcttctggactggcgttcacctccctgctcagtgcttgggctc cacgggcaggggtcagagcactccctaatttatgtgctatataaatatgt cagatgtacatagagatctatttttttctaaaacattcccctcccactcc tctcccacagagtgctggactgttccaggccctccagtgggctgatgctg ggacccttaggatggggctcccagctcctttctcctgtgaatggaggcag agacctccaataaagtgccttctgggcttttccaaaaaaaaaaaaaaaa aaaaaaaa SEQ ID NO: 5 - ELF3 intron 4
gtgagaacccgttttctccttccttccccagcctgtcttgtcccatccctgcccctccacagagtgctagagatgacccctccccagacttc ttcctccctcaattagaaaaattgcagcaggtcatcagacccatgggcagcatcacctgtcctggtctggtcccctgagccctctctgagtt ctcacctcctcttcccag SEQ ID NO: 6 - ELF3 intron 5
gtgagagctctctctgggccacaaccctcccttccccgaagtgtcccttgttccctctggctcccagcaccataactcaggccttctggc aggaacaggaacaggctgggaagtgtgtcctgagagccagcagcgtggttgaacagaaggtgggccggcaggggacttactctgacc ccgcccccag SEQ ID NO: 7 - ELF3 intron 6
gtgagtcgagggaggtcccccaagagggcgtcccatttagcaatgcacaggggccggctcttcctgcagccttttcctgtagaggggc tactctccctaactcccctcttgcccctccttgaccttccaccaccgtccccacag SEQ ID NO: 8 - ELF3 intron 7
gtgagctccggggcacgtgggtcctccctgcgccgggctgagcggcttcctggggcactgcgggttgttgcaggtatcccttctcccgt tttctctggcctccgcatggcctttggtaaggctgtgcacaagctgggggctctatggtatcggtcaccacctaattgcagagcctggcttg gtggtcctggagaggaggaggaaataaggctcccagtggggaggctcatggtaccagagtcctgtccactgactccagtgtcctgtccac tgactccagttctctctgcacttggccactgtcctgccctctgggacaccctcaatgtgaggaggcagctggtgggtcttaggtgggctga ggagaaaagcagtcactgcagtacccgcacagagggcactgcggggtctctggagaggcttgctgcatgctgtggccaagtcagcagt gcactgggcgggcagggctggctggccttgggtgagaggggacacctggatggcaaactgatggaggctggccttgcag SEQ ID NO: 9 - ELF3 intron 8
gtgagctggcggccaggaccctcacgatacagccggacatggggacaggcgctcacactcccaccgccctctttctggctgccacttg gtttcttgcaacagggctgagtccttagagtgaggacaacatctgggttggtctacttcatggattaaatgacaacatggagaaagtattag cctggcagacagcagacacagtgcacttgagctagcagcaacatttcttgtatcgcctgtgaggcttgtcctcaggaaggcacctggaga gtgggaaggggcaggagccgtgcccacccagggcctggctttctcctcgttgaagcacttaggttgttttctctgggcctcagtttcct cctgtgtccaggagtacactagatcatcttaagatcccgtccagccctaaaatcatgtacttacttttttttttcttttttctttttttaaatagaggcaa gggtctctacgttggccaggccggtctcaaactcctggcctcaaatgactctcctgcctcggcctctcaaagtgctgggattacaggtgtg agccaccgtgcccagctccctggccttaaaagtcatgtaatttaatgatcagacccagtcacagccataggatacaaagaagcaaagg caaagagccctgtgtcctgggcacggttacaggccagtgtagggaaagagcttctgcttgccagtgtgaagaacagaggagtttaggaa
```

```
gtgtgagtcaggct cagcttagtcaggcagagaccagtgggcatgggttacctgggggtaacgcgggccaggtgggcgggctggcag cctggggcccatttcctgccaaagcacctctgaccatccttctcttcacccag
```

SEQ ID NO: 10- ELF3 primary transcript - numbering as in SEQ ID NO: 1.
ttta gagccgggta ggggagcgca

```
4801 gcggccagat acctcagcgc tacctggcgg aactggatttt ctctcccgcc tgccggcctg 4861 cctgccacag ccggactccg ccactccg INTRON1> gt aggattcccc gcctgtcatt ccctagccca 4921 gctcttggga aactgcagag gggtccagag gatttgcagt tctgaacctg cacactccag 4981 tctaggatct ccgagcaaga gcgtaggtgt cctgagggtc aaagaacaga gagagattgt 5041 ctctgggaag gcagaatggc catgacgccg ctagtctggc tccagggccc cagagatctg 5101 aggagggaag cccagctgga ggctcctgtg gtcctgccct ggtctgagat cttggagccc 5161 ttcttgaaga gacggtgtcc gcagagttgc tgatcttcct gccctgggg gctactcttg 5221 cccaggggttg ggcaaagcag agtagctggg agtgtaagga gaggaccctc gtcccctcac 5281 caacctcatc ctctctcccc ctacccacag EXON2> gtagcctc START CDS> at ggctgcaacc
     tgtgagatta 5341 gcaacatttt tagcaactac ttcagtgcga tgtacagctc ggaggactcc accctggcct 5401 ctgttccccc tgctgccacc tttggggccg atgacttggt actgaccctg agcaaccccc 5461 agatgtcatt ggagggtaca INTRON2> ggtgggtctc agcggggtgg gatggggcac ggagtgggag 5521 acagatccat ctaagggcct gttagacaaa tgggggaata ggcagggagg agggtctcta 5581 ggcaaattcc agggctagag gctgagactt agtgactgag gtgctggggg ttgtggggct 5641 gtgacaggca gagggaggtg tcagatacca ggacaagggt gttgtgaatg ctacctcctg 5701 ccctactct tgggatggct ccaagggctg aggtgtgaat ccccagtgtg ctccaggaat 5761 ggggctgtgt gggctgggag tggtggctca cgcctgtaat cccagcactt tgggaggctg 5821 agctgagcgg atcacctgag gtcaagagtt cgagaccagc ctagccaaca tggtgaaacc 5881 ccgtctctac taaaaataca aaaaaaaatt tatcccagcg tggtggtggg cacctataat 5941 cccagctact ggggaggctg acgcaggagt atcgcttgaa cctgggaggg ggaggttgct 6001 gtgagccgag attgtgccat tgcaccccag cctaggtgac aggagtgaga ctccatctca 6061 aaaaaaaaaa aaaaaatggg gctgtaaggt ctgctgggtg gcctgagctg agcctgtttc 6121 cctgcctggc ccttgcag EXON3> ag aaggccagct ggttggggga acagccccag ttctggtcga 6181 agacgcaggt tctggactgg atcagctacc aagtggagaa gaacaagtac gacgcaagcg 6241 ccattgactt ctcacgatgt gacatggatg gcgccaccct ctgcaattgt gcccttgagg 6301 agctgcgtct ggtctttggg cctctggggg accaactcca tgcccagctg cgagacctca 6361 INTRON3> gtgagtccag gccctggag gctggggagc agctccacat gttgagctga gtcgagttca 6421 gtgtggccgt aggcaggccc tggagctctg ggccagctgc acagccagag agagcccttg 6481 agggagggat taggggagtg tgaccccttcc ttccttcctt gtcag EXON4> cttcc agctcttctg 6541 atgagctcag ttggatcatt gagctgctgg agaaggatgg catggccttc caggaggccc 6601 tagacccagg gccctttg INTRON4> gt gagaacccgt ttctccttc cttccccagc ctgtcttgtc 6661 ccatccctgc ccctccacag agtgctagag atgaccccct ccccagactt cttcctccct 6721 caattagaaa aattgcagca ggtcatcaga cccatgggca gcatcacctg tctggtctg 6781 gtcccctgag ccctctctga gttctcacct cctcttccca g EXON5> accagggca gccccttttgc 6841 ccaggagctg ctggacgacg gtcagcaagc cagccccctac cacccggca gctgtggcgc 6901 aggagccccc tcccctggca gctctgacgt ctccaccgca g INTRON5> gtgagagct ctctctgggc
```

-continued

```
6961 cacaacctcc cttccccgaa gtgtcccttg ttccctctgg ctcccagcac cataactcag 7021 gccttctggc aggaacagga acaggctggg aagtgtgtcc tgagagccag cagcgtggtt 7081 gaacagaagg tgggccggca ggggacttac tctgaccccg ccccccag EXON6> gg actggtgctt 7141 ctcggagctc ccactcctca gactccggtg gaagtgacgt ggacctggat cccactgatg 7201 gcaagctctt ccccagcg INTRON6> gt gagtcgaggg aggtccccaa gagggcgtcc catttagcaa 7261 tgcacagggg gcccggctct tcctgcagcc ttttcctgta gagggctac tctccctaac 7321 tccctcttg ccctccttg accttccacc accgtcccca cag EXON7> atggttt tcgtgactgc 7381 aagaagggg atcccaagca cgggaagcgg aaacgaggcc ggccccgaaa gctgagcaaa 7441 gagtactggg actgtctcga gggcaagaag agcaagcacg INTRON7> gtgagctccg ggggcacgtg 7501 ggtcctccct cgccgggct gagcggcttc ctggggcact gcgggttgtt gcaggtatcc 7561 cttctcccgt tttctctggc ctccgcatgg cctttggtaa ggctgtgcac aagctggggg 7621 ctctatggta tcggtcacca cctaattgca gagcctggct tggtggtcct ggagaggagg 7681 aggaaataag gctcccagtg ggaggctcat ggtaccagag tcctgtccac tgactccagt 7741 gtcctgtcca ctgactccag ttctctctgc acttggccac tgtcctgccc tctgggacac 7801 cctcaatgtg aggaggcagc tggtgggtct taggtgggct gaggagaaaa gcagtcactg 7861 cagtacccgc acagagggca ctgcggggtc tctggagagg cttgctgcat gctgtggcca 7921 agtcagcagt gcactggggc gggcagggct ggctggcctt gggtgagagg ggacacctgg 7981 atggcaaact gatggaggct ggccttgcag EXON8> cgcccagagg cacccacctg tgggagttca 8041 tccgggacat cctcatccac ccggagctca acgagggcct catgaagtgg gagaatcggc 8101 atgaaggcgt cttcaagttc ctgcgctccg aggctgtggc ccaactatgg gccaaaaga 8161 aaaagaacag caacatgacc tacgagaagc tgagccgggc catgag INTRON8> gtga gctggcggcc 8221 aggaccctca cgatacagcc ggacatgggg acaggcgctc acactcccac cgcccctcttt 8281 ctggctgcca cttggtttct tgcaacaggg ctgagtcctt agagtgagga caacatctgg 8341 gttggtctac ttcatggatt aaatgacaac atggagaaag tattagcctg gcagacagca 8401 gacacagtgc acttgagcta gcagcaacat ttcttgtatc gcctgtgagg cttgtcctca 8461 ggaaggcacc tggagagtgg gaaggggc aggagccgtg cccacccagg gcctggcttt 8521 ctcctcgttg aagcacttag gttgtttttc tctgggcctc agtttcctcc tgtgtccagg 8581 agtacactag atcatcttaa gatcccgtcc agccctaaaa tcatgtactt actttttttt 8641 tcttttctt ttttaaatag aggcaagggt ctctacgttg gccaggccgg tctcaaactc 8701 ctggcctcaa atgactctcc tgcctcggcc tctcaaagtg ctgggattac aggtgtgagc 8761 caccgtgccc agctccctgg ccttaaaagt catgtaattt aatgatcaga ccccagtcac 8821 agccatagga tacaaagaag caaaggcaaa gagccctgtg tcctgggcac ggttacaggc 8881 cagtgtaggg aaagagcttc tgcttgccag tgtgaagaac agaggagttt aggaagtgtg 8941 agtcaggctc agcttagtca ggcagagacc agtgggcatg ggttacctgg gggtaacgcg 9001 ggccaggtgg gcgggctggc agcctggggc ccatttcctg ccaaagcacc tctgaccatc 9061 cttctcttca cccag EXON9> gtact actacaaacg ggagatcctg gaacgggtgg atggccggcg 9121 actcgtctac aagtttgca aaaactcaag cggctggaag gaggaagagg ttctccagag 9181 tcggaactga END CDS ggggttggaac tataccckggg accaaactca cggaccactc gaggcctgca 9241 aaccttcctg ggaggacagg caggccagat ggcccctcca ctggggaatg ctcccagctg 9301 tgctgtggag agaagctgat gttttggtgt attgtcagcc atcgtcctgg gactcggaga
```

```
9361 ctatggcctc gcctccccac cctcctcttg gaattacaag ccctggggtt tgaagctgac 9421 tttatagctg caagtgtatc tccttttatc tggtgcctcc tcaaacccag tctcagacac 9481 taaatgcaga caacaccttc ctcctgcaga cacctggact gagccaagga ggcctgggga 9541 ggccctaggg gagcaccgtg atggagagga cagagcaggg gctccagcac cttctttctg 9601 gactggcgtt cacctccctg ctcagtgctt gggctccacg ggcaggggtc agagcactcc 9661 ctaatttatg tgctatataa atatgtcaga tgtacataga gatctatttt ttctaaaaca 9721 ttcccctccc cactcctctc ccacagagtg ctggactgtt ccaggccctc cagtgggctg 9781 atgctgggac ccttaggatg gggctcccag ctcctttctc ctgtgaatgg aggcagagac 9841 ctccaataaa gtgccttctg ggcttttct a
```

SEQ ID NO:11—531 bp GC3 DNA sequence isolated from modified RDA. GC3 is located within intron 7 and extends to exon 8 of the ELF3 gene between 7514 to 8045 (using SEQ ID NO:1 numbering). The GC3 primers are in bold, the 202 bp GC3 fragment amplified by GC3 primers are underlined.

```
CCGGGCTGAGCGGCTTCCTGGGGCACTGCGGGTTGTTGCAGGTATCCCCTCTCCCG

TTTCCTCTGGCCTCCGCATGGCCTTTGGTAAGGCTGTGCACAAGCTGGGGGCTCTA

TGGTATCGGTCACCACCTAATTGCAGAGCCAGGCTTGGTGGTCCTGGAGAGGAGG

AGGAAATAAGGCTCCCAGTGGGAGGCTCATGGTACCAGAGTCCTGTCCACTGACT

CCAGTGTCCTGTCCACTGACTCCAGTTCTCTCTGCACTTGGCCACTGTCCTGCCCTC

TGGGTCACCCTCAATGTGAGGAGGCGGCTGGTGGGTCTTAGGTGGGCTGAGGAGA

AAAGCAGTCACTGCAGTACCCGCACAGAGGGCACTGCGGGGTCTCTGGAGAGGCT

TGCTGCATGCTGTGGCCAAGTCAAGCAGTGCACTGGGGCGGCAGGGCTGGCTGG

CCTTGGGTGAGAGGGGGCACCTGGATGGCAAACGGATGGAGGCTGGCTTGCAGCG

CCCAGAGGCACCCACCTGTGGGAGTTCATCCGG
```

SEQ ID NO:12—1002 bp unspliced mRNA of the ELF3 gene (from 6550 to 7551 of the ELF3 gene, using SEQ ID NO:1 numbering) in human breast tumor cell lines. The unspliced entire intron 4, intron 5, intron 6 and 5' portion of intron 7 are underlined. The intron/exon splice junction borders are in bold.

```
GTTGGATCATTGAGCTGCTGGAGAAGGATGGCATGGCCTTCCAGGAGGCCCTAGA

CCCAGGGCCCTTTGGTGAGAACCCGTTTTCTCCTTCCTTCCCCAGCCTGTCTTGTCC

CATCCCTGCCCCTCCACAGAGTGCTAGAGATGACCCCCTCCCCAGACTTCTTCCTCC

CTCAATTAGAAAAATTGCAGCAGGTCATCAGACCCATGGGCAGCATCACCTGTCCT

GGTCTGGTCCCCTGAGCCCTCTCTGAGTTCTCACCTCCTCTTCCCAGACCAGGGCA

GCCCCTTTGCCCAGGAGCTGCTGGACGACGGTCAGCAAGCCAGCCCCTACCACCCC

GGCAGCTGTGGCGCAGGAGCCCCCTCCCCTGGCAGCTCTGACGTCTCCACCGCAG

GTGAGAGCTCTCTCTGGGCCACAACCTCCCTTCCCCGAAGTGTCCCTTGTTCCCTCT

GGCTCCCAGCACCATAACTCAGGCCTTCTGGCAGGAACAGGAACAGGCTGGGAAG
```

-continued

```
TGTGTCCTGAGAGCCAGCAGCGTGGTTGAACAGAAGGTGGGCCGGCAGGGGACTT

ACTCTGACCCCGCCCCCCAGGGACTGGTGCTTCTCGGAGCTCCCACTCCTCAGACT

CCGGTGGAAGTGACGTGGACCTGGATCCCACTGATGCCAAGCTCTTCCCCAGCGG

TGAGTCGAGGGAGGTCCCCAAGAGGGCGTCCCATTTAGCAATGCACAGGGGGCCC

GGCTCTTCCTGCAGCCTTTTCCTGTAGAGGGGCTACTCTCCCTAACTCCCCTCTTGC

CCCTCCTTGACCTTCCACCACCGTCCCCACAGATGGTTTTCGTGACTGCAAGAAGG

GGGATCCCAAGCACGGGAAGCGGAAACGAGGCCGGCCCCGAAAGCTGAGCAAAG

AGTAGTGGGACTGTCTCGAGGGCAAGAAGAGCAAGCACGGTGAGCTCCGGGGGC

ACGTGGGTCCTCCCTGCGCCGGGCTGAGCGGCTTCCTGGGGCACTGCGGGTTGTTG
```

SEQ ID NO:13—An Alu$_{kwd}$—the bold letters indicates a 17 bp sequence located in the end of Alu sequence that repeats nucleotides 8746 to 8762 of ELF3 sequence

```
GTATGCTTGGCCTTTTCTTTTTTCTTCTTCTTCTTTTTATTTTTCGAGACAGGGTCTC

GCTCTGTCACCCAGGTTAGAGTGCAGTGGCACAATCTTGGCTCGCTACAACCTCTG

CCTGCCGGGTTCAAGTGATTCTTGTGCCTCAGCCTCCAAGTAGCTGGGATTACAGG

CACCTGCCACCATGCCCAGCTAATTTTTGTATTTTTAGTAGAGACGGGGTTTCAC

CATGTTGGCTAGGCTGGTCTCGAACTCCTGACCTCAAGTGATCCGCCCGCCTCAGC

CTCCCAAAGTGCTGGAATTACAGGTGTGAGCCA
```

SEQ ID NO:14—An antisense insertion of a 315 bp Alu$_{kwd}$ sequence in an ELF3 sequence. This sequence shows the ELF3 gene from nt 8685 to 9107 (numbering of SEQ ID NO:1) containing a 315 bp antisense insertion of the Alu$_{kwd}$ sequence. Underlined letters represent the 315 bp Alu$_{kwd}$ sequence, the bold letters indicates a 17 bp sequence located in the end of Alu$_{kwd}$ sequence that repeats nt 8746 to 8762 of the ELF3 sequence. The bracketed numbers shows the insert point of the Alu$_{kwd}$ in the ELF3 DNA sequence.

```
GGCCGGTCTCAAACTCCTGGCGTCAAATGACTCTCCTGCCTCGGCCTCTCAAAGTG

CTGGGATTACAGGTGTGAGCCA[8762]GTATGCTTGGCCTTTTCTTTTTCTTCTTCT

TCTTTTTATTTTTCGAGACAGGGTCTCGCTCTGTCACCCAGGTTAGAGTGCAGTGGC

ACAATCTTGGCTCGCTACAACCTCTGCCTGCCGGGTTCAAGTGATTCTTGTGCCTCA

GCCTCCAAGTAGCTGGGATTACAGGCACCTGCCACCATGCCCAGCTAATTTTTGTA

TTTTTAGTAGAGACGGGGTTTCACCATGTTGGCTAGGCTGGTCTCGAACTCCTGA

CCTCAAGTGATCCGCCCGCCTCAGCCTCCCAAAGTGCTGGAATTACAGGTGTGAG

CCA[8763]CCGTGCCCAGCTCCCTGGCCTTAAAAGTCATGTAATTTAATGATCAGAC

CCCAGTCACAGCCATAGGATACAAAGAAGCAAAGGCAAAGAGCCCTGTGTCCTGG

GCACGGTTACAGGCCAGTGTAGGGAAAGAGCTTCTGCTTGCCAGTGTGAAGAACA

GAGGAGTTTAGGAAGTGTGAGTCAGGCTCAGCTTAGTCAGGCAGAGACCAGTGGG

CATGGGTTACCTGGGGGTAACGCGGGCCAGGTGGGCGGGCTGGCAGCCTGGGGCC

CATTTCCTGCCAAAGCACCTCTGACCATCCTTCTCTTCACCCAGGTACTACTACAAA
```

-continued

CGGGAGATCCTGGAACGGG

SEQ ID NO: 15 - the sequence of the novel ELF3 5' UTR.
ctccgccactccggtaggattccccgcctgtcattccctagcccagctcttgggaaactgcagaggggtccagaggatttgcagttctgaa cctgcacactccagtctaggatctccgagcaagagcgtagcctc SEQ ID NO: 16 - GC3 sense primer - codons 7722-7741 of the ELF3 gene.
CCTGTCCACTGACTCCAGTG SEQ ID NO: 17 - GC3 antisense primer - codons 7923-7905 of tbe ELF3 gene.
ACTTGGCCACAGCATGCAG SEQ ID NO: 18 - GC3 UPF antisense primer - codons 7572-7598 of the ELF3 gene.
ACCAAAGGCCATGCGGAGGCCAGAGAA SEQ ID NO: 19 - GC3 UPN antisense primer - codons 7523-7551 of the ELF3 gene.
CAACAACCCGCAGTGCCCCAGGAAGCCC SEQ ID NO: 20 - GC3 DF sense primer - codons 7943-7970 of the ELF3 gene.
GCAGGGCTGGCTGGCCTTGGGTGAGAGG SEQ ID NO: 21 - GC3 DN sense primer - codons 8004-8030 of the ELF3 gene.
CTTGCAGCGCCCAGAGGCACCCACCTG SEQ ID NO: 22 - GC3 (1-3) sense primer - codons 4819-4843 of the ELF3 gene.
GCTACCTGGCGGAACTGGATTTCTC SEQ ID NO: 23 - GC3 (1-3) antisense primer - codons 6240-6216 of the ELF3 gene.
CGCTTGCGTCGTACTTGTTCTTCTC SEQ ID NO: 24 - GC3 (3-6) sense primer - codons 6180-6205 of the ELF3 gene.
AAGACGCAGGTTCTGGACTGGATCAG SEQ ID NO: 25 - GC3 (3-6) antisense primer - codons 7194-7171 of the ELF3 gene.
TGGGATCCAGGTCCACGTCACTTC SEQ ID NO: 26 - GC3 (6-8) sense primer - codons 7155-7179 of the ELF3 gene.
TCCTCAGACTCCGGTGGAAGTGACG SEQ ID NO: 27 - GC3 (6-8) antisense primer - codons 8109-8174 of the ELF3 gene.
CCGGCTCAGCTTCTCGTAGGTCATG SEQ ID NO: 28 - GC3 (8-9) sense primer - codons 8065-8089 of the ELF3 gene.
AGCTCAACGAGGGCCTCATGAAGTG SEQ ID NO: 29 - GC3 (8-9) antisense primer - codons 9352-9327 of the ELF3 gene.
TCCCAGGACGATGGCTGACAATACAC SEQ ID NO: 30 - β-actin ES31 primer
CCCCAGCCATGTACGTTGCTATCC SEQ ID NO: 31 - β-actin ES33 primer
GCCTCAGGGCAGCGGAACCGCTCA SEQ ID NO: 32 - GC3DD sense primer - codons 8569-8596 of the ELF3 gene.
CCTGTGTCCAGGAGTACACTAGATCATC SEQ ID NO: 33 - INSE sense primer - codons 8659-8680 of the ELF3 gene.
AGAGGCAAGGGTCTCTACGTTG SEQ ID NO: 34 - INSE antisense primer - codons 8774-8795 of the ELF3 gene.
TCCCTGGCCTTAAAAGTCATGT

What is claimed is:

1. An isolated cDNA molecule of a mammalian ELF3 gene, wherein said cDNA molecule consists of an ELF3 cDNA sequence and one or more of intron 4, intron 5, intron 6, intron 7 and intron 8 of the ELF3 gene, wherein the ELF3 gene consists of a contiguous sequence set forth in SEQ ID NO:10.

2. The cDNA molecule of claim 1, wherein the intron is selected from the group consisting of intron 4, intron 5, intron 6 and intron 7.

3. The cDNA molecule of claim 1, comprising SEQ ID NO:11.

4. The cDNA molecule of claim 1, wherein the cDNA molecule comprises the nucleotide sequence of SEQ ID NO:15.

* * * * *